(12) United States Patent
Hoatlin et al.

(10) Patent No.: US 8,030,004 B2
(45) Date of Patent: Oct. 4, 2011

(54) CELL FREE SCREENING ASSAY AND METHODS OF USE

(75) Inventors: Maureen Hoatlin, Portland, OR (US); Stacie Stone, Oregon City, OR (US); Alexandra Sobeck, Portland, OR (US); Vincenzo Costanzo, Herts (GB); Jean Gautier, New York, NY (US); Igor Landais, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 263 days.

(21) Appl. No.: 12/096,142

(22) PCT Filed: Oct. 18, 2006

(86) PCT No.: PCT/US2006/040906
§ 371 (c)(1),
(2), (4) Date: Jun. 4, 2008

(87) PCT Pub. No.: WO2007/067261
PCT Pub. Date: Jun. 14, 2007

(65) Prior Publication Data
US 2008/0318236 A1    Dec. 25, 2008

Related U.S. Application Data

(60) Provisional application No. 60/748,127, filed on Dec. 6, 2005.

(51) Int. Cl.
*G01N 33/53* (2006.01)
*C12Q 1/68* (2006.01)

(52) U.S. Cl. .......................... 435/7.1; 435/6

(58) Field of Classification Search .................. None
See application file for complete search history.

(56) References Cited

FOREIGN PATENT DOCUMENTS

| WO | WO 02/36761 A2 | 5/2002 |
| WO | WO 03/039327 A2 | 5/2003 |

OTHER PUBLICATIONS

Chirnomas et al., "Chemosensitization to cisplatin by inhibitors of the Fanconi anemia/BRCA pathway," *Mol Cancer Ther*, 5(4):952-961 (2006).
Costanzo et al., "Mre11 Protein Complex Prevents Double-Strand Break Accumulation during Chromosomal DNA Replication," *Molecular Cell*, 8:137-147 (2001).
D'Andrea et al., "The Fanconi Anaemia/BRCA Pathway," *Nature Review*, 3:23-34 (2003).
Di Virgilio et al., "Repair of double-strand breaks by nonhomologous end joining in the absence of Mre11," *The Journal of Cell Biology*, 171(5):765-771 (2005).
Houghtaling et al., "Epithelial cancer in Fanconi anemia complementation group D2 (Fancd2) knockout mice," *Genes & Dev*, 17:2021-2035 (2003).
Jin et al., "Menin Associates with FANCD2, a Protein Involved in Repair of DNA Damage," *Cancer Research*, 63:4204-4210 (2003).
Kennedy et al., "The Fanconi Anemia/BRCA pathway: new faces in the crowd," *Genes & Development*, 19(24):2925-2940 (2005).
Lord et al., "Targeting the Double-Strand DNA Break Repair Pathway as a Therapeutic Stategy," *Clin Cancer Res*, 12(15):4463-4468 (2006).
Nakanishi et al., "Human Fanconi anemia monoubiquitination pathway promotes homologous DNA repair," *PNAS*, 102(4):1110-1115 (2005).
Reichenberger et al., "A novel nuclease activity from *Zenopus laevis* releases short oligomers from 5'-ends of double- and single-stranded DNA," *Genes to Cells*, 1:355-367 (1996).
Sobek et al., "Coordinated chromatin-association of Fanconi anemia network protein required replication-coupled DNA damage recognition," *Blood*, 104(11):207A (2004). Abstract only.
Sobek et al., "The Fanconi anemia pathway is conserved in *Xenopus*," *Blood*, 102(11):358a (2003). Abstract only.
Surrallès et al., "Molecular cross-talk among chromosome fragility syndromes," *Genes & Dev*, 18:1359-1370 (2004).
Verma et al., "Ubistatins Inhibit Proteasome-Dependent Degradation by Binding the Ubiquitin Chain," *Science*, 306(5693):117-120 (2004).
Wignall et al., "The condensing complex is required for proper spindle assembly and chromosome segregation in *Xenopus* egg extracts," *The Journal of Cell Biology*, 161(6):1041-1051 (2003).

*Primary Examiner* — Anne M. Gussow
(74) *Attorney, Agent, or Firm* — Klarquist Sparkman, LLP

(57) ABSTRACT

Methods are disclosed for identifying agents for the treatment of cancer and/or Fanconi anemia using *Xenopus* egg cell free extracts from which the endogenous DNA has been removed. The assays and method described herein are easily adaptable to high throughput techniques for example to screen large numbers of agents as possible agents for the treatment of cancer and/or Fanconi anemia. Kits for carrying out the disclosed assays and methods also are disclosed. Agents identified by these methods are also disclosed as are methods for treating a subject with cancer and/or Fanconi anemia with these agents.

26 Claims, 19 Drawing Sheets

A
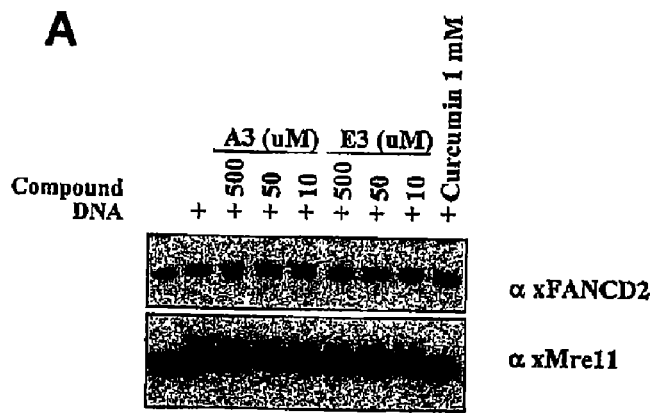
B
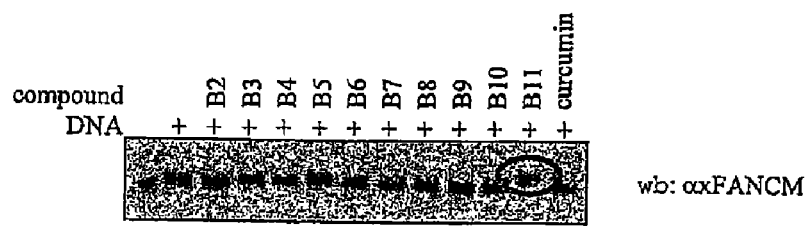
Row B, first plate of the Natural Products set (NCI)
FIG. 7

A
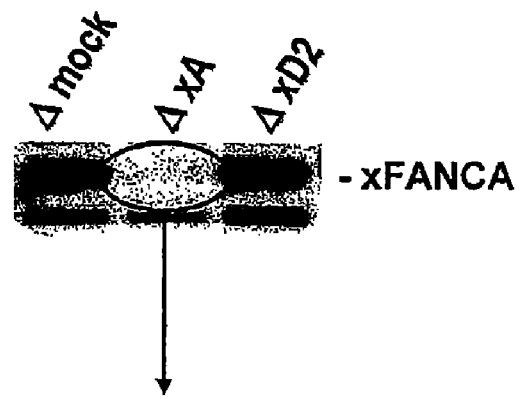
B
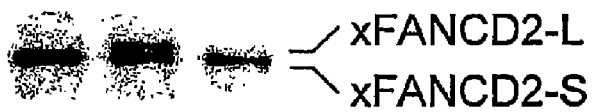
FIG. 8

```
xFANCM     1 MSGKQKTLFQTWGNNQ-----PPETRKAKETKPRK--ARQQPSTCQQEVE   43
hFANCM     1 MSGRQRTLFQTWGSSISRSSGTPGCSSGTER-PQSPGSSKAPLPAAAEAQ   49
             ***.*.*******        *    * *.  .  .*  .  *.

xFANCM    44 DD-DDDVLLVAVYEAEKTLNQ-SGILNGEAGSVWIYPTNYLIRDYQFNIS   91
hFANCM    50 LESDDDVLLVAAYEAERQLCLENGGFCTSAGALWIYPTNCPVRDYQLHIS   99
             . ******** ****. *      *   **..******  **** .**

xFANCM    92 YTALLQNTLVCLPTGLGKTFIAAVVMYNFYRWYPSGKIVFMAPTKPLVAQ  141
hFANCM   100 RAALFCNTLVCLPTGLGKTFIAAVVMYNFYRWFPSGKVVFMAPTKPLVTQ  149
              . ***********************..*********.* xFANCM   142 QIEACFRVMGIPQDHMAEMTGSTQAQNRKDMWEKHRVPFLTPQVMVNDLT  191
hFANCM   150 QIEACYQVMGIPQSHMAEMTGSTQASTRKEIWCSKRVLFLTPQVMVNDLS  199
             *****..****** *********** .**..*  .** ***********.

xFANCM   192 RGACPASEIKCLVIDEAHKALGNHAYCQVVRELTNYTNQFRILALSATPG  241
hFANCM   200 RGACPAAEIKCLVIDEAHKALGNYAYCQVVRELVKYTNHFRILALSATPG  249
             ****.************.***** .*.********** xFANCM   242 GDTKSVQQVVSNLLISQIELRSEDSPDIQPYSHERQLEKFVVPLGEELES  291
hFANCM   250 SDIKAVQQVITNLLIGQIELRSEDSPDILTYSHERKVEKLIVPLGEELAA  299
              * *.****..**** ************  *****..** .******  .

xFANCM   292 VQKTYLQVLETFAGRLLKNNVLSRRDIPNLTKYQIILSRDQFRKNPPANI  341
hFANCM   300 IQKTYIQILESFARSLIQRNVLMRRDIPNLTKYQIILARDQFRKNPSPNI  349
             .****.*..  .. * ***********.**** xFANCM   342 IVAQQGVIEGDFALCISLYHGYELLLQMGTRSLYSYLHGIMDGSKGMTRA  391
hFANCM   350 VGIQQGIIEGEPAICISLYHGYELLQQMGMRSLYFFLCGIMDGTKGMTRS  399
              . ***.***.**.********** **** ****  *.  *****.*****.

xFANCM   392 RNELSRNGDFMELYQQLENMFSDLNVTEGNGSLLFNTNAK-KPFVYSHPK  440
hFANCM   400 KNELGRNEDFMKLYNHLECMFARTRSTSANGISAIQQGDKNKKFVYSHPK  449
             .*  * .. .     *     . . * ****** xFANCM   441 LIKLEDVVIQHFKSWNXXXXXXXXXXXTRIMIFSSFRDSVQEIAEMLNQH  490
hFANCM   450 LKKLEEVVIEHFKSWNAENTTEKKRDETRVMIFSSFRDSVQEIAEMLSQH  499
             * *.*.****                 .************* xFANCM   491 HPTVRVMTFVGHSSAGKGVKGFTQKEQLEVVKRFREGGFNTLVSTCVGEE  540
hFANCM   500 QPIIRVMTFVGHAS-GKSTKGFTQKEQLEVVKQFRDGGYNTLVSTCVGEE  548
             .*. *********.*   ********...********* xFANCM   541 GLDIGEVDLIICFDAQKSPIRLVQRMGRTGRKRQGRIVVILCQGREERTY  590
hFANCM   549 GLDIGEVDLIICFDSQKSPIRLVQRMGRTGRKRQGRIVIILSEGREERIY  598
             ************.******************...****** * xFANCM   591 NQSQSNKRSIFKAILGNNKMLHLNPQSPRMVPEGLNPKVHKMFITQGNYE  640
hFANCM   599 NQSQSNKRSIYKAISSNRQVLHFYQRSPRMVPDGINPKLHKMFITHGVYE  648
             ********.*   *  .**  *.******.* *.**** * ** xFANCM   641 AKESIRPKHKDRRSSTKHCNSSLFLNASDTLKEEWDLTHAEFETWNRLYR  690
hFANCM   649 PEKPSRNLQ--RKSSIFSYRDGMRQ---SSLKKDWFLSEEEFKLWNRLYR  693
              *  . *   .**        *     .   .  ** .*    ***** xFANCM   691 LQESDGIMDVRLPKSQFEYFRDAE--PNKERPSGNIHKLSLTEWRVWQNR  738
hFANCM   694 LRDSDEIKEITLPQVQFSSLQNEENKPAQESTTG-IHQLSLSEWRLWQDH  742
             *..** *  ..  **. **  **     .* .*  ** .***.***.** .

xFANCM   739 PFPTDSVDHSDRCKNFIHVMEMIELMRLEEGDCNYDLEMMSYLNKEDVDP  788
hFANCM   743 PLPTHQVDHSDRCRHFIGLMQMIEGMRHEEGECSYELEVESYLQMEDVTS  792
             *  ****..  ..*  * .*.* *.  * xFANCM   789 TATNTRAINVLDNNSVAEKSTHPKK--GKTYKNTPLSLVLEPDEDFMSS  836
hFANCM   793 TFIAPRNE---SNNLASDTFITHKKSSFIKNINQGSSSSVIEBSDE-ECAE  838
             *  *   **    **    **.*   *..   *.*.**  .

xFANCM   837 CKKITKSHSTDFVAVDSKVHAQGTEEGGSTELERVVGLNED-DHG--KES  883
hFANCM   839 IVKQTHIKPTKIVSLKKKVSKEIKKDQLKKENNHGIIDSVDNDRNSTVEN  888
              *.. * *..  **      . .  .      * *..      *   * xFANCM   884 VFSANVTKYK---DSRSNAVTSNQSDS----DHMLLSDTEDAVAKSQSNV  926
hFANCM   889 IFQEDLPNDKRTSDTDEIAATCTINENVIKEPCVLLTECQFTNKSTSSLA  938
              .*   . * *..        . *.. .          .**.... *     * xFANCM   927 DAKADSGYHSFNEDPSSNLSNLFYTPQSFINHGVFTEFVDNKICELKKML  976
hFANCM   939 GNVLDSGYNSFN-DEKSVSSNLFLPFEEELYIVRTDDQFYNCHSLTKEVL  987
              **.*  *  ****   .    .    .   *  .*  .* xFANCM   977 LHIKRFLSHSPPPINELDCLDDPQKYENFSHHSCLSDPVKDKTQEDLLLQ 1026
hFANCM   988 ANVERFLSYSPPPLSGLSDL-EYEIAKGTALENLLFLPCAEHLRSDKCTC 1036
              ..**.**. *  *  .  *  ...   .       * *  ..* xFANCM  1027 PLTQQPLTPVPVTINSKEMQAELNHKKQTDSVAGTLLPATEVKKDDVLFG 1076
hFANCM  1037 LLSHS-------AVNS-QQNLELNSLKCIN------YPSEKSCLYDIPND 1072
             *..         ..** . . ***  *           *.     *.
```

FIG. 15A

```
xFANCM  1027 PLTQQPLTPVPVTINSKEMQAELNHKKQTDSVAGTLLPATEVKKDDVLFG 1076
hFANCM  1037 LLSHS-------AVNS-QQNLELNSLKCIN------YPSEKSCLYDIPND 1072
             *..      ..**. . ***  *       *.        *.

xFANCM  1077 EDRLKPRDVIQTVGGKAACSEKNVGFYSEDSSKPSSSKDLHDVRTENDDH 1126
hFANCM  1073 NISDEP---------SLCDCDVHKHNQNENLVPNNRVQIHRSPAQN---  1109
              *          .   *     *       *   .*    ..* xFANCM  1127 WDELFDYESQDKENENFTFQVNMPVLEGGDTEGSSAENENHNIDSVPTFL 1176
hFANCM  1110 ---LVGENNHDVDNS------DLPVLSTDQDE-S---------LLLFEDV 1140
                *     .* .*     .***    * *            * * xFANCM  1177 EDSFDLFEEDGFSDNANYGQLHSKHESTDKPHENAKTTVTFNMFDPSSLL 1226
hFANCM  1141 NTEFDDVSLSPLNSKSESLPVSDKTAISETPLVSQFLISDELLLDNNSEL 1190
             **           .  *  ..*      .  *     .  * ** xFANCM  1227 QEQVQTEDEPE-TKDDIWSQE-----NLEELDCSEELYSVNFDLGFSIED 1270
hFANCM  1191 QDQITRDANSFKSRDQRGVQEEKVKNHEDIFDCSRDLFSVTFDLGFCSPD 1240
             *.*.     ..*          *.*..***. * xFANCM  1271 DELSESDGKNETPSKDSKDDELSEIDSKNETPSKDSKDDNLSDSKNVTP- 1319
hFANCM  1241 -----SDDEILEHTSDS-NRPLDDLYGR-YLEIKEISDANYVSNQALIPR 1283
                          .      *...     *.  * *    .  * xFANCM  1320 --SKDFKVPNPLKRNDMNAIGGNAVSTPVVSSNICSTFSEVAEKQIHLFS 1367
hFANCM  1284 DHSKNFTSGTVIIPSNEDMQNPNYVHLPLSAAKNE----ELLSPGYSQFS 1329
               ** *   ..      . *  *..       *.       **

xFANCM  1368 PLEPVRGKISLTPE-KSLCSSSFFTPIGEKFRSPQTPLGNLCDSEAGELQ 1416
hFANCM  1330 --LPVQKKVMSTPLSKSNTLNSFSKIRKEILKTP------DSSKEKVNLQ 1371
               **. *. .. **      *  ..*     ..     *   ** xFANCM  1417 SPKAGEKSIHSTTNFSVHDGRVVQAERRQTNSCS--EHSLIESSPESEDD 1464
hFANCM  1372 RFKEALNSTFDYSEFSLEKSKSSGP-MYLHKSCHSVEDGQLLTSNESEDD 1420
              *    *   .**.        *      **  *    .* ***** xFANCM  1465 VVICRKRKLTKANVLMSPQTASSDCDFDSPIPTAKKRRHVLKTPDSDEEE 1514
hFANCM  1421 EIFRRKVKRAKGNVLNSPEDQK-NSEVDSPLHAVKKRRFPINRSELSSSD 1469
              .  **  *  * *         .*   .. *.  **** xFANCM  1515 EEDDFKSTHSTARDKSAGHSRKSYQHRAIAVSKKRKRCKQRARQFLDEEA 1564
hFANCM  1470 ESENFPKPCSQLEDFKVCNGN---ARRGIKVPKRQSHLKHVARKFLDDEA 1516
             *. *    *    . *  .     .* * * *.,   ,. ** ***.**

xFANCM  1565 ELSSEGAEFVSSDEDMNSDNEQDTSLVEFLNDDPQLSQALNDSEMHGVYL 1614
hFANCM  1517 ELSEEDAEYVSSDENDESENEQDSSLLDFLNDETQLSQAINDSEMRAIYM 1566
             *** * **.*****  *.****.**. ****. ******.*****. *.

xFANCM  1615 KSVRSPAFGGRFKMAPQRRRHNMSVFSQIPEQDESYMEDSFCVQEEDDEE 1664
hFANCM  1567 KSLRSPMMNNKYKMIH-KTHKNINIFSQIPEQDETYLEDSFCVDEE---- 1611
             **.***    .. **   ...*. .*********.*.******.**

xFANCM  1665 EADNLGSSEEEVEINFDLLKDVSIVGGKKQYCTRRRLKLKEAQSRQLFLS 1714
hFANCM  1612 ESCKGQSSEEEVCVDFNLITDDCFANSKK-YKTRRAVMLKEMMEQNCAHS 1660
             *.   ******  . *.* .*  . . **  * *..   .*   * xFANCM  1715 SGQLPDLLLLISYLPEEVSIG--------------------------- 1735
hFANCM  1661 KKKLSRIILPDDSSEEENNVNDKRESNIAVNPSTVKKNKQQDHCLNSVPS 1710
              .* ..*    **   **  ..

xFANCM  1736 -----------RVN----------FDLTMDSSAVANLS----------- 1752
hFANCM  1711 GSSAQSKVRSTPRVNPLAKQSKQTSLNLKDTISEVSDFKPQNHNEVQSTT 1760
                        ***              * *.

xFANCM  1753 --------------FPG-----------TVGVSA------LAGIRT--- 1767
hFANCM  1761 PPFTTVDSQKDCRKFPVPQKDGSALEDSSTVSGASCSKSRPHLAGTHTSLR 1810
                           **            * * *     *** .* xFANCM  1768 -------LCILADSREISSGPEVISYLKMSLGVKVEVCSLGGCDYIVSSR 1810
hFANCM  1811 LPQEGKGTCILVGGHEITSGLEVISSLRAIHGLQVEVCPLNGCDYIVSNR 1860
                    *. . ** *.   *..** .*******. * xFANCM  1811 LAVERKSQSEFANSANRSKLVDRIQHLQHLFDRVCLIIEKDRIKQGETSR 1860
hFANCM  1861 MVVERRSQSEMLNSVNKNKFIEQIQHLQSMFERICVIVEKDREKTGDTSR 1910
              .*.. .  *. ..,*****  .*.*  *.***** *. *** xFANCM  1861 TFQRTRYYDSTLSALISAGVQVLFSSSQEETAGLLKELGLLEQRKNTGID 1910
hFANCM  1911 MFRRTKSYDSLLTTLIGAGIRILFSSCQEETADLLKELSLVEQRKNVGIH 1960
              *.**. *** *. **.*** .****.******.****.*.******.**

xFANCM  1911 VPTEVKGHKQEVMQFYLSIPNISYITALNLCQRFDSIRQMANSSVQVISA 1960
hFANCM  1961 VPTVVNSNKSEALQFYLSIPNISYITALNMCHQFSSVKRMANSSLQEISM 2010
             ***  *  .*  .*****************.* .*.*..******.* ** xFANCM  1961 RAHVSAQKAEELYRYVHYMFEAEMVASENPAKRSRVSZ 1998
hFANCM  2011 YAQVTHQKAEEIYRYIHYVFDIQMLPNDLNQDRLKSDI 2048
              *.*. *****.***.**.*. .*. ..  . * .
```

CELL FREE SCREENING ASSAY AND METHODS OF USE

CROSS REFERENCE TO RELATED APPLICATION

This is the section 371 U.S. National Stage of International Application No. PCT/US2006/040906, filed Oct. 18, 2006, which claims priority to U.S. Provisional Application No. 60/748,127, filed Dec. 6, 2005, which is incorporated by reference herein in its entirety.

ACKNOWLEDGMENT OF GOVERNMENT SUPPORT

This work was supported in part by funds from the National Institutes of Health under NILBI contract number HL056045 and under NCI contract number CA112775. The government has certain rights in this invention.

FIELD

This disclosure relates to a cell free assay for activation of the Fanconi anemia pathway. This disclosure further relates to methods of use of this cell free assay.

BACKGROUND

Fanconi anemia (FA) is an hereditary cancer susceptibility syndrome belonging to a group of caretaker gene diseases, and is characterized by genetic instability and cellular hypersensitivity to DNA interstrand crosslinking agents such as mitomycin C (MMC). The cellular hypersensitivity of FA to DNA interstrand crosslinks (ICLs) suggests a defect in the DNA damage response. FA proteins are believed to function at the interface between cell cycle checkpoints, DNA repair and DNA replication. There are at least twelve genes involved in FA. Thus far eleven FA genes have been identified; FANCA, -B, -C, -D1, -D2, -E, -F, -G, -J, -L, and -M (Meetei et al., *Nat. Genet.* 36:1219-24, 2004; Levitus et al., *Nat. Genet.* 37:934-5, 2005; Levran et al., *Nat. Genet.* 37:931-3, 2005). FANCI has not yet been identified. It is believed that monoubiquitination and/or phosphorylation of FANCD2 in response to DNA damage by cross-linking agents promotes co-localization of FANCD2, FANCD1, BRCA1, and RAD51 to damage-induced nuclear foci and activation of the Fanconi anemia pathway (Taniguchi et al., *Blood* 100:2414-20, 2002; Hussain et al., *Human Mol. Genet.* 13:1241-8, 2004; Shimamura et al., *Blood* 100:4649-54, 2002).

Identification of BRCA2 (breast cancer associated gene 2) as FANCD1, and FANCJ as the BRCA1-associated helicase Brip1/BACH1, suggests convergence of the FA/BRCA pathway within a larger network of proteins involved in DNA repair. This convergence is further underscored by the involvement of the FA pathway in the formation of the MRE11-RAD50-NBS1 (MRN) complex on sites of DNA damage. The MRN complex is an element of the homologous recombination pathway believed to be required for processing DNA prior to homologous recombination (Nakanishi et al., *Nat. Cell Biol.* 4:913-920, 2002; Kobayashi et al., *DNA repair (Amst.)*, 3:855-861, 2004). In the absence of FA pathway activation the MRN complex fails to associate with the sites of DNA damage (Penichierri et al., *Hum Mol. Genet.*, 11:2531-2556, 2002). It has been hypothesized that FA proteins are likely to function in ICL removal via homologous recombination repair, a variation of homologous recombination, or another mechanism, during S-phase.

It is believed that dysregulation of the FA pathway occurs in 10% of human cancers including ovarian cancer (Taniguchi et al., *Nature Med.* 9:568-574, 2003) head and neck cancer (Marsit et al., *Oncogene* 23:1000-1004, 2004), lung cancer (Marsit et al., *Oncogene* 23:1000-1004, 2004), cervical cancer (Narayan et al., *Cancer Research* 64:2994-2997, 2004) and pancreatic cancer (van der Heijiden et al., *Am J. Pathol.* 165:651-657, 2004). Determining the effects of potential therapeutics on the activity of the Fanconi anemia pathway is critical to the development of future anti-cancer agents and Fanconi anemia therapies. Thus, the needs exist for assays to determine the effects of therapeutic agents on the Fanconi anemia pathway.

SUMMARY

Disclosed herein are methods for identifying agents for the treatment of cancer and/or Fanconi anemia using *Xenopus* egg cell free extracts from which the endogenous DNA has been removed. These methods involve contacting a *Xenopus* egg cell free extract depleted of endogenous DNA with an agent of interest and detecting a post-translationally modified *Xenopus* Fanconi anemia polypeptide in the *Xenopus* egg cell free extract. In some examples, the post-translationally modified Fanconi anemia protein is FANCD2. In some examples, the post-translationally modified Fanconi anemia protein is FANCM.

The assays and methods described herein are easily adaptable to high throughput techniques for example to screen large numbers of agents to determine if they are of use for the treatment of cancer and/or Fanconi anemia. Agents identified with the disclosed methods are useful in treating subjects with cancer and/or Fanconi anemia. Kits for carrying out the disclosed assays and methods also are disclosed.

The foregoing and other objects, features, and advantages of the invention will become more apparent from the following detailed description, which proceeds with reference to the accompanying figures.

BRIEF DESCRIPTION OF THE DRAWINGS

FIG. 1A shows a schematic of a procedure used to determine the effect of cut plasmid DNA in cell free extracts of *Xenopus* eggs. FIG. 1B is a digital image of an immunoblot demonstrating that xFANCM is post-translationally modified in response to the addition of digested plasmid DNA to *Xenopus* egg cell free extracts. FIG. 1C schematically illustrates a procedure to determine the effect of an agent in cell free extracts of *Xenopus* eggs.

FIG. 2A is a digital image of an immunoblot showing nuclear accumulation and chromatin-binding of FA proteins during replication. Sperm chromatin was added to S-phase *Xenopus* egg extracts and re-isolated at indicated time points during replication. Nuclear or chromatin fractions were analyzed by SDS-polyacrylamide-gel-electrophoresis (PAGE) and immunoblotted with the indicated antibodies. *Xenopus* XTC-2 cell lysates were used as a control for xFANCD2-S (short form), -L (long form) and xFANCA; a lysate containing Flag-tagged xFANCF (overexpressed in 293 EBNA cells) was used as positive control. The suffix -chr indicates the chromatin-bound protein isoforms from *Xenopus* egg extracts as described. FIG. 2B is a digital image of an immunoblot that shows the results of replication assays. Throughout the experimental procedure described in FIG. 2A, semiconservative replication was monitored by pulsing replicating extract aliquots with $\alpha$-$^{32}$P-GTP at time windows 0-30, 30-60, and 60-90 minutes. FIG. 2C is a digital image of an immunoblot that shows the isoforms of xFANCD2 detectable in M- and S-phase, and in chromatin fractions from replicating nuclei. An isoform of xFANCD2 with relatively slower mobility associates with chromatin during replication (xFANCD2-L). Electrophoretic mobility was compared among xFANCD2 isolated from XTC-2 cell lysates, DNA-free mitotic egg extracts (M-phase), DNA-free S-phase egg extracts (S-phase), and from nuclear sperm chromatin replicating in S-phase egg extracts (chromatin). FIG. 2D is a digital image of an immunoblot that shows a comparison of chromatin binding patterns between xFA proteins and other DNA replication-associated proteins. Sperm chromatin was added to cycloheximide-containing S-phase egg extracts, chromatin fractions were re-isolated at the times shown and analyzed for the indicated proteins by immunoblotting. FIG. 2E is a digital image of an immunoblot that shows that xFA proteins dissociate from chromatin in non-arrested extracts following replication. Sperm chromatin was added to S-phase egg extracts in the absence of cycloheximide. Chromatin fractions were re-isolated at the indicated time points and analyzed for xFANCA, xFANCD2, and xFANCF by immunoblotting. A non-specific band is indicated (asterisk) as a loading control.

FIG. 3A upper left panel is a digital image of an immunoblot that shows S-phase extracts were treated as indicated and supplemented with sperm chromatin. Following replication (60 minutes), chromatin was re-isolated and the same blot was assayed in series for the presence of the xFA proteins indicated. A non-specific band is indicated (asterisk) as a loading control. FIG. 3A upper right panel is a digital image of an autoradiograph that shows MMC-treated extracts activate a caffeine-sensitive S-phase checkpoint. A replication assay was performed to monitor incorporation of $\alpha$-$^{32}$P-GTP during one round of replication in extracts treated as indicated. Total amounts of replication products at 60 minutes following addition of sperm chromatin to non-treated or treated extracts were analyzed by agarose gel electrophoresis and exposure to X-ray film. Band density percentages were determined using a BioRad Molecular PhosphorImager Fx (Kodak screens, Quantity-1 software). FIG. 3A lower panel is a digital image of an autoradiograph that shows rescue of dose-dependent, MMC-induced replication reduction by neutralizing xATR. 1000 sperm pronuclei/ul were added to replicating extracts containing different concentrations of MMC (lanes 3-9). Extracts were otherwise untreated or contained caffeine (lanes 6+7) or a neutralizing anti-xATR antibody (lanes 8+9). MMC-concentrations: 150 µM (lanes 3, 6, 8), 50 µM (lanes 4, 7, 9), or 5 µM (lane 5). FIG. 3B is a digital image of an immunoblot that shows stalling of replication forks induces recruitment of xFA proteins to chromatin. Sperm chromatin was added to S-phase egg extracts. Xenopus egg extracts were either untreated (−) or aphidicolin was added (+) at the indicated time points following addition of sperm DNA: 0 minutes, pre-nuclear membrane formation; 30 minutes, beginning of replication; 60 minutes, mid-replication; 90 minutes late/post-replication; and 120 minutes, post replication. All chromatin fractions were re-isolated at 135 minutes following addition of sperm DNA, analyzed by SDS-PAGE and immunoblotted as indicated. FIG. 3C is a digital image of an immunoblot that shows chromatin binding of xFANCD2 is xATRIP-dependent. Xenopus egg extracts were treated with beads coupled to preimmune serum (lanes 2, 3, and 5) or beads coupled to anti-xATRIP serum (lanes 1, 4, and 6). Sperm chromatin was added to preimmune or xATRIP depleted extracts and allowed to replicate. Xenopus egg extracts were either untreated or supplemented with aphidicolin (added at 50 minutes following addition of sperm DNA). Chromatin fractions were re-isolated at 70 minutes and assayed for the presence of xFANCD2, xFANCA, xATRIP and xORC-2 by immunoblotting. FIG. 3D is a digital image of an immunoblot that shows chromatin binding of xATRIP is xFANCA-independent. Xenopus egg extracts were treated with beads coupled to preimmune serum (lanes 1 and 3) or beads coupled to anti-xFANCA serum (lanes 2 and 4). Sperm chromatin was added to preimmune or xFANCA depleted extracts and allowed to replicate. Xenopus egg extracts were either untreated or supplemented with aphidicolin (added at 50 minutes following addition of sperm DNA). Chromatin fractions were re-isolated at 70 minutes and assayed for the presence of xFANCA, xATRIP and xORC-2 by immunoblotting.

FIG. 4A is a digital image of an immunoblot showing S-phase egg extracts that were incubated either with bead-coupled anti-xFANCA antibody (xA) or with bead-coupled pre-immune serum (Pre) and assayed for presence of xFANCA. Right lane: xFANCA binds to anti-xFANCA-beads during the depletion process. FIG. 4B is a digital image of an immunoblot that shows the effect then sperm chromatin was added to xA- or Pre-depleted extracts, re-isolated following replication and assayed for the presence of xFANCD2-chr by immunoblot. FIG. 4C and FIG. 4D are digital images of immunoblots that show replication-associated chromatin binding of xFANCA does not require the presence of xFANCD2. FIG. 4C, S-phase Xenopus egg extracts were incubated either with bead-coupled anti-xFANCD2 antibody (xD2) or with bead-coupled pre-immune serum (Pre), and assayed for presence of xFANCD2 by immunoblot. Right lane: xFANCD2 binds to anti-xFANCD2-beads during the depletion process. FIG. 4D, sperm chromatin was added to xD2- or Pre-depleted extracts, re-isolated following replication and assayed for the presence of xFANCA-chr by immunoblot.

FIG. 5A and FIG. 5B are digital images of autoradiographs that show that xFANCA and xFANCD2 are not essential for DNA replication. Genomic DNA replication was monitored by 30 minutes pulses of $\alpha$-$^{32}$P-GTP. FIG. 5A is a digital image of autoradiograph showing nucleotide incorporation into replicating chromatin in extracts incubated with protein A beads bound to preimmune serum (xFANCA pre-immune depleted extracts) or extract incubated with protein A beads bound to anti-xFANCA antibodies (xFANCA depleted extracts). FIG. 5B is a digital image of an autoradiograph showing $^{32}$P incorporation into replicating chromatin in extracts incubated with protein A beads bound to preimmune serum (xFANCD2 pre-immune depleted extracts) or extract incubated with protein A beads bound to anti-xFANCD2 antibodies (xFANCD2 depleted extracts). FIG. 5C and FIG. 5D are bar graphs of the charted average (including error bars) of the incorporation of radiolabeled nucleotides, by band density from three identical replication assays (indicated) including the assays from FIGS. 5A and 5B. FIG. 5E and FIG. 5F are a digital images of autoradiographs that show depletion of xFANCA or xFANCD2 causes DNA breaks during normal replication. FIG. 5E is a digital image of an autoradiograph showing egg extracts that were treated with beads coupled to xFANCA-preimmune serum (lane 1) or beads coupled to anti-xFANCA serum (lane 2). FIG. 5F is a digital image of an autoradiograph showing extracts that were treated with either beads coupled to xFANCD2-preimmune serum (lane 1) or beads coupled to anti-xFANCD2 serum (lane 2). Sperm chromatin was added to treated extracts, and after 120 minutes TUNEL assays were performed. Samples were subjected to agarose gel electrophoresis and phosphorimaging.

FIGS. 7A and 7B are digital images of immunoblots. FIG. 7A is a digital image of an immunoblot that shows that two of the compounds that scored positive in the initial screen (CS-A3 and CS-E3) were tested for dose dependent response at the indicated concentrations. Compound CS-A3 displayed a moderate inhibitory effect on aFANCD2 activation. Compound E3 appears to be a potent inhibitor of FANCD2 activation. FIG. 7B is a digital image of an immunoblot that demonstrates compound NP-B11 stimulates the post-translational modification of xFANCM or inhibits the dephosphorylation of xFANCM. Compound NP-B11 is cantharidin.

FIGS. 8A-8B are a set of digital images of immunoblots demonstrating that monoubiquitination of xFANCD2 fails in the absence of xFANCA. FIG. 8A is a digital image of an immunoblot xFANCA was immunodepleted from *Xenopus* egg cell free extracts prior to addition of DNA. FIG. 8B is a digital image of an immunoblot showing that in the *Xenopus* egg cell free extracts cleared of xFANCA, xFANCD2 was not monoubiquitinated (second lane).

FIG. 9A is a digital image of an immunoblot showing the presence of dsDNA fragments triggers formation of an xFANCD2-L form. Double stranded DNA fragments generated by plasmid dsDNA digest were incubated in *Xenopus* egg cell free extracts for 30 min. 1 µl of egg extract containing either no DNA (Ø) or 200 ng/III dsDNA fragments was analyzed by immunoblot. xMre11 was used as positive control due to its known mobility shift response to dsDNA fragments (Costanzo et al., *Mol. Cell.* 8(1):137-47, 2001). FIG. 9B is a digital image of an immunoblot showing that the xFAND2-L form induced with dsDNA fragments represents is monoubiquitinated xFANCD2. His-tagged human ubiquitin was added to DNA-free extracts or extracts containing 200 ng/µl dsDNA fragments. Following incubation for 30 min, 1 ul of extract was analyzed for xFANCD2-L (lanes 1 and 2). His-tagged, monoubiquitinated proteins were reisolated using Ni-beads and analyzed for xFANCD2-L by immunoblot (lanes 3 and 4). FIG. 9C is a digital image of an immunoblot showing that xFANCD2-L is induced in the presence of linear and branched dsDNA. The DNA structures ssDNA$_{70}$, dsDNA$_{70}$, Y-DNA$_{70}$, and forkDNA$_{70}$ were incubated in *Xenopus* egg cell free extracts for 20 min and 1 ul of extract was analyzed for induction of xFANCD2-L or xMre11-PPP by immunoblot. For stabilization of xMre11-PPP, the phosphatase inhibitor tautomycin (T) was added to extracts where indicated.

FIG. 10A is a digital image of an immunoblot showing xFANCD2-L is recruited to DNA that triggers its activation. ssDNA$_{70}$ and forkDNA$_{70}$ structures coupled to magnetic beads were incubated in *Xenopus* egg cell free extracts for 20 min. Following incubation, 1 ul of extract was analyzed for induction of xFANCD2-L (lanes 1-3). Bead-DNA substrates were separated from the extract followed by analysis of bead-DNA (lanes 7-9) and remaining extract (lanes 4-6) for xFANCD2 and xFANCA by immunoblot. Empty beads were used as negative control (lanes 1, 4, and 7). FIG. 10B is a digital image of an immunoblot showing that xFANCD2-L associates with linear and branched dsDNA. Bead-coupled DNA structures ssDNA$_{70}$, dsDNA$_{70}$, Y-DNA$_{70}$, and forkDNA$_{70}$ were incubated in egg extracts for 20 min, reisolated, and analyzed for xFANCD2 and xFANCA by immunoblot. FIG. 10C is a digital image of an immunoblot showing that xFANCD2-L associates with a holliday junctions. Bead-coupled DNA structures HJ-DNA$_{68}$ and dsDNA$_{68}$ were incubated in egg extracts for 20 min, re-isolated, and analyzed for xFANCA and xFANCD2 by immunoblot. HJ-DNA$_{68}$: dsDNA$_{68}$ were used at molar ratios of 1:1 (compare lanes 1 and 2), 1:2 (compare lanes 1 and 3), or 1:3 (compare lanes 1 and 4). 1 ul of DNA-free extract was used as size control for xFANCD2-S (lane 5).

FIG. 11A and FIG. 11B are digital images of immunoblots demonstrating that formation of xFANCD2-L and xMre11-PPP in response to dsDNA fragments is FANCA-controlled. FIG. 11A is a digital image of an immunoblot showing xFANCA-depleted or mock-depleted *Xenopus* egg cell free extracts that were incubated with 200 ng/ul dsDNA fragments. Samples were taken at the indicated time points and analyzed for xFANCD2 or xMre11 by immunoblot. FIG. 11B is a digital image of an immunoblot showing *Xenopus* egg cell free extracts that were depleted of xFANCA, xFANCD2, xMre11 or mock-depleted, and incubated with dsDNA fragments for 30 min. 1 ul of extract was subsequently analyzed for xFANCA, xFANCD2, or xMre11 by immunoblot. FIG. 11C is a digital image of an immunoblot showing recruitment of xFANCD2-L to branched DNA is dependent on xFANCA but not xMre11 or the xATR/xATRIP complex. *Xenopus* egg cell free extracts were depleted of xFANCA (upper panel), xMre11 (middle panel), or xATRIP (lower panel). Mock-depleted extract was used as control in all depletion experiments (lanes 2 and 4). Depleted extracts were incubated with bead-coupled ssDNA$_{70}$ (lanes 1 and 2) or bead-coupled forkDNA70 (lanes 3 and 4) for 30 min and analyzed for the indicated *Xenopus* proteins. 1 ul of DNA-free egg extract was used as a control for *Xenopus* protein size.

FIG. 12A is a digital image of an immunoblot showing *Xenopus* egg cell free extracts that were incubated for 30 min with 45 ng/ul of (a) circular plasmid dsDNA, lane 1 (containing no dsDNA ends/plasmid molecule), (b) linearized plasmid dsDNA, lane 3 (containing 2 dsDNA ends per plasmid molecule), or (c) HaeIII-digested plasmid dsDNA, lane 2 (containing 28 dsDNA ends per plasmid molecule). DNA-free extract incubated for 30 min served as a negative control (lane 4). Following incubation, 1 ul of extract was analyzed for xFANCD2 and xMre11 by immunoblot. FIG. 12B is a digital image of an immunoblot demonstrating that high concentrations of circular plasmid dsDNA induce xMre11-PPP. *Xenopus* egg cell free extracts were incubated for 30 min with increasing concentrations of circular plasmid dsDNA as indicated. Following incubation, 1 ul of extract was analyzed for xFANCD2 and xMre11 by immunoblot. DNA-free extract incubated for 30 min served as a negative control (lane 5). FIG. 12C is a digital image of an immunoblot showing that linearized plasmid dsDNA induces xFANCD2-L earlier and at lower DNA concentrations than fragmented plasmid dsDNA. *Xenopus* egg cell free extracts were incubated with three different concentrations of linearized or fragmented plasmid dsDNA (50 ug/ul, lanes 2, 5, 8; 25 ng/ul, lanes 3, 6, 9; 10 ng/ul, lanes 4, 7). Aliquots were taken at 5 min, 15 min, and 25 min and 1 ul was analyzed for xFANCD2 and xMre11 by immunoblot. 1 ul of DNA-free extract incubated for 25 min was used as a negative control (lane 1).

FIG. 13A and FIG. 13B are digital images of immunoblots showing circular dsDNA induces xFANCD2-L in a replication-independent manner. FIG. 13A is a digital image of an immunoblot showing *Xenopus* egg cell free extracts that were incubated with 160 ng/ul circular plasmid dsDNA for 30 min in the presence or absence of the replication initiation inhibitor geminin. Efficiency of replication inhibition was measured by performing a parallel replication assay using an aliquot of the geminin-treated extract (smaller panel in figure FIG. 13A). FIG. 13B is a digital image of an immunoblot showing that non-activated, M-phase egg extracts or $CaCl_2$-activated, S-phase egg extracts were incubated with 160 ng/ul circular plasmid dsDNA. Extract aliquots (1 ul) were taken at the indicated time points and analyzed for xFANCD2 and xMre11. FIG. 13C and FIG. 13D are digital images of immunoblots that show circular dsDNA induces xFANCD2-L in a checkpoint-independent manner. FIG. 13C is a digital image of an immunoblot showing *Xenopus* egg cell free extracts that were incubated with 160 ng/ul circular plasmid dsDNA for 30 min in the presence or absence of the checkpoint kinase inhibitor caffeine. Where indicated, extracts were supplemented with the phosphatase inhibitor, tautomycin, to stabilize xMre11-PPP. Following incubation, 1 ul of extract was analyzed for xFANCD2 and xMre11 by immunoblot. DNA-free extract was used as a size control for xFANCD2-S and xMre11 (lane 1). FIG. 13D is a digital image of an immunoblot showing *Xenopus* egg cell free extracts that were incubated either with bead-coupled anti-xATRIP antibody or with bead-coupled pre-immune serum and incubated with 200 ng/ul circular plasmid dsDNA. Aliquots were taken at different time points and assayed for xFANCD2 by immunoblot. 1 ul of DNA-free extract was used as a size control for xFANCD2-S (lane 5). FIG. 13E is a digital image of an immunoblot showing that circular dsDNA induces xFANCD2-L in a topoisomerase II α-dependent manner. *Xenopus* egg cell free extracts containing 200 ng/ul of circular plasmid dsDNA were incubated with etoposide (30 uM, lane 2; 60 uM, lane 3) or ICRF-193 (150 uM, lane 4; 300 uM, lane 5). *Xenopus* egg cell free extracts containing 200 ng/ul of circular plasmid dsDNA but not topoisomerase IIα inhibitor were used as positive control and DNA-free extracts were used as negative control for induction of xFANCD2-L.

FIGS. 15A-15B are a sequence alignment demonstrating the homology between *Xenopus* and human FANCM. *Xenopus tropicalis* (xFANCM) (SEQ ID NO:12) was aligned with full length human FANCM (SEQ ID NO: 13). Amino acid identity is indicated by (*); similar amino acids are indicated by (.).

FIGS. 16A-16C are a sequence alignment demonstrating the homology between *Xenopus* and human FANCD2. Full length *Xenopus* FANCD2 (xFANCD2) (SEQ ID NO:1) was aligned with full length human FANCD2 (hFANCD2) (SEQ ID NO:2) using MacVector 7.1.1 software. Amino acid identity is indicated by dark shading; similar amino acids are indicated by light shading. Two known critical residues, S222 and K561, (denoted by arrows) are conserved between human and *Xenopus* FANCD2.

SEQUENCE LISTING

Figure 1:
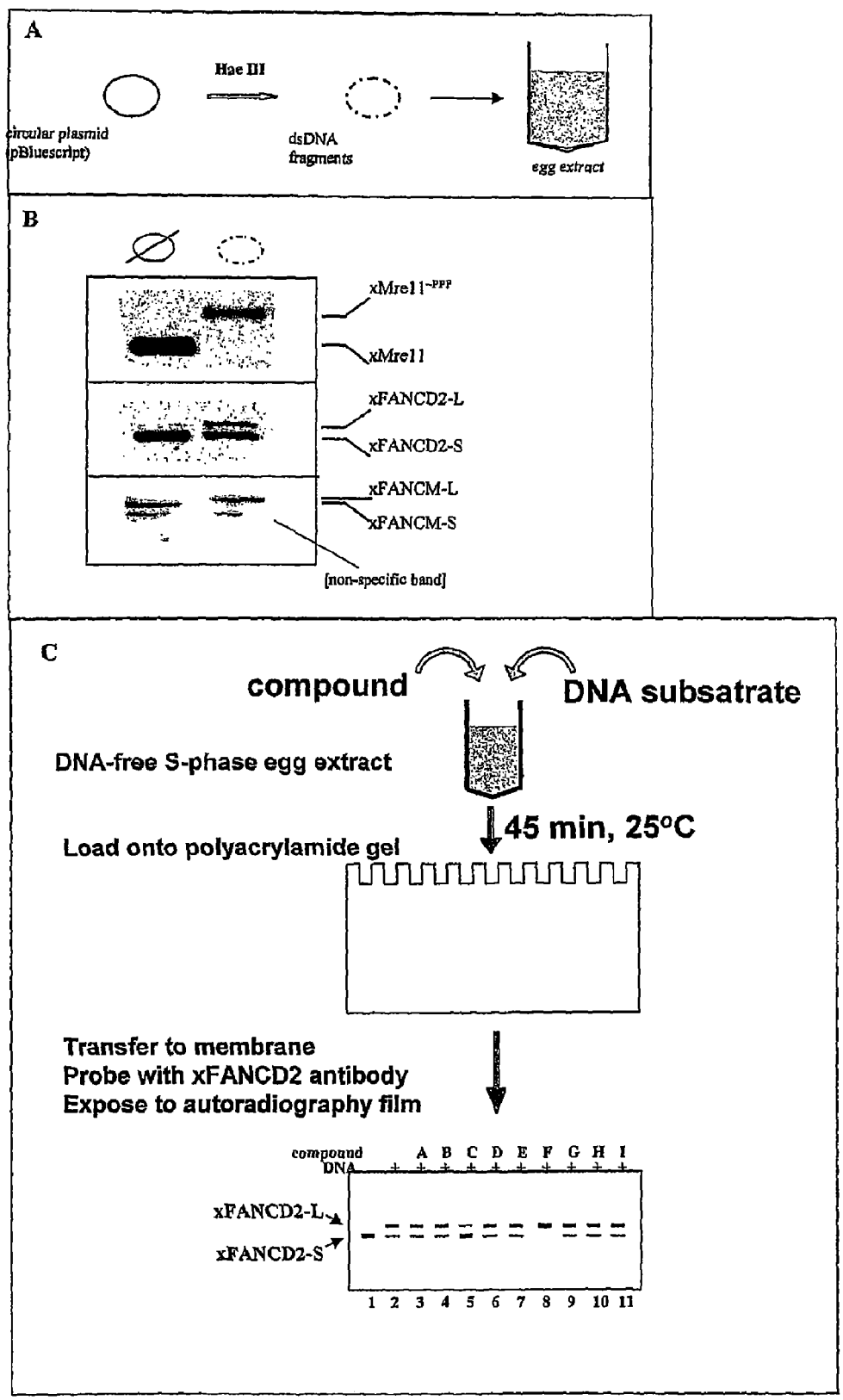
FIGS. 1A-1C are a schematic representation of stimulation of the Fanconi anemia pathway by digested plasmid DNA, a digital image of an immunoblot and a schematic depiction of the screening assay.

The nucleic and amino acid sequences listed in the accompanying sequence listing are shown using standard letter abbreviations for nucleotide bases, and one letter code for amino acids, as defined in 37 C.F.R.1.822. Only one strand of each nucleic acid sequence is shown, but the complementary strand is understood as included by any reference to the displayed strand.

SEQ ID NO:1 is an amino acid sequence of FANCD2 from *Xenopus laevis* (GENBANK® accession number AAV35204).

SEQ ID NO:2 is an amino acid sequence of FANCD2 from *Homo sapiens* (GENBANK® accession number AAL05980).

SEQ ID NO:3-11 are synthetic nucleic acids.

SEQ ID NO:12 is an amino acid sequence of FANCM from *Xenopus tropicalis*.

SEQ ID NO:13 is an amino acid sequence of FANCM from *Homo sapiens*

DETAILED DESCRIPTION OF SEVERAL EMBODIMENTS

*Xenopus* egg cell free extracts that are of use to detect agents for the treatment of cancer and Fanconi anemia are disclosed herein. Also disclosed are methods for detecting an agent of use in treating cancer or Fanconi anemia that utilize a *Xenopus* egg cell free extracts.

I. Terms

Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All publications, patent applications, patents, and other references mentioned herein are incorporated by reference in their entirety. In case of conflict, the present specification, including explanations of terms, will control. In addition, all the materials, methods, and examples are illustrative and not intended to be limiting. In order to facilitate review of the various embodiments of the disclosure, the following explanations of specific terms are provided:

Antibody: A polypeptide ligand comprising at least a light chain or heavy chain immunoglobulin variable region which specifically binds an epitope of an antigen, such as one of the *Xenopus* Fanconi anemia polypeptides, protein, or a fragment thereof. The term "specifically binds" refers to, with respect to an antigen such as a *Xenopus* Fanconi anemia polypeptide, the preferential association of an antibody or other ligand, in whole or part, with a *Xenopus* Fanconi anemia polypeptide. A specific binding agent binds substantially only to a defined target, such as the *Xenopus* Fanconi anemia target polypeptide. Thus, in one example an xFANCD2 specific binding agent is an agent that binds substantially to an xFANCD2 polypeptide. For example, if an agent, such as an antibody, specifically binds FANCD2 it does not specifically bind other proteins including other Fanconi anemia proteins. In another example an xFANCM specific binding agent is an agent that binds substantially to an xFANCM polypeptide, but not another *Xenopus* Fanconi anemia polypeptide. It is, of course, recognized that a minor degree of non-specific interaction may occur between a molecule, such as a specific binding agent, and a non-target polypeptide. Nevertheless, specific binding can be distinguished as mediated through specific recognition of the antigen. Although selectively reactive antibodies bind antigen, they can do so with low affinity. Specific binding typically results in greater than 2-fold, such as greater than 5-fold, greater than 10-fold, or greater than 100-fold increase in amount of bound antibody or other ligand (per unit time) to a *Xenopus* Fanconi anemia polypeptide, such as xFANCD2 as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Binding or aggregation: The process by which proteins and/or nucleic acid form a complex. "Binding" or "aggregation" of Fanconi anemia proteins DNA implies that the Fanconi anemia proteins and DNA form a complex that can be isolated.

Bone marrow transplant (BMT): A medical procedure in the field of hematology and oncology that involves transplantation of hematopoietic stem cells (HSC). It is most often performed for people with diseases of the blood or bone marrow, or certain types of cancer and Fanconi anemia. There are two major types of bone marrow transplantation. Autologous bone marrow transplantation involves isolation of HSC from a patient, storage of the stem cells in a freezer, medical treatment of the patient that destroys stem cells remaining in the body, and return of the patient's own stored stem cells to their body. Allogeneic bone marrow transplantation involves two people, one is the (normal) donor and one is the (patient) recipient. Allogeneic HSC donors must have a tissue (HLA) type that matches the recipient and, in addition, the recipient requires immunosuppressive medications. Allogeneic transplant donors may be related (usually a sibling) or unrelated volunteers.

Cancer: A malignant disease characterized by the abnormal growth and differentiation of cells. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubes (e.g., carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and non-melanoma). Several specific examples of cancers are cervical cancer, pancreatic cancer, lung cancer and ovarian cancer.

Cell cycle: The cycle of events in a eukaryotic cell from one cell division to the next that includes interphase, mitosis, and usually cell division. The cell cycle is divided into several phases. The G0-phase is a period in the cell cycle where cells exist in a quiescent state. The G1 (gap)-phase is the first growth phase. S-phase (synthesis) is the period during which the DNA is replicated. G2-phase is the second growth phase. M (mitosis)-phase is the phase in which actual division of the chromatin and the cell into two daughter cells occurs. In a normal cell cycle the G1 precedes S, which is followed by G2, which is followed by M phase thus returning to G1. In *Xenopus* egg cell extracts the progression of the cell cycle that occurs in vivo proceeds without the pauses, or gaps, in the G-phases. Following release by $CaCl_2$ synchronized M-phase cell extracts proceed to synchronized S-phase, bypassing the gap phases. "Checkpoints" are times during the cell cycle that monitor the cell for DNA damage and failure to perform critical processes. Checkpoints can block progression through the phases of the cell cycle if certain conditions are not met. For example, there is a checkpoint which monitors DNA replication and keeps cells from proceeding to mitosis before DNA replication is completed. Similarly, the spindle checkpoint blocks the transition from metaphase to anaphase within mitosis if not all chromosomes are attached to the mitotic spindle. The "G1 Checkpoint" prevents damaged DNA from being replicated and is believed to be controlled by the ATM and ATR kinases. The "S-phase" checkpoint monitors cell cycle progression and decreases the rate of DNA synthesis following DNA damage.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is a radioactive compound. Chemotherapeutic agents are described for example in Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology 2nd ed.*, 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (eds): *The Cancer Chemotherapy Handbook*, 4th ed. St. Louis, Mosby-Year Book, 1993. Combination chemotherapy is the administration of more than one agent to treat cancer.

Chromosome: A very long continuous piece of DNA, containing many genes, regulatory elements, and other intervening nucleotide sequences and supporting protein structures (histones). During cell division, chromosomes become highly condensed distinct bodies within the nuclei of cells. During the metaphase stage of cell division chromosomes can be visualized by staining metaphase spreads and the use of light microscopy. A chromosome, by definition, has exactly one centromere. During metaphase, following replication, the chromosome appears as two sister chromatids joined at the centromere. "Chromosomal breakage" describes a phenomenon in which the chromosomes of a subject have broken into smaller fragments. Typically breaks are defined as achromatic areas greater than one chromatid in width. "Chromatin" consists of a complex of DNA and histones in eukaryotic cells.

Contacting: Placement in direct physical association. Includes both in solid and liquid form. Contacting can occur in vitro with isolated cells or cell free extracts, such as extracts from *Xenopus* eggs, or in vivo by administering to a subject. "Administrating" to a subject includes topical, parenteral, oral, intravenous, intramuscular, sub-cutaneous, inhalational, nasal, or intra-articular administration, among others.

Control: A reference standard. A control can be a known value indicative of basal activation or a control *Xenopus* egg cell free extract not treated with an agent. A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%.

Degenerate variant and conservative variant: A polynucleotide encoding a polypeptide or an antibody that includes a sequence that is degenerate as a result of the genetic code. For example, a polynucleotide encoding a *Xenopus* Fanconi anemia polypeptide includes a sequence that is degenerate as a result of the genetic code. There are 20 natural amino acids, most of which are specified by more than one codon. Therefore, all degenerate nucleotide sequences are included as long as the amino acid sequence of the *Xenopus* Fanconi anemia polypeptide encoded by the nucleotide sequence is unchanged. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Such nucleic acid variations are "silent variations," which are one species of conservative variations. Each nucleic acid sequence herein that encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity.

DNA replication: The process of copying a double-stranded DNA strand, prior to cell division (in eukaryotes, during the S phase of interphase, preceding mitosis and meiosis). The two resulting double strands are identical and each of them consists of one original and one newly synthesized strand.

Double-strand breaks (DSB): Double-strand breaks (DSBs) are a serious form of DNA damage leading to problems for transcription, replication, and chromosome segregation. DSBs are caused by a variety of sources including exogenous agents such as ionizing radiation and certain genotoxic chemicals, endogenously generated reactive oxygen species, replication of single-stranded DNA breaks, and mechanical stress on the chromosomes. DSBs differ from most other types of DNA lesions in that they affect both strands of the DNA duplex and therefore prevent use of the complementary strand as a template for repair. Failure to repair these defects can result in chromosomal instabilities leading to dysregulated gene expression and carcinogenesis. To counteract the detrimental effects of DSBs, cells have evolved two distinct pathways of DSB repair, homologous recombination (HR) and non-homologous end joining (NHEJ). The Fanconi anemia pathway is one of the component pathways involved in DSB Repair. HR-directed repair corrects DSB defects in an error-free manner using a mechanism that retrieves genetic information from a homologous, undamaged DNA molecule. The majority of HR-based repair takes place in late S- and G2-phases of the cell cycle when an undamaged sister chromatid is available for use as repair template.

Fanconi anemia: Fanconi anemia (FA) is a recessive inherited anemia that leads to bone marrow failure (aplastic anemia). Complementation studies using human FA patient cell lines have shown that there are at least twelve FA genes (-A, -B, -C, -D1 (BRCA2), -D2, -E, -F, -G, -I, -J, -L, and -M). FANCI has not been cloned. Mutations in the known genes account for almost all of the cases of Fanconi anemia. Mutations in FANCA, FANCC, and FANCG are the most common and account for approximately 85% of the FA patients. Mutations in FANCD1, FANCD2, FANCE, FANCF, and FANCL account for 10% of the FA patients, while mutations in FANCB, FANCI, and FANCJ account for less than 5% of FA patients.

FA occurs equally in males and females and is found in all ethnic groups. Though considered primarily a blood disease, FA features highly variable developmental defects and cancer susceptibility. Many patients develop acute myelogenous leukemia (AML) at an early age. FA patients are extremely likely to develop head and neck, gynecological, and/or gastrointestinal squamous cell carcinomas. Defects in DNA damage response and DNA repair may be underlying causes of the developmental defects, bone marrow failure and cancer susceptibility in FA. Typical treatments for Fanconi anemia include androgen therapy, administration of growth factors and bone marrow transplant.

The "Fanconi anemia Pathway" refers to the functional relationship that exists between the known Fanconi anemia proteins (FANCA, -B, -C, -D1, -D2, -E, -F, -G, -I, -J, -L, and -M) in DAN replication and nuclear responses to DNA cross-links. Eight of these proteins (FANCA, FANCB, FANCC, FANCE, FANCF, FANCG, FANCL, and FANCM) form a complex that localizes to the nucleus and is termed the FA nuclear core complex. The remaining three proteins (FANCD2, FANCD1, and FANCJ) are collectively referred to as the FA non-nuclear core (NNC) component. Disruption of activity of the FA NNC component leads to an inability of cells to repair DNA damage, such as that induced by a DNA crosslinking agent. "FANCD2" is a protein component of the Fanconi anemia pathway identified from the Fanconi anemia complementation group D. In normal cells, FANCD2 is activated by monoubiquitination and/or phosphorylation in response to DNA damage. Unless indicated, FANCD2 refers to FANCD2 from any organism while "xFANCD2" refers to *Xenopus* FANCD2. In *Xenopus* FANCD2 (xFANCD2) the sites of monoubiquitination and phosphorylation are K563 (K561 in human) and S224 (S222 in human), respectively.

"FANCA" is a protein component of the Fanconi anemia pathway identified from the Fanconi anemia complementation group A. FANCA is part of a large protein complex that includes the Bloom syndrome protein BLM, TopoIIa, BLAP75, replication protein A (RPA), DNA mismatch repair protein MLH1, FAAP100, and several FA proteins including FANCB, FANCC, FANCE, FANCF, FANCG, FANCL, and FANCM (Meetei et al., *Mol. Cell. Biol.* 23(10):3417-26, 2003). The FA proteins form a tight complex that is believed to be responsible for the monoubiquitination of FANCD2 in response to DNA damage or simulated DNA damage. Unless indicated, FANCA refers to refers to FANCA from any organism (xFANCA is FANCA from *Xenopus*). "FANCM" is a protein component of the Fanconi anemia pathway identified from the Fanconi anemia complementation group M. Unless indicated, FANCM refers to FANCM from any species while "xFANCM" refers to *Xenopus* FANCM. In response to DNA damage, FANCM is phosphorylated.

Figure 16A:
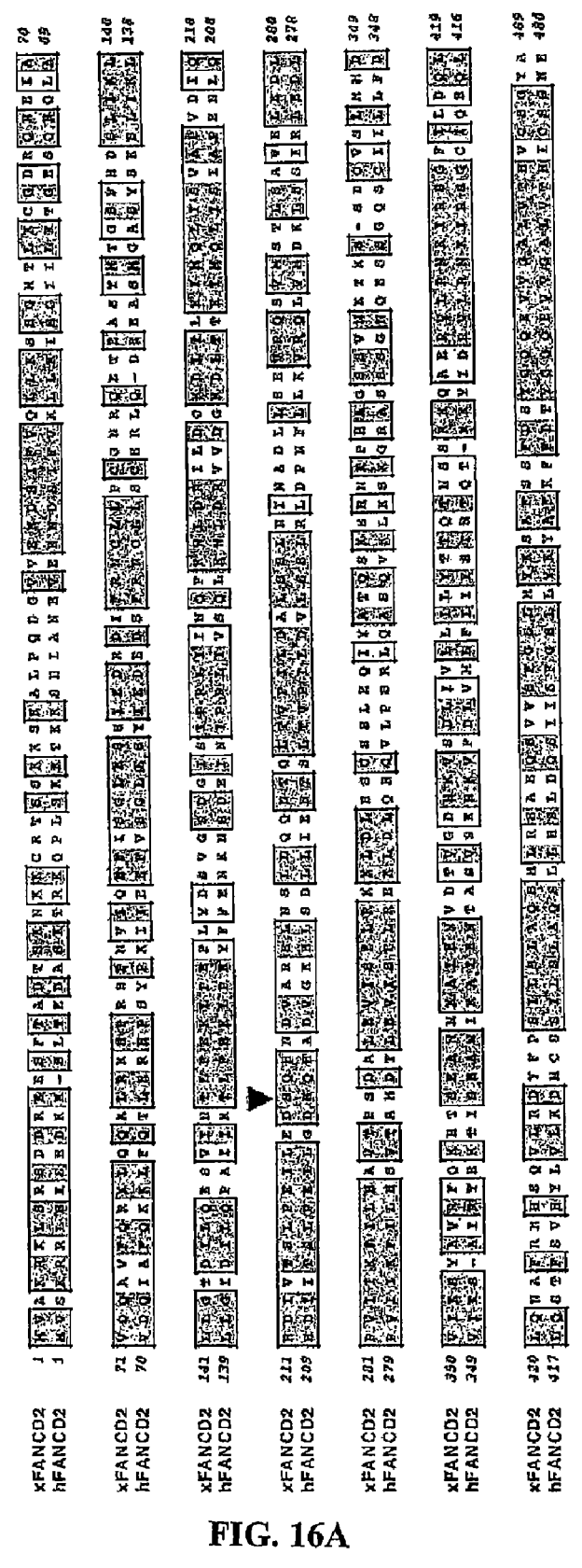
Figure 16B:
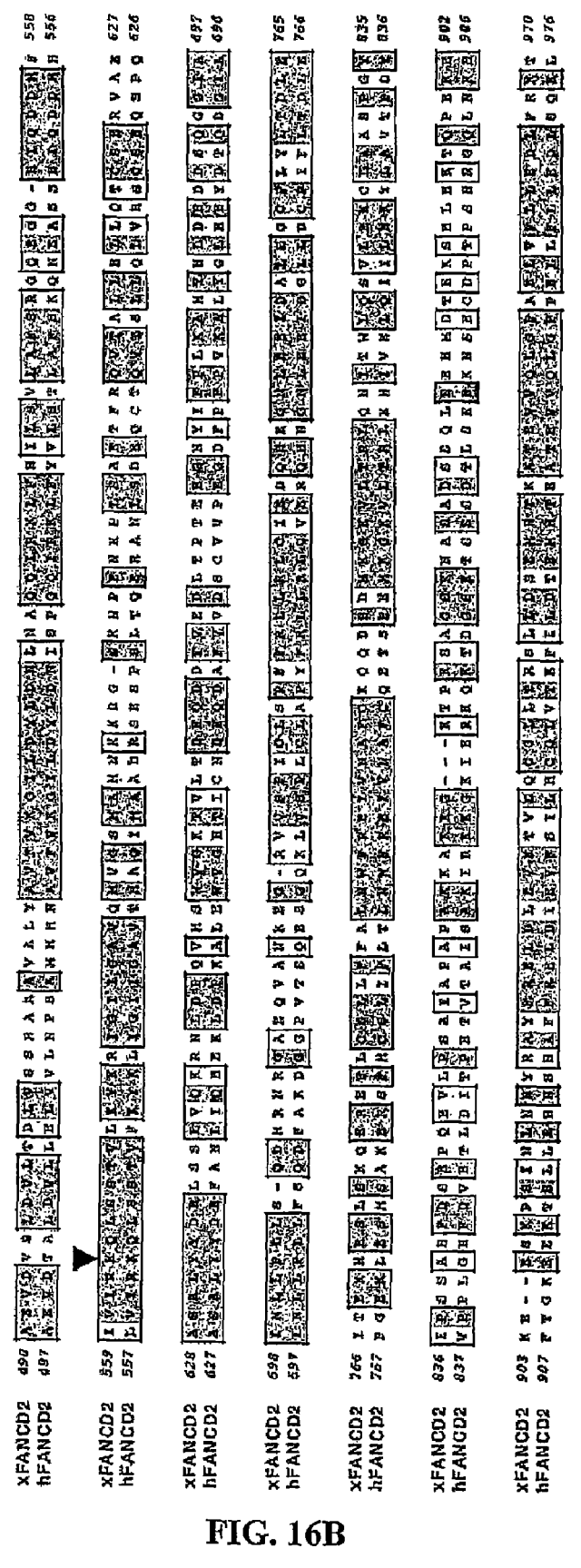

An exemplary nucleotide sequence of xFANCA can be found at NCBI accession number AY633664 (date of release Mar. 14, 2006). An exemplary nucleotide sequence of xFANCD2 can be found at NCBI accession number (date of release Mar. 14, 2006). An exemplary nucleotide sequence of *Xenopus* FANCL (xFANCL) can be found at NCBI accession number AY633666 (date of release Mar. 14, 2006). An exemplary nucleotide sequence of *Xenopus* FANCF (xFANCF) can be found at NCBI accession number AY547288 (date of release Sep. 13, 2004). An exemplary amino acid sequence of *Xenopus* FANCM (xFANCM) is shown in FIG. 16A-16B.

High throughput technique: Through a combination of modern robotics, data processing and control software, liquid handling devices, and sensitive detectors, high throughput techniques allows the rapid screening of potential pharmaceutical agents in a short period of time. Through this process one can rapidly identify active compounds, antibodies or genes which affect a particular biomolecular pathway, for example the *Xenopus* Fanconi anemia pathway.

Isolated: An "isolated" biological component (such as a protein, chromatin, sperm chromatin or nuclei) has been substantially separated or purified away from other biological components in the cell of the organism in which the component naturally occurs, i.e., extra-chromatin DNA and RNA, proteins and organelles. Chromatin and proteins that have been "isolated" include chromatin, sperm chromatin and proteins purified by standard purification methods. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination.

Label: A detectable compound or composition that is conjugated directly or indirectly to another molecule, such as a nucleic acid, antibody, or a protein, to facilitate detection or purification of that molecule. Specific, non-limiting examples of labels include fluorescent tags, enzymatic linkages, and radioactive isotopes.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA.

A "branched DNA" is a double stranded DNA structure made from 4 DNA strands. The first 2 strands have portions of complementary, such that the 3' portion of the first strand can be annealed to the 5' portion of the second strand. The first strand has a 5' portion that is not complementary to the 3' portion of the second strand. Thus the first and second strands have two branching "prongs" that do not anneal with each other, the 5' portion of the first strand and the 3' portion of the second strand, respectively. Two additional strands of DNA have sequence homology to the 5' portion of the first strand and the 3' portion of the second strand and can be annealed to the 5' portion of the first strand and the 3' portion of the second strand, respectively.

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide. For example, an xFANCD2 polynucleotide is a nucleic acid encoding an xFANCD2 polypeptide.

"Exogenous DNA" is DNA originating from a different species or individual. For example, DNA that is exogenous to a *Xenopus* egg cell free extract is DNA that does not originate from *Xenopus*, such as human DNA, plasmid DNA, synthetic DNA, or the like. "Endogenous DNA" is DNA that is from the organism. In one example, DNA endogenous to a *Xenopus* egg cell free extract is DNA that originated from the eggs from which the *Xenopus* egg cell free extracts were prepared.

"Fragmented plasmid DNA refers plasmid DNA that has been cut into small pieces of the original structure. Typically this is done to produce short segments of double stranded DNA, for example using a restriction enzyme. Plasmids, restriction enzymes and their use are well known in the art.

For sequence comparison of nucleic acid sequences and amino acids sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

Other example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (see the NCBI web site). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Therapeutically effective amount: The quantity of a chemical composition or sufficient to achieve a desired effect in a subject being treated. For instance, this can be the amount necessary to inhibit the progression of Fanconi anemia and/or cancer or to measurably alter outward symptoms of Fanconi anemia and/or cancer. When administered to a subject, a dosage will generally be used that will achieve target tissue concentrations that has been shown to achieve in vitro inhibition of Fanconi anemia and/or cancer or to measurably alter outward symptoms of Fanconi anemia and/or cancer.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (such as glycosylation, methylation, ubiquitination, phosphorylation, or the like). "Post-translational modification" is the chemical modification of a polypeptide after its translation, for example by monoubiquitination, glycosylation, methylation, phosphorylation, or the like. In one example, xFANCD2 is post-translationally modified by ubiquitination, and/or phosphorylation. In another example, xFANCM is post-translationally modified phosphorylation. Post-translational modification can lead to an apparent difference in molecular weight, for example a difference in molecular weight between post-translationally modified protein, such as a *Xenopus* Fanconi anemia protein and the same Fanconi anemia protein which is not post-translationally modified. This difference can be measured on the basis of a post-translationally modification dependent protein mobility shift, for example on a SDS-PAGE gel or by other methods such as mass spec. In one example, the protein is xFANCD2. Thus, post-translationally modified xFANCD2 and non-post-translationally modified xFANCD2 can be separated by apparent molecular weight. In another example, the protein is xFANCM. Thus, post-translationally modified xFANCM and non-post-translationally modified xFANCM can be separated by apparent molecular weight.

"Ubiquitin" is a small protein that is ubiquitous in eukaryotes. "Ubiquitination" (or "Ubiquitylation") refers to the post-translational modification of a protein by the covalent attachment (via an isopeptide bond) of one or more ubiquitin monomers. Monoubiquitination is the process in which a single ubiquitin peptide is bound to a substrate. Poly-ubiquitination is the process in which a chain of ubiquitin peptides are attached to a lysine on a substrate protein. Poly-ubiquitination most commonly results in the degradation of the substrate protein via the proteasome.

"Phosphorylation" is the addition of a phosphate to a protein, typically by a kinase. Measurable phosphorylation of a polypeptide, such as a protein can be quantified using well known assays. This can be done by measuring the incorporation of a radioactive isotope of phosphorous into a test protein, for example the incorporation of [$^{32}$P] from the γ phosphate of [γ-$^{32}$P]ATP, into a *Xenopus* Fanconi anemia protein, such as xFANCD2, or xFANCM among others. Phosphorylation also can be measured on the basis of a phosphorylation-dependent protein mobility shift, for example a phosphorylation dependent mobility shift of phosphorylated xFANCD2 or xFANCM.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

Synchronized: Cells or cell free extracts (such as *Xenopus* egg cell free extracts) that are in an identical phase of the cell cycle. For example M-phase synchronized cells are all in the M-phase of the cell cycle. Similarly, M-phase synchronized cells extracts (such as *Xenopus* egg cell extracts) are in the M-phase of the cell cycle.

Subject: Living multi-cellular vertebrate organisms, a category that includes both human and veterinary subjects, including human and non-human mammals.

Treating: Inhibiting the full development of a disease or condition, for example, in a subject who is at risk for a disease such as Fanconi anemia and/or cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

*Xenopus laevis*: A species of South African aquatic frog of the genus *Xenopus*. *Xenopus* eggs are eggs obtained from female *Xenopus* frogs. *Xenopus* eggs are initially surrounded by three jelly layers, J1, J2, and J3. These layers constitute part of the egg extracellular matrix. The jelly layers can be removed (de-jellied) by incubation in a cysteine containing solution.

*Xenopus* egg cell free extract, cell free extract, cell extract or extract: A solution made by the removal of the contents of a cell from the cellular context, such as the jelly and the outer membrane. Cell free extracts made from *Xenopus* eggs retain many of the features of an intact cell, including the machinery needed for replication, and the nuclear and cytosolic proteins of a cell, such as the *Xenopus* Fanconi anemia proteins. The *Xenopus* egg cell free extracts are treated to have the endogenous DNA removed, including DNA in the form of chromatin. In some embodiments, a cell free *Xenopus* egg extract includes additional media such as an energy mix.

II. Description of Several Embodiments

In normal cells, the Fanconi anemia pathway responds to DNA damage by activating several Fanconi anemia proteins by post-translational modification. As disclosed herein, at least two of these post-translational modifications were discovered to be conserved in *Xenopus* egg cell free extracts. In *Xenopus*, as in human cells, FANCD2 can be ubiquitinated on residue K563 (K561 in human) and phosphorylated on residue S224 (S221 in human). The interactions between core complex members xFANCA, xFANCF, xFANCG, and xFANCM are also conserved in Xenopus. xFANCD2, the downstream target of the Fanconi anemia pathway, is activated by post-translational modification during S-phase, producing the large form of xFANCD2 (xFANCD2-L). As disclosed herein, the non-ubiquitinated form of xFANCD2 (xFANCD2-S) was detected in egg extracts. The ubiquitinated large form of xFANCD2 (xFANCD2-L) was shown to be detectable in Xenopus egg cell free extracts after addition of DNA or in the presence of replicating chromatin. Also as disclosed herein, xFANCM was found to be post-translationally modified in Xenopus egg cell free extracts. These, and other, post-translational modifications of Fanconi anemia proteins can be used as qualitative and/or quantitative molecular readouts of the activation of the Fanconi anemia pathway in Xenopus egg cell free extracts. Thus, the identification of an intact Fanconi anemia pathway in Xenopus egg cell free extracts offers a previously unknown assay for studying the Fanconi anemia pathway. This assay is especially useful for screening for agents that affect the Fanconi anemia pathway. Agents identified using the disclosed methods are useful for the treatment of Fanconi anemia and cancer.

In addition, the Xenopus egg cell free extracts and methods provided herein offer several significant advantages for assessing the Fanconi anemia pathway over conventionally studied mammalian cells, such as human cells. One such advantage is that Xenopus eggs harbor large amounts of Fanconi anemia proteins in preparation for the rapid divisions that occur after fertilization. In contrast, in human cells, most of the Fanconi anemia pathway proteins are relatively scarce and large quantities of cells must be grown over long periods of time, adding both time and expense to the development of agents that affect the Fanconi anemia pathway. An additional advantage to the use of Xenopus egg extracts is that they can be initially synchronized within the cell cycle in an arrested M-phase state. These M-phase synchronized extracts can be released from M-phase by the addition of a chemical agent and allowed to proceed through S-phase carrying out one round of semi-conservative replication. Thus, the extracts provide the unique opportunity to determine the activity of the Xenopus Fanconi anemia pathway before, during, and after replication. With typical mammalian cell culture, the cells are at various stages of the cell cycle, and it is difficult to obtain large numbers of synchronized mammalian cells without affecting the replication machinery of these cells. A schematic of a non-limiting example of an assay is shown in FIG. 1A.

A. Methods of Identifying an Agent for the Treatment of Cancer or Fanconi Anemia Assays for Post Translational Modification of Fanconi Anemia Proteins This disclosure relates to methods for identifying agents that affect the Fanconi anemia pathway. The agents identified using these methods can be used in the treatment of cancer, and thus can be used for the treatment of cancer in a subject, such as a human subject. In addition, identified agents can be used for the treatment of Fanconi anemia. The disclosed methods are based on the discovery that the Fanconi anemia pathway is conserved in Xenopus egg cell free extracts. In several embodiments, Xenopus egg cell free extracts, from which endogenous DNA has been removed, are contacted with an agent of interest, such as a test agent. Exemplary methods are provided for producing the Xenopus egg cell free extracts described herein, although it is contemplated that any method that provides a Xenopus egg cell free extract that can replicate DNA can be used with the methods disclosed herein.

Following contact with the agent, the Xenopus Fanconi anemia polypeptide is detected. The amount of post-translationally modified Xenopus Fanconi anemia polypeptide in a Xenopus egg cell free extract can be compared to a control. In several embodiments, the control is a known value indicative of basal post-translational modification of a Xenopus Fanconi anemia polypeptide. In several embodiments, the control is a known value indicative of basal post-translational modification of a Xenopus Fanconi Anemia polypeptide in response to stimulation by DNA. In additional embodiments, the control is the amount of post-translationally modified Xenopus Fanconi anemia polypeptide in a Xenopus egg cell free extract that has not been treated with an agent.

A difference between the amount of post-translationally modified Xenopus Fanconi anemia polypeptide from a control indicates that the agent can be of use for treating cancer and/or Fanconi anemia. In some embodiments, the difference between post-translational modification of a Xenopus Fanconi anemia protein in a Xenopus egg cell free extract contacted with an agent relative to a control is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%. In some embodiments, the difference is a statistically significant difference. Thus, an agent can induce a statistically significant difference in the amount of the post-translationally modified Xenopus Fanconi anemia polypeptide in the cell extract contacted with the agent, as compared to the control such as a Xenopus egg cell free extract not contacted with the agent (such as an extract contracted with carrier alone).

In one embodiment, an agent that decreases the amount of the post-translationally modified Xenopus Fanconi anemia polypeptide as compared to a control is identified as being of use for treating cancer, such as cancers in the general population as well as cancers in subjects with Fanconi anemia. In some embodiments, a decrease in the amount of post-translational modification of a Xenopus Fanconi anemia protein in a Xenopus egg cell free extract is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease as compared to control. In additional embodiments, the decrease is a statistically significant decrease as compared to a control.

In another embodiment, an agent that increases the amount of the post-translationally modified Xenopus Fanconi anemia polypeptide as compared to a control is identified as being of use for treating Fanconi anemia. In some embodiments, an increase in the amount of post-translational modification of a Xenopus Fanconi anemia protein in a Xenopus egg cell free extract is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% increase as compared to control. In additional embodiments, the increase is a statistically significant increase as compared to a control.

In several embodiments, the effect of an agent on the amount of post-translationally modified Xenopus Fanconi anemia polypeptide is assessed in the presence of exogenous DNA. In some embodiments, the method includes adding isolated exogenous double stranded DNA with at least one double strand break to the *Xenopus* egg cell free extracts. In additional embodiments, the double-stranded DNA is branched DNA. The DNA can be DNA from any source, including, human DNA, non-human primate DNA, mammalian DNA, plasmid DNA or synthetic DNA. The DNA is exogenous to *Xenopus*. DNA for use in the methods disclosed herein can be either labeled or unlabelled.

In some examples, the method utilizes DNA including double strand breaks that are blunt ended, such that single stranded DNA over hangs are not present in the nucleic acid molecule. In additional examples, the exogenous double stranded DNA is between about 10 and about 500 nucleotides in length, such as about 10, about 20, about 30, about 40, about 50, about 60, about 70, about 80, about 90, about 100, about 120, about 140, about 160, about 180, about 200, about 250, about 300, about 350, about 400, about 450, and about 500 nucleotides in length. In further examples, the double stranded DNA is fragmented plasmid DNA, for example plasmid DNA that has been digested with an endonuclease. Endonucleases and plasmid DNA are well known to those of ordinary skill in the art and can be purchased, for example, from Invitrogen and/or New England Biolabs. Examples of endonucleases include, but are not limited to, HaeIII, AluI, BstUI, AfeI, EcoRI, KpnI, and Dra1. Examples of plasmids include, but are not limited to, pBR322 and pBluescript plasmid DNA.

DNA can also be produced synthetically using nucleic acids created with a DNA synthesizer. For example, double stranded DNA can be produced by annealing the nucleic acid molecule 5'-(dG)$_{40}$-(dA)$_{30}$-3' (SEQ ID NO:3) to the nucleic acid molecule 5'-(dT)$_{30}$-(dC)$_{40}$-3' (SEQ ID NO:4). In an additional example, branched double stranded DNA is assembled by annealing the nucleic acid molecule 5'-(dG)$_{40}$-(dA)$_{30}$-3' (SEQ ID NO:3), the nucleic acid molecule 5'-(dA)$_{30}$-(dC)$_{40}$-3' (SEQ ID NO:5), and two the nucleic acid molecules of (dT)$_{30}$ (SEQ ID NO:6). One of skill in the art will appreciate that these DNA molecules are exemplary only; additional molecule can be produced using repeats of A, G, C and T in any order.

In some circumstances, activation of the *Xenopus* Fanconi anemia pathway is stimulated by the addition of a DNA damaging agent. Thus, in some embodiments, the *Xenopus* egg cell free extracts are contacted with a DNA damaging agent such as a crosslinking agent include alkylating agents, for example mitomycin C (MMC) and diepoxybutane (DEB), although any agent that produces crosslinks in sufficient quantity can be used.

The *Xenopus* egg cell free extracts used for the disclosed methods are depleted of endogenous DNA and chromatin. In several examples, a *Xenopus* egg cell free extract is produced by removing the egg jelly, cellular debris and chromatin, for example using the method of Murray (*Methods Cell Biol.* 36:581-605, 1991). Media can be added that contains additional components, such as creatine phosphate, adenosine triphosphate (ATP), MgCl$_2$ cytochalasin B and PEFABLOC® (4-(2-aminoethyl)benzenesulfonylfluoride). It also may be advantageous to remove one or more *Xenopus* Fanconi anemia proteins from the cell free *Xenopus* egg extracts, for example by immunodepletion of a *Xenopus* Fanconi anemia protein. By way of example, it may be usefully to remove a component normally needed for activation of the Fanconi anemia pathway, such as xFANCA. Thus, the ability of an agent, such as a test agent, to activate the Fanconi anemia pathway in the absence of a functional pathway thus can be determined.

In some embodiments, the *Xenopus* egg cell free extracts are produced from *Xenopus* eggs arrested at a specific point in the cell cycle, such as synchronized in M-phase. In certain embodiments, the cell free extracts are released from M-phase arrested eggs, for example by the addition of a chemical agent such as CaCl$_2$. The *Xenopus* egg cell-free egg extract can be arrested at the end of S-phase following DNA replication. In one example, the *Xenopus* egg cell free egg extract is arrested at the end of S-phase by addition of cycloheximide to the cell extract (Murray, *Methods Cell Biol.* 36:581-605, 1991). Post-translationally modified *Xenopus* Fanconi anemia proteins such as xFANCD2 bind to double stranded DNA with double strand breaks in *Xenopus* egg cell free extracts that are arrested at the end of S-phase. Thus, in some embodiments it is advantageous to purify the exogenous DNA from the *Xenopus* egg cell free extracts and evaluate the amount of post-translationally modified *Xenopus* Fanconi anemia polypeptide bound to the exogenous DNA. Suitable methods for the isolation of DNA from *Xenopus* egg cell free extracts are described herein.

The presence of post-translationally modified *Xenopus* Fanconi anemia polypeptide can be determined using any method known to one of skill in the art. In several examples, the presence of post-translationally modified *Xenopus* Fanconi anemia polypeptide is determined using an antibody that specifically binds the polypeptide, such as a monoclonal or polyclonal antibody. In some embodiments, the antibody that specifically binds the post-translationally modified *Xenopus* Fanconi anemia polypeptide also binds the same *Xenopus* Fanconi anemia polypeptide that has not been post-translationally modified. In some embodiments, the antibody specifically binds only the post-translationally modified *Xenopus* Fanconi anemia protein, and does not bind the unmodified form of this polypeptide.

In some embodiments the post-translationally modified *Xenopus* Fanconi anemia protein is xFANCD2. In several examples, the post-translational modification is phosphorylation of xFANCD2. In additional examples, the post-translational modification is ubiquitination of xFANCD2, for example monoubiquitination of xFANCD2 (xFANCD2-L). The presence of post-translationally modified xFANCD2, such as ubiquitinated xFANCD2 can be determined using an antibody that specifically binds xFANCD2, such as a monoclonal or polyclonal antibody. In some embodiments, the antibody specifically binds the post-translationally modified form of xFANCD2, and does not bind the unmodified form of xFANCD2.

In some embodiments, the post-translationally modified *Xenopus* Fanconi anemia polypeptide is xFANCM. In several examples, the post-translational modification is phosphorylation of xFANCM. The presence of post-translationally modified xFANCM, such as phosphorylated xFANCM can be determined using an xFANCM antibody that specifically binds xFANCM, such as a monoclonal or polyclonal antibody. In some embodiments, the antibody is a monoclonal or polyclonal antibody that specifically binds the post-translationally modified form of xFANCM, such as the phosphorylated form of xFANCM.

The detection of phosphorylated protein is well known in the art and can be detected for example using stains specific for phosphorylated proteins in gels. Alternatively, antibodies specific to phosphorylated proteins can be made or commercially obtained. In some embodiments, phosphorylated xFANCD2 and/or phosphorylated xFANCM is detected. While not wanting to be bound by theory, it is believed that in response to DNA damage or simulated DNA damage, the γ phosphate of a nucleotide triphosphate, such as ATP is transferred to xFANCD2 and/or xFANCM. By addition of 7 phosphate labeled triphosphate, such as ATP, into the cell free extract, the presence of post-translationally modified xFANCD2 and/or xFANCM can be determined. In some embodiments, a γ phosphate labeled triphosphate, such as ATP is added to the *Xenopus* egg cell free extracts. Typically, the γ phosphate label is a radioisotope label, such as radioactive phosphorus ($^{32}P$), although any label that can be transferred via a kinase reaction is contemplated by this disclosure. By this methodology, the activation, degree of activation, and/or inhibition of the *Xenopus* Fanconi anemia pathway can be determined by incorporation of $^{32}P$ into xFANCD2 and/or xFANCM. It is understood that an agent such as a chemical agent, for example a drug, therapeutic, or potential therapeutic, can activate the *Xenopus* Fanconi anemia pathway, resulting in the incorporation of a phosphate, for example $^{32}P$, into xFANCD2 and/or xFANCM. It is further understood that an agent can have the opposite effect, for example by inhibiting the incorporation of phosphate into xFANCD2 and/or xFANCM, or by inhibiting the de-phosphorylation of xFANCD2 or xFANCM.

Post-translationally modified *Xenopus* Fanconi anemia proteins can have an apparent molecular weight greater than the same Fanconi anemia protein that has not been post-translationally modified. Thus, the apparent molecular weight can be used to distinguish post-translationally modified form of a *Xenopus* Fanconi anemia from the non-post-translationally modified *Xenopus* Fanconi anemia protein. Any method that allows the separation of polypeptides by molecular weight can be used. Examples of techniques for separation of polypeptides by molecular weight are well known in the art and include SDS-PAGE, gel filtration, mass spectrometry, and capillary electrophoresis amongst others.

Post-translationally modified xFANCD2 has an apparent molecular weight greater than the non-post-translationally modified form of xFANCD2. The molecular weight of monoubiquitinated xFANCD2 can readily be distinguished from unmodified xFANCD2, using, for example, SDS-PAGE. In some embodiments, the difference in apparent molecular weight between the post-translationally modified xFANCD2 and the non-post-translationally modified form of xFANCD2 is used to determine the relative amount of post-translationally xFANCD2 modified in a sample. For example, the two forms of xFANCD2 are separated and it is determined if the higher molecular weight form of xFANCD2 is present. In additional examples, the amount of monoubiquitinated xFANCD2 is determined.

Post-translationally modified xFANCM has an apparent molecular weight greater than the non-post-translationally modified form. The molecular weight of modified xFANCM can be distinguished from the modified form of xFANCM, such as using SDS-PAGE. The difference in apparent molecular weight can be used to distinguish the forms of xFANCM present in a sample. Thus, using molecular weight it can be determined if the post-translationally modified form of xFANCM is present in a sample. In some embodiments, the difference in apparent molecular weight between post-translationally modified form of xFANCM and non-post-translationally modified form of xFANCM is used to determine the relative amount of post-translationally modified xFANCM. For example, the two forms of xFANCM are separated and it is determined if the higher molecular weight form is present. In some embodiments, amount of phosphorylated xFANCM is determined.

The presence of post-translationally modified *Xenopus* Fanconi anemia protein can be determined with multiple specific binding agents, such as one, two, three, or more specific binding agents. Thus, the methods can utilize more than one antibody. For example, the presence of post-translationally modified xFANCD2 can be determined from the co-localization of an antibody that specifically binds xFANCD2, and an antibody that specifically binds *Xenopus* ubiquitin. *Xenopus* ubiquitin antibodies are well known in the art and are commercially available (for example from Abcam, catalog #ab 19247). The presence of post-translationally modified xFANCD2 can be determined from the co-localization of an antibody that specifically binds xFANCD2, and an antibody that specifically binds phosphoserine. Phosphoserine antibodies are well known in the art and are commercially available (for example from Invitrogen, catalog #61-8100). In some embodiments, one of the specific binding agents, such as an antibody specific for xFANCD2, is attached to a solid support, such as a multiwell plate (such as, a microtiter plate), bead, membrane or the like. In practice, microtiter plates may conveniently be utilized as the solid phase. The surfaces may be prepared in advance, stored, and shipped to another location(s).

However, antibody reactions also can be conducted in a liquid phase. In some examples, a first and second specific binding agent are used that are tagged with different detectable labels. In one example, the first and second tag interact when in proximity, such as when the specific binding agents are bound to the same target, for example a post-translationally modified *Xenopus* Fanconi anemia polypeptide such as post-translationally modified xFANCD2 or xFANCM (for example, due to resonance transfer). The relative proximity of the first and second tags is determined by measuring a change in the intrinsic fluorescence of the first or second tag. Commonly, the emission of the first tag is quenched by proximity of the second tag. After incubation, the presence or absence of a detectable tag emission is detected. The detected emission can be any of the following: an emission by the first tag, an emission by the second tag, and an emission resulting from a combination of the first and second tag. Typically, to detect the presence of post-translationally modified *Xenopus* Fanconi anemia protein, such as xFANCD2 or xFANCM, a change in the signal, due to binding of the two specific binding agents, is detected (for example, as an increase in fluorescence as a result of FRET, as an increase in quenching that leads to an decrease in signal from either or both of the tags, a change in signal color, and the like).

Many appropriate interactive tags are known. For example, fluorescent tags, dyes, enzymatic tags, and antibody tags are all appropriate. Examples of preferred interactive fluorescent tag pairs include terbium chelate and TRITC (tetramethylrhodamine isothiocyanate), europium cryptate and allophycocyanin and many others known to one of ordinary skill in the art. Similarly, two calorimetric tags can result in combinations that yield a third color, for example, a blue emission in proximity to a yellow emission provides an observed green emission.

With regard to preferred fluorescent pairs, there are a number of fluorophores that are known to quench one another. Fluorescence quenching is a bimolecular process that reduces the fluorescence quantum yield, typically without changing the fluorescence emission spectrum. Quenching can result from transient excited state interactions, (collisional quenching) or, for example, from the formation of nonfluorescent ground state species. Self quenching is the quenching of one fluorophore by another; it tends to occur when high concentrations, labeling densities, or proximity of tags occurs. Fluorescent resonance energy transfer (FRET) is a distance dependent excited state interaction in which emission of one fluorophore is coupled to the excitation of another that is in proximity (close enough for an observable change in emissions to occur). Some excited fluorophores interact to form excimers, which are excited state dimers that exhibit altered emission spectra (for example, phospholipid analogs with pyrene sn-2 acyl chains); see, Haugland (1996) Handbook of Fluorescent Probes and Research Chemicals, Published by Molecular Probes, Inc., Eugene, Oreg., for example at chapter 13).

In most uses, the first and second tags are different, in which case FRET can be detected by the appearance of sensitized fluorescence of the acceptor or by quenching of the donor fluorescence. When the first and second tags are the same, FRET is detected by the resulting fluorescence depolarization. In addition to quenching between fluorophores, individual fluorophores are also quenched by nitroxide-tagged molecules such as fatty acids. Spin tags such as nitroxides are also useful in the liquid phase assays describer herein. Liquid phase assays described herein can be performed in essentially any liquid phase container for example a container designed for high throughput screening such as a miltiwell microtiter dish (for example, 96 well, 384 well, etc).

Exemplary Test Agents

The methods disclosed herein are of use for identifying agents that can be used for treating Fanconi anemia and/or cancer. An "agent" is any substance or any combination of substances that is useful for achieving an end or result. The agents identified using the methods disclosed herein can be of use for affecting the post translational modification of a Fanconi anemia protein such as FANCD2 or FANCM, and can be of use for treating cancer or Fanconi anemia. Any agent that has potential (whether or not ultimately realized) to affect the post translational modification of *Xenopus* Fanconi anemia protein can be tested using the methods of this disclosure.

Exemplary agents include, but are not limited to, peptides such as, soluble peptides, including but not limited to members of random peptide libraries (see, e.g., Lam et al., *Nature,* 354:82-84, 1991; Houghten et al., *Nature,* 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell,* 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), small organic or inorganic molecules (such as, so-called natural products or members of chemical combinatorial libraries), molecular complexes (such as protein complexes), or nucleic acids.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.,* 37:487-493, 1991; Houghten et al., *Nature,* 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Natl. Acad. Sci. USA,* 90:6909-6913, 1993), vinylogous polypeptides (Hagihara et al., *J. Am. Chem. Soc.,* 114:6568, 1992), nonpeptidal peptidomimetics with glucose scaffolding (Hirschmann et al., *J. Am. Chem. Soc.,* 114:9217-9218, 1992), analogous organic syntheses of small compound libraries (Chen et al., *J. Am. Chem. Soc.,* 116:2661, 1994), oligocarbamates (Cho et al., *Science,* 261: 1303, 1003), and/or peptidyl phosphonates (Campbell et al., *J. Org. Chem.,* 59:658, 1994), nucleic acid libraries (see Sambrook et al. *Molecular Cloning, A Laboratory Manual,* Cold Springs Harbor Press, N.Y., 1989; Ausubel et al., *Current Protocols in Molecular Biology*, Green Publishing Associates and Wiley Interscience, N.Y., 1989), peptide nucleic acid libraries (see, e.g., U.S. Pat. No. 5,539,083), antibody libraries (see, e.g., Vaughn et al., *Nat. Biotechnol.,* 14:309-314, 1996; PCT App. No. PCT/US96/10287), carbohydrate libraries (see, e.g., Liang et al., *Science,* 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produce in a variety of manners including, but not limited to, spatially arrayed multipin peptide synthesis (Geysen, et al., *Proc. Natl. Acad. Sci.,* 81(13):3998-4002, 1984), "tea bag" peptide synthesis (Houghten, *Proc. Natl. Acad. Sci.,* 82(15): 5131-5135, 1985), phage display (Scott and Smith, *Science,* 249:386-390, 1990), spot or disc synthesis (Dittrich et al., *Bioorg. Med. Chem. Lett.,* 8(17):2351-2356, 1998), or split and mix solid phase synthesis on beads (Furka et al., *Int. J. Pept. Protein Res.,* 37(6):487-493, 1991; Lam et al., *Chem. Rev.,* 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one convenient embodiment, high throughput screening methods involve providing a combinatorial chemical or peptide library containing a large number of potential therapeutic compounds. Such combinatorial libraries are then screened in one or more assays as described herein to identify those library members (particularly chemical species or subclasses) that display a desired characteristic activity (such as, activation of the *Xenopus* Fanconi anemia pathway, by increasing the relative amount of post-translational modified Fanconi anemia protein. In one example an agent of use is identified that increases the amount of ubiquitinated xFANCD2 relative to non-ubiquitinated xFANCD2. In another example an agent of use is identified that inhibits the *Xenopus* Fanconi anemia pathway, for example by decreasing the relative amount of the post-translational modified xFANCD2. In a further example, and agent of use is identified that increases the amount of ubiquitinated xFANCD2 relative to non-ubiquitinated xFANCD2).

The compounds identified using the methods disclosed herein can serve as conventional "lead compounds" or can themselves be used as potential or actual therapeutics. In some instances, pools of candidate agents may be identify and further screened to determine which individual or subpools of agents in the collective have a desired activity.

In several embodiments, agents identified by the methods disclosed herein are useful in sensitizing tumors, for example tumors resistant to typical chemotherapeutic agents (such as DNA crosslinking agents, for example DNA alkylating agents) to these DNA damaging agents by inhibiting the cells of a tumor to repair DNA damage via the Fanconi anemia pathway. For example an agent that inhibits the Fanconi anemia pathway (for example be inhibiting the post-translational modification of Fanconi anemia proteins) would not allow the Fanconi anemia pathway to repair damage caused by a DNA crosslinking agents, thus the tumor would be rendered sensitive to DNA crosslinking agents.

B. Therapeutic Compounds, Formulations and Treatments

This disclosure further relates to methods for treating a subject with cancer. As disclosed herein, the disclosed methods have identified several compounds that decrease the post-translational modification of *Xenopus* Fanconi anemia proteins (such as FANCD2 and/or FANCM). The compounds and derivatives thereof are particularly useful for treating cancer. The methods of treating cancer include administering a therapeutically effective amount of an agent identified as one that decreases the post-translational modification of a Fanconi anemia protein (such as FACND2 or FANCM). Thus in some embodiments, the pharmaceutical compositions containing an agent that decreases the post-translational modification of a Fanconi anemia protein (such as FANCD2 and/or FANCM) is administered to a subject, such as a subject with cancer. In some embodiments, the subject is a human subject. It is also contemplated that the compositions can be administered with a typical treatment for cancer, such as in conjunction with a therapeutically effective amount chemotherapeutic agent.

In some examples, a subject is selected for treatment with an anti-tumor agent that decreases the post-translational modification of a Fanconi anemia protein, such as FANCD2 and/or FANCM. In one such example, a subject is selected who has a tumor that has an increase in the amount of post-translationally modified Fanconi anemia protein. Such a subject can be treated with an agent identified by the methods disclosed herein that decreases the amount of post-translationally modified protein in the tumor. In another example, a subject is selected who has a tumor that has a decrease in the amount of post-translationally modified Fanconi anemia protein. Such a subject can be treated with an agent identified by the methods disclosed herein that increases the amount of post-translationally modified protein in the tumor.

This disclosure further relates to methods for treating a subject with Fanconi anemia. As disclosed herein, the disclosed methods have identified several compounds that increase the post-translational modification of *Xenopus* Fanconi anemia proteins (such as FANCD2 and/or FANCM). The compounds and derivatives thereof are particularly useful for treating Fanconi anemia. The methods of treating Fanconi anemia include administering a therapeutically effective amount of an agent identified as one that increases the post-translational modification of a Fanconi anemia protein (such as FACND2 or FANCM).

In some embodiments, the subject is a human subject. It is also contemplated that the compositions can be administered with a typical treatment for Fanconi anemia, such as in conjunction with a therapeutically effective amount of an androgen, a growth factor, or a combination thereof. In some embodiments, a subject is treated for Fanconi anemia with a bone marrow transplant. Thus in some embodiments, the pharmaceutical compositions containing a agent that increases the post-translational modification of a Fanconi Anemia protein (such as FANCD2 and/or FANCM) is administered to a subject, such as a human subject, that has had or will have a bone marrow transplant.

Therapeutic compound(s) can be administered directly to a subject for example a human subject. Administration is by any of the routes normally used for introducing a compound into ultimate contact with the tissue to be treated. The compounds are administered in any suitable manner, optionally with pharmaceutically acceptable carrier(s). Suitable methods of administering therapeutic compounds are available and well known to those of skill in the art, and, although more than one route can be used to administer a particular composition, a particular route can often provide a more immediate and more effective reaction than another route.

When the agent is to be used as a pharmaceutical, the agent is placed in a form suitable for therapeutic administration. The agent may, for example, be included in a pharmaceutically acceptable carrier such as excipients and additives or auxiliaries, and administered to a subject. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, nontoxic excipients, including salts, preservatives, buffers and the like, as described, for instance, in *Remington's Pharmaceutical Sciences,* 15th ed., Easton: Mack Publishing Co., 1405-1412, 1461-1487, 1975, and *The National Formulary XIV.,* 14th ed., Washington: American Pharmaceutical Association, 1975). The pH and exact concentration of the various components of the pharmaceutical composition are adjusted according to routine skills in the art. See *Goodman and Gilman The Pharmacological Basis for Therapeutics,* 7th ed.

The pharmaceutical compositions are in general administered topically, intravenously, orally or parenterally or as implants. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampoule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science,* 249:1527-1533, 1990, which is incorporated herein by reference.

For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units, and also by multiple administrations of subdivided doses at specific intervals.

A therapeutically effective dose is the quantity of a compound according to the disclosure necessary to prevent, to cure or at least partially ameliorate the symptoms of a disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman: the Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference. Effectiveness of the dosage can be monitored by any method.

C. Kits and High Throughput Systems

This disclosure also provides kits for identifying agents that affect the post translational modification of Fanconi anemia proteins. The kits include *Xenopus* egg cell free extracts and double stranded DNA that is between 10 and 500 nucleotides in length and contains double strand breaks. The kits may further include additional components such as instructional materials and additional reagents (for example specific binding agents, such as antibodies) radio nucleotides (such as $^{32}$P-ATP) or the like). The kits may also include additional components to facilitate the particular application for which the kit is designed (for example microtiter plates). Thus, for example, the kit may additionally contain means of detecting a label (such as enzyme substrates for enzymatic labels, filter sets to detect fluorescent labels, appropriate secondary labels such as a secondary antibody, or the like). Such kits and appropriate contents are well known to those of skill in the art. The instructional materials may be written, in an electronic form (such as a computer diskette or compact disk) or may be visual (such as video files).

This disclosure also provides integrated systems for high-throughput screening of agents for an effect on the *Xenopus* Fanconi anemia pathway, for example by affecting the post-translational modification of Fanconi anemia proteins, such as xFANCD2 and/or xFANCM. The systems typically include a robotic armature that transfers fluid from a source to a destination, a controller that controls the robotic armature, a tag detector, a data storage unit that records tag detection, and an assay component such as a microtiter dish comprising a well having a reaction mixture for example a *Xenopus* egg extract.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous assays of *Xenopus* egg extracts, for example the assay the effect of one or more agents on the *Xenopus* Fanconi anemia pathway.

Optional, optical images can viewed (and, if desired, recorded for future analysis) by a camera or other recording device (for example, a photodiode and data storage device) are optionally further processed in any of the embodiments herein, such as by digitalizing, storing, and analyzing the image on a computer. A variety of commercially available peripheral equipment and software is available for digitizing, storing and analyzing a digitized video or digitized optical image, e.g., using PC (Intelx86 or Pentium chip-compatible DOS™, OS2™ WINDOWS™, WINDOWS NT™ or WINDOWS95™ based computers), MACINTOSH™, or UNIX based (for example, a SUN™, a SGI™, or other work station) computers.

The following examples are provided to illustrate certain particular features and/or embodiments. These examples should not be construed to limit the invention to the particular features or embodiments described.

EXAMPLES

Example 1

General Materials and Methods

This example describes exemplary procedures and material used in the following examples.

Antibodies: Generation of anti-human FANCD2 rabbit polyclonal antisera (#3686) was described previously (Holzel et al., *J. Pathol.* 201:198-203, 2003). Anti-xFANCD2 (#4368) polyclonal rabbit antibodies were raised against an equal mix of three KLH bound xFANCD2 peptides corresponding to amino acids 1-18, 890-908, and 1425-1443. The antisera were affinity purified against the three non-KLH bound peptides immobilized on an AminoLink Plus column (Pierce) according to manufacturer's instructions. Anti-xFANCA (#1771) and anti-xFANCF (#1398) polyclonal rabbit antibodies were raised against a chimeric protein containing an N-terminal glutathione S-transferase (GST) tag (GST/pD-EST 15) with a C-terminal region of xFANCA (amino acids 1205-1383) or full-length xFANCF (amino acids 1-340) and purified from bacteria as previously described (Waisfisz et al., *Proc. Natl. Acad. Sci. U.S.A.* 96:10320-10325, 1999.). Affinity purification columns were made with a chimeric HIS-xFANCA 1205-1383, and HIS-xFANCF 1-340 (HIS/pDEST 17), purified as described in the QIAEXPERESSIONIST™ protocol (Qiagen) and immobilized on an AMINOLINK PLUS™ column.

Preparation of *Xenopus* egg extracts: Extracts were prepared from *Xenopus* eggs according to the method of Murray (Murray, *Methods Cell Biol.* 36:581-605, 1991). In brief, eggs were de-jellied in 2% cysteine, pH 7.8, washed three times in XB buffer (10 mM KCl, 1 mM $MgCl_2$, 100 nM $CaCl_2$, 10 mM HEPES, 5 mM ethylene glycol tetraacetic acid (EGTA), 1.75% w/v sucrose, pH 7.8) and washed three times in CSF-XB buffer (5 mM EGTA, 2 mM $MgCl_2$). Eggs were crushed by low speed centrifugation (10,000 g, 10 minutes) and the cytoplasmic fraction was cleared by centrifugation (16,000 g, 20 minutes) after the addition of energy mix (15 mM creatine phosphate, 2 mM ATP, 2 mM $MgCl_2$), cytochalasin B (10 μg/ml), cycloheximide (100 μg/ml), and PEFABLOC™ (4-(2-aminoethyl)benzenesulfonylfluoride) (100 μg/ml). In some of the examples described herein, the extracts were released from M to S phase by the addition of $CaCl_2$ to a final concentration of 0.4 mM. In some examples, the released extracts were incubated for 20 minutes at 23° C. Where indicated, mitomycin C (5-150 μM) and caffeine (4 mM), Tautomycin (3 uM), etoposide (30 or 60 uM), and ICRF-193 (150 and 300 uM) were added to S-phase extracts immediately prior to the addition of DNA substrates or sperm chromatin and incubated for the time indicated; aphidicolin (50 ng/1 μl), was added at the time points indicated. For complete inhibition of replication initiation, recombinant *Xenopus* geminin was added to S-phase extracts and incubated at 23° C. for 15 minutes.

Preparation of nuclei and chromatin fractions: At given time points, identical aliquots (50-100 μl) of *Xenopus* egg extract containing 1000 pronuclei (sperm heads)/μl were each diluted in nuclear isolation buffer (40 mM HEPES, 100 mM KCl, 20 mM $MgCl_2$) or chromatin isolation buffer (40 mM HEPES, 100 mM KCl, 20 mM $MgCl_2$, 0.2% Triton X-100) and purified through a 30% (w/v) sucrose cushion. Samples were centrifuged for 20 minutes at 6000 g and the nuclear and chromatin pellets, respectively, were analyzed by SDS-PAGE and immunoblot.

DNA Replication Assay: Replication of sperm chromatin in S-phase egg extracts was monitored as described by Costanzo et al. (Costanzo et al., *Mol. Cell.* 8:137-147, 2001). Briefly, sperm chromatin was added to S-phase extracts at 1000 pronuclei/µl. Reaction aliquots were pulse labeled with α-$^{32}$P-dGTP (Amersham) at time windows of 0-30 minutes, 30-60 minutes, 60-90 minutes, and 90-120 minutes at 23° C. Reactions were stopped with 1% SDS, 40 mM ethylenediaminetetraacetic acid (EDTA) (pH 7.8) and digested with proteinase K (1 mg/ml) at 37° C. for 1 h. DNA was extracted with phenol/chloroform and electrophoresed on a 1% agarose gel.

Immunodepletion: To immunodeplete selected proteins from S phase extracts, 200 µl of pre-swelled and washed (50% slurry in phospho buffered saline (PBS)) sepharose 4B beads (Amersham) were rotated overnight at 4° C. with 500 µl of PBS and 100 µl of xFANCD2 (rabbit #68), xFANCA (rabbit #71) affinity purified antisera, anti-xATRIP, or the corresponding pre-immune sera. The beads were pelleted from solution by centrifugation at 2500 rpm for 10 minutes at 4° C. and washed three times in XB buffer. 100 µl of extract was added to the beads. The extract/bead mix was rotated for two rounds at 4° C. for 40 minutes.

TUNEL Assay: 50 µl of xFANCA, xFANCD2 or pre-immune depleted S-phase egg extracts were incubated with 10,000 pronuclei/µl for 120 minutes at 23° C. The TUNEL assay was performed as previously described by Costanzo et al. (Costanzo et al., *Mol. Cell.* 8:137-47, 2001).

Immunoblotting: Protein samples were separated on 3-8% Tris-acetate gels or 4-12% NUPAGE® Bis-Tris gels (Invitrogen) and transferred to Immobilon P membranes (Millipore). After blocking in 5% milk for 1 h, membranes were incubated with the following primary antibodies: anti-hFANCD2 (1:300), xFANCA (1:300), or xFANCF (1:300), xATM (81) (1:1000), xTOP3 (1:1000), hORC2 (1:1500), hRPA70 (1:3000), and hPCNA (Santa Cruz, 1:1000). Horseradish peroxidase (BRP)-conjugated rabbit or mouse secondary (Jackson labs) was used (1:10,000). Protein bands were visualized using an ECL PLUS™ system (Amersham).

Plasmid-derived DNA substrates: Circular supercoiled pBluescript plasmid DNA (pBSKS, 2961 bp) was prepared from growing *E. coli* cultures using a QIAFILTER™ Plasmid Maxi Kit (Qiagen). Circular plasmid DNA was linearized by endonucleotlytic digest using Not 1 (Fermentas) or fragmented by endonucleolytic digest using HaeIII (Roche), creating 14 DNA fragments of different sizes (ranging from 11 bp to 476 bp). Linearized and fragmented DNA was purified using a PCR purification kit (Qiagen).

Oligonucleotide-derived substrates: The oligonucleotide 5'-(dG)$_{40}$-(dA)$_{30}$-3' (SEQ ID NO:3) (also referred to as ssDNA$_{70}$) was annealed to oligonucleotide 5'-(dT)$_{30}$-(dC)$_{40}$-3' (SEQ ID NO:4) to generate a double stranded DNA fragment (referred to as dsDNA$_{70}$). Oligonucleotides 5'-(dG)$_{40}$-(dA)$_{30}$-3' (SEQ ID NO:3) and 5'-(dA)$_{30}$-(dC)$_{40}$-3' (SEQ ID NO:5) were annealed to form Y-shaped structured DNA (referred to as Y-DNA$_{70}$) as previously described. The oligonucleotide (dT)$_{30}$ (SEQ ID NO:6) was annealed with this Y-shaped DNA to yield fork-structured DNA (referred to as forkDNA$_{70}$). Oligonucleotides 5'-ggttgacgttctagtgtgaccg-caatacggataagggctgagcacgccgacgaacatac-3' (SEQ ID NO:7) (HJ-strand 1), 5'-gtatgttcgtcggcgtgctcagc-ccftatcccagaatgcaccaacagttcctcaagatagagactc-3' (SEQ ID NO:8) (HJ-strand 2), 5'-gagtctctatcttgaggaactgttggtg-cattctgggataagggcactatggctccactgatgtcgtaagcatcc-3' (SEQ ID NO:9) (HJ-strand 3), and 5'-ggatgcftacgacatcagtggagccat-agtgcccttatccgtattgcggtcacactagaacgtcaacc-3'(SEQ ID NO:10) (HJ-strand 4) were annealed to form a Holliday junction structure (referred to as HJ-DNA$_{68}$, [134 bp]). HJ-strand 4 was annealed to 5'-ggttgacgttctagtgtgaccg-caatacggataagggcactatggctccactgatgtcgtaagcatcc-3'(SEQ ID NO:11) (HJ'-strand 5) to generate a linear double stranded dsDNA fragment (referred to as dsDNA$_{68}$ [68 bp]) with sequence similarity to the Holliday junction structure sequence.

For annealing, 1 µl of each oligonucleotide (200 pmol/µl) was mixed, the volume was adjusted to 10 µl with elution (EB) buffer (10 mM Tris-HCl, pH 8.5), and mixed with 10 µl of 2× annealing buffer (20 mM Tris-HCl, pH 8.0/2 mM EDTA/0.4 M NaCl). Annealing was performed by heating at 95° C. for 2 minutes, followed by incubation at 65° C. for 10 minutes, 37° C. for 10 minutes, and 22° C. for 10 minutes. Annealed HJ-DNA$_{68}$ and dsDNA$_{68}$ structures were purified by electrophoresis through a 4% polyacrylamide gel. DNA structures were excised from the gel and eluted into 50 ul of EB buffer using the QIAEX™ gel extraction kit (Qiagen).

Labeling of HJ-DNA$_{68}$ and dsDNA$_{68}$ structures was achieved by adding γ-$^{32}$P-ATP to the 5' end of HJ-strands 3 and 5, respectively, using T4 polynucleotide kinase prior to the annealing reaction.

Isolation of Proteins Bound to Magnetic Beads Containing Oligonucleotides: Streptavidin-conjugated magnetic beads (Dynal, Inc.) containing biotinylated ssDNA70, dsDNA70, Y-shaped DNA70, forkDNA70, dsDNA68 or HJ-DNA68 were incubated for 35 minutes in inter-phase egg extract. The biotin group was attached to the 3'-end of 5'-(dG)$_{40}$-(dA)$_{30}$-3' (SEQ ID NO:3) (in ssDNA$_{70}$, dsDNA$_{70}$, Y-DNA$_{70}$ and forkDNA$_{70}$ structures), the 3'-end of HJ strand 3 (in HJ-DNA$_{68}$) or the 3' end of HJ-strand 5 (in dsDNA$_{68}$) (see above). Following incubation in egg extracts, DNA-coupled magnetic beads were washed five times with XB buffer by collection with a magnetic rack.

Example 2

Conservation of the FA Pathway in *Xenopus laevis*

This example shows the sequence conservation between FANCD2 from *Xenopus* and *Homo sapiens*.

Figure 16C:
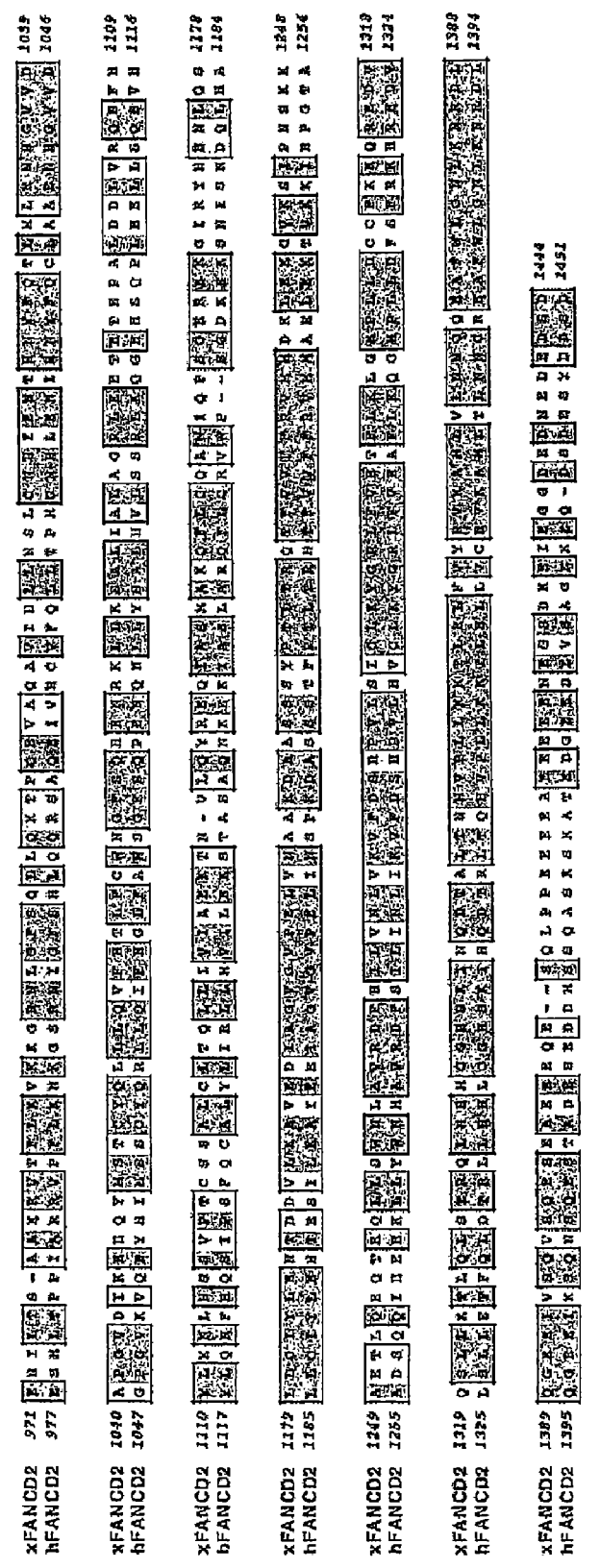

*Xenopus* homologs of several human FA genes were identified. The down-stream effector of the FA pathway in *Xenopus* (xFANCD2) is 70% homologous to the human FANCD2 and includes both the monoubiquitination site K561 (K563 in *Xenopus*) and the phosphorylation site S222 (S224 in *Xenopus*) (see FIG. 16). The conservation of the interactions between FA core complex members, and the DNA damage induced appearance of FANCD2-L occur in *Xenopus* cells and egg extracts, indicating that the FA pathway is conserved in *Xenopus*.

Example 3 xFA Proteins Associate with Chromatin in a Replication Initiation-Dependent Manner

Figure 2:
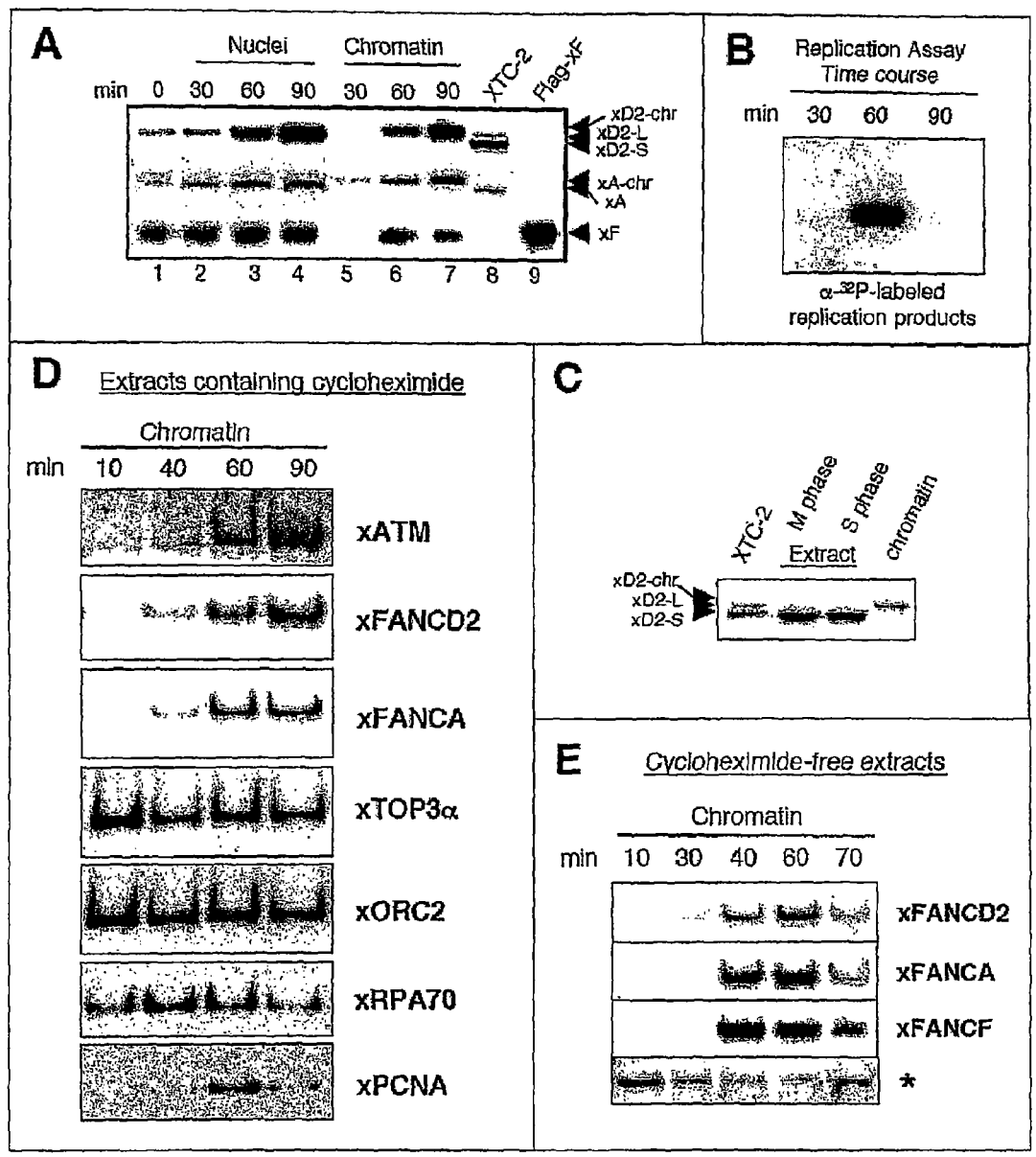
FIGS. 2A-2E are a set of digital images of immunoblots demonstrating that xFA proteins accumulate in nuclei and associate with chromatin in a replication-dependent manner.

*Xenopus* egg extracts were initially arrested at the end of meiosis ("M-phase extract") and contain only negligible amounts of DNA. The extracts were released into S-phase in tight synchrony by chemical activation. When sperm chromatin is added to S-phase extracts, the DNA decondenses and a nuclear membrane forms (20 minutes), followed by one round of semi-conservative chromosomal replication. Following addition of sperm chromatin nuclei and chromatin fractions were re-isolated at time points before, during, and after replication, and assayed for the presence of xFANCA, xFANCF, and xFANCD2. These proteins accumulated in the newly formed nuclei and associated with chromatin during replication (FIG. 2A). Typically this occurs between 30-60 minutes (FIG. 2B) (Murray, Methods Cell Biol. 36:581-605, 1991). A slow mobility form of xFANCD2 (xFANCD2-L) was predominant in whole nuclei (FIG. 2A, lanes 1 to 4), as well as in the nuclear chromatin fractions (FIG. 2A, lanes 5 to 7), at the indicated time points. These extracts were precisely synchronized throughout S-phase and replication of added sperm chromatin starts shortly after nuclear membrane formation, thus it is likely that xFANCD2-S is converted to its modified form (FANCD2-L) immediately upon nuclear import and then recruited to replicating chromatin. Only the small isoform of xFANCD2 was detected in M-phase and S-phase extracts (FIG. 2C), where only negligible amounts of DNA are present, consistent with previous evidence that chromatin binding is associated with monoubiquitination of FANCD2 (Montes et al., Blood 105:1003-1009, 2005; Wang et al., Mol. Cell. Biol. 24:5850-5862, 2004). Chromatin bound FA proteins are labeled with the suffix "-chr" in the text to provide a frame of reference because egg extracts and nuclear chromatin re-isolated from egg extracts typically contain only a single isoform of xFANCD2. Xenopus egg cell free extracts have a form comparable to FANCD2-S in cellular extracts, while chromatin replicated in egg extracts contains FANCD2-chr, comparable to FANCD2-L on chromatin isolated from cells. The mobility changes for FANCD2-chr and FANCA-chr compared with chromatin-bound counterparts in cell extracts was likely due to large amounts of chromatin and protein in the egg extract samples (FIG. 2A, compare lanes 7 and 8).

Unlike other DNA replication proteins such as xRPA70 or xPCNA, the xFA proteins stay associated with chromatin once the bulk of replication is completed (FIG. 2D, lane 90). Interestingly, the chromatin binding pattern of the checkpoint signaling kinase xATM, which monitors origin firing during normal replication, closely resembles the temporal binding pattern of both xFANCA and xFANCD2. To further investigate the observed chromatin association pattern of xFA proteins *Xenopus* egg cell free extracts prepared in the absence of cycloheximide were used. In classically prepared *Xenopus* egg extracts, cycloheximide blocks accumulation of cyclin B, which is required for the transition from S- to M-phase. Thus, in the presence of cycloheximide, extracts are halted in a G2-like state after DNA replication (FIG. 2D), whereas absence of cycloheximide allows the extracts to exit S-phase. In cycloheximide-free extracts, xFA proteins dissociated from chromatin once replication is over (FIG. 2E). Thus, the release of xFA proteins from chromatin was not triggered by the completion of replicative DNA synthesis alone but occurs only when extracts were allowed to exit S-phase. Accumulating evidence suggests that FA proteins function in the repair of specific DNA lesions that are encountered during transit through S phase (compare FIG. 2D and FIG. 2E).

Figure 3:
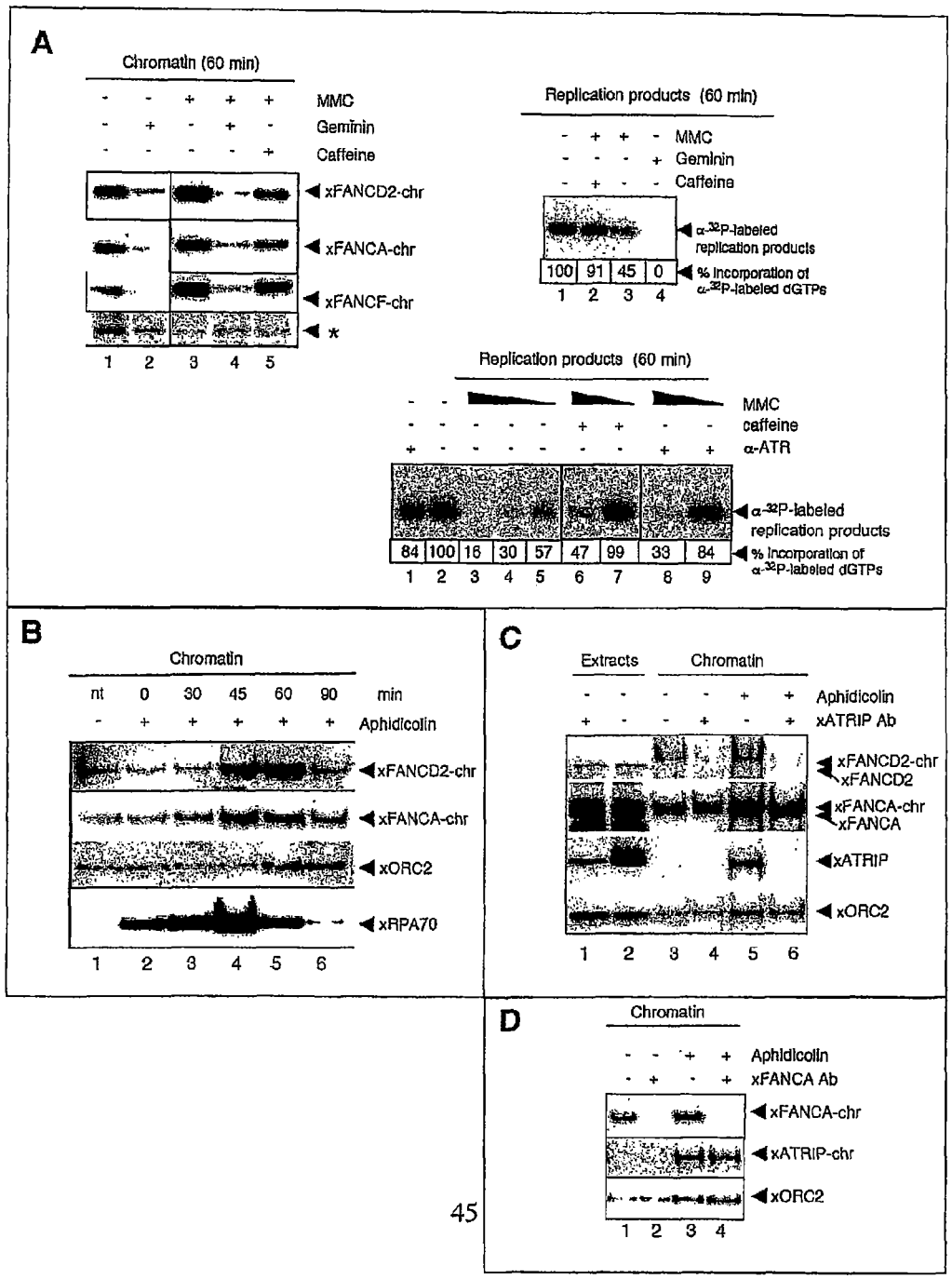
FIGS. 3A-3D are a set of digital images of immunoblots and autoradiographs demonstrating chromatin recruitment of xFA proteins in response to replication fork stalling and checkpoint activation.

To determine if xFA proteins bind to chromatin in a replication-dependent manner, replication initiation was blocked by the addition of geminin to S-phase egg extracts. Geminin prevents assembly of pre-replication complexes and thus inhibits replication initiation, but does not affect chromosome decondensation or nuclear membrane formation. As shown in FIG. 3A, top left, accumulation of xFA core complex proteins and xFANCD2 on chromatin (compare lanes 1 and 2) was drastically inhibited in the presence of geminin, demonstrating that recruitment of FA proteins to chromatin occurs in a strictly replication initiation-dependent manner. Previous reports show S-phase and DNA damage-dependent chromatin association of several FA proteins. However, whether chromatin assembly of the FA proteins was directly associated with the replication process has not been evaluated.

Example 4

Recruitment of FA Proteins to Chromatin During Disrupted Replication

The hallmark of Fanconi cells is hypersensitivity to DNA interstrand crosslinking agents such as MMC. As shown in FIG. 3A, top left, chromatin binding of xFANCA, xFANCF, and xFANCD2 increased in the presence of MMC (compare lanes 1 and 3), consistent with fractionation and immunofluorescence data for FA proteins in asynchronously dividing human cells (Meetei et al., Cell Cycle 3:179-181, 2004; Qiao et al., J. Biol. Chem. 276:23391-23396, 2001). Addition of caffeine, an inhibitor of the major checkpoint kinases, ATM and ATR (Sarkaria, Methods Mol. Med. 85:49-56, 2003), reversed the MMC-induced recruitment of xFA proteins to chromatin, indicating that xFA chromatin binding following MMC-treatment was part of a checkpoint controlled by one of the caffeine-sensitive kinases ATM or ATR (FIG. 3A, top left, compare lanes 1 and 5). Importantly, even in the presence of MMC, extracts failed to support chromatin recruitment of xFA proteins when replication initiation was blocked with geminin (FIG. 3A, top left, compare lanes 3 and 4). Replication in these extracts was monitored in matched aliquots by measuring incorporation of radiolabeled nucleotides into the nascent DNA strand. FIG. 3A, top right, the replication assay demonstrated that replication occurred (lane 1), was reduced by exposure to MMC (lane 3), and was rescued by addition of caffeine (lane 2). As expected, no incorporation was detected in the presence of geminin (lane 4). Taken together these data indicated that chromatin binding of xFA proteins was specifically triggered by DNA lesions that are encountered during DNA replication. The finding that caffeine restored wild type-like incorporation of nucleotides during replication in MMC-treated extracts suggests that replication inhibition induced by MMC was due to activation of an S-phase checkpoint, a response that allows cells to repair damage before they proceed to the next cell division, thus preventing the transmission of mutations (Bartek and Lukas, Curr. Opin. Cell Biol. 13:738-747, 2001; Canman, Curr. Biol. 13:R488-R490, 2003; Nyberg, Annu. Rev. Genet. 36:617-656, 2002; Pasero et al., Cell Cycle 2:568-572, 2003). To further explore the effect of MMC on replication, it was determined whether the reduction of replication products occurred in an MMC dose-dependent manner. As shown in FIG. 3A, bottom, DNA replication was significantly blocked at high concentrations of MMC (150 µM) (lane 3) and could not be rescued by caffeine (lane 6). In contrast, at lower MMC concentrations, replication was less inhibited (50 µM, lane 4; 5 µM, lane 5) and could be rescued in the presence of caffeine (lane 7).

To determine if the MMC-induced replication block was under control of the major replication checkpoint kinase, ATR, a neutralizing anti-xATR antibody was added to *Xenopus* egg extracts to specifically block the xATR kinase function (FIG. 3A, bottom, lanes 8 and 9), thereby preventing phosphorylation of the chk 1 protein that is required for activation of the S-phase checkpoint (Lupardus et al., Genes Dev. 16:2327-2332, 2002). Comparable to the effect observed in the presence of caffeine, inhibition of xATR did not rescue the very strong replication block in high MMC-concentrations (lane 7), however, at lower MMC-concentrations, reduction of replication products was restored back to wild-type levels when xATR was blocked. Thus, at lower doses the MMC-induced reduction in incorporation of nucleotides during replication was due to activation of an S-phase checkpoint that depends on xATR and results in an increase in xFA chromatin binding.

To determine the influence of fork stalling during DNA replication on recruitment of FA proteins to chromatin aphidicolin was added to replicating extracts. Aphidicolin treatment blocks replicative polymerases while helicases continue to unwind the DNA helix, thereby generating long single-stranded DNA (ssDNA) stretches (Pacek and Walter, *EMBO J.* 23:3667-3676, 2004; Shechter et al., *Nat. Cell Biol.* 6:648-655, 2004; Walter and Newport, *Mol. Cell* 5:617-627, 2000). As shown in FIG. 3B, addition of aphidicolin to replicating extracts resulted in increased chromatin association of xFA proteins as well as the ssDNA binding protein xRPA. Interestingly, whereas chromatin binding of xRPA increased significantly when aphidicolin was added before or during ongoing replication, recruitment of xFA proteins to chromatin increased only when aphidicolin was added during ongoing replication at 45 minutes (midreplication) and 60 minutes (late replication) (compare lane 1 with lanes 4 and 5). In contrast, when aphidicolin was added to extracts before the onset of replication (0 minutes or 30 minutes; compare lane 1 with lanes 2 and 3) or after replication was finished (90 minutes, compare lane 1 with lane 6), chromatin binding of xFA proteins did not increase. It is also important to note that under these conditions, aphidicolin does not result in detectable DNA DSBs (Li, et al., *J. Cell Biol.* 165:801-812, 2004). These results indicate that the xFA proteins are recruited when the moving replication fork encounters sites of DNA damage. In agreement, treatment of extracts with an inhibitor of replicative DNA polymerases, aphidicolin, also resulted in increased recruitment of xFA proteins to chromatin. Aphidicolin treatment leads to the generation of ssDNA regions due to uncoupling of the replicative helicase from the DNA polymerase. These ssDNA regions are generated regardless of whether aphidicolin was added to the egg extract before or during ongoing replication (as monitored by comparing chromatin-bound levels of the ssDNA-binding protein, xRPA). Interestingly, increased binding of xFA proteins to chromatin was only triggered when aphidicolin is added during the ongoing replication process, suggesting that the generation of ssDNA alone might not be sufficient for recruitment of the xFA proteins. In this regard, functional uncoupling of MCM helicase and DNA polymerase occurs in response to several forms of DNA damage and that the subsequent accumulation of ssDNA was required but not sufficient to trigger the ATR-controlled checkpoint response.

Example 5

The xATRIP/xATR Complex Controls Chromatin Binding of xFANCD2 Independently of xFANCA ATR plays a critical role in coordinating the response to DNA damage. Its activation is usually linked to ongoing DNA replication (Hekmat-Nejad et al., *Curr. Biol.* 10:1565-1573, 2000; Lupardus et al., *Genes Dev.* 16:2327-2332, 2002; Stokes et al., *J. Cell Biol.* 158:863-872, 2002; Tercero et al., *Mol. Cell.* 11:1323-1336, 2003). The current model suggests that the ATR complex consisting of the ATR kinase and its binding partner, ATRIP (ATR-interacting protein) control S-phase progression in response to DNA damage and replication fork stalling. ATR and ATRIP are mutually dependent partners in the cellular S-phase checkpoint and DNA damage response (Ball and Cortez, *J. Biol. Chem.* 280:31390-31396, 2005; Ball et al., *Mol. Biol. Cell* 16:2372-2381, 2005; Bomgarden et al., *J. Biol. Chem.* 279:13346-13353, 2004; Cortez et al., *Science* 294:1713-1716, 2001; Falck et al., *Nature* 434:605-611, 2005; Itakura et al., *FEBS Lett.* 577:289-293, 2004; Itakura et al., *Biochem. Biophys. Res. Commun.* 323:1197-1202, 2004; Unsal-Kacmaz and Sancar, *Mol. Cell. Biol.* 24:1292-1300, 2004; Zou and Elledge, *Science* 300:1542-1548, 2003). Generation of RPA-coated ssDNA was the critical signal that triggers recruitment of the tightly associated ATRIP-ATR complex. As disclosed herein, MMC-induced increased in xFA chromatin binding was reversed by the ATR/ATM inhibitor caffeine (FIG. 3A, top left). As shown in FIG. 3C, recruitment of xFANCD2 to chromatin was negligible in replicating extracts depleted of xATRIP, regardless of whether replicating extracts were unchallenged or treated with aphidicolin. In contrast, the xATRIP-depleted extracts still fully supported recruitment of xFANCA to chromatin, in the presence or absence of aphidicolin. Similar results were obtained when extracts contained the neutralizing xATR antibody that blocks xATR PI-3 kinase function.

To further investigate the influence of ATRIP on the FA pathway, xFANCA was quantitatively depleted from replicating extracts and tested for chromatin binding of xATRIP. Since levels of chromatin-associated xATRIP during unperturbed replication were barely detectable by Western blot (FIGS. 3C and D), aphidicolin was added to induce increased chromatin recruitment of xATRIP. As shown in FIG. 3D, immunodepletion of xFANCA did not affect the aphidicolin-induced chromatin recruitment of xATRIP. Thus, the xATRIP-xATR complex regulates recruitment of xFANCD2 to chromatin independently of the regulation that xFANCA and other core complex proteins exert in unperturbed replication as well as in response to replication fork stalling.

Example 6

Chromatin-Association of xFANCD2 Depends on xFANCA

Figure 4:
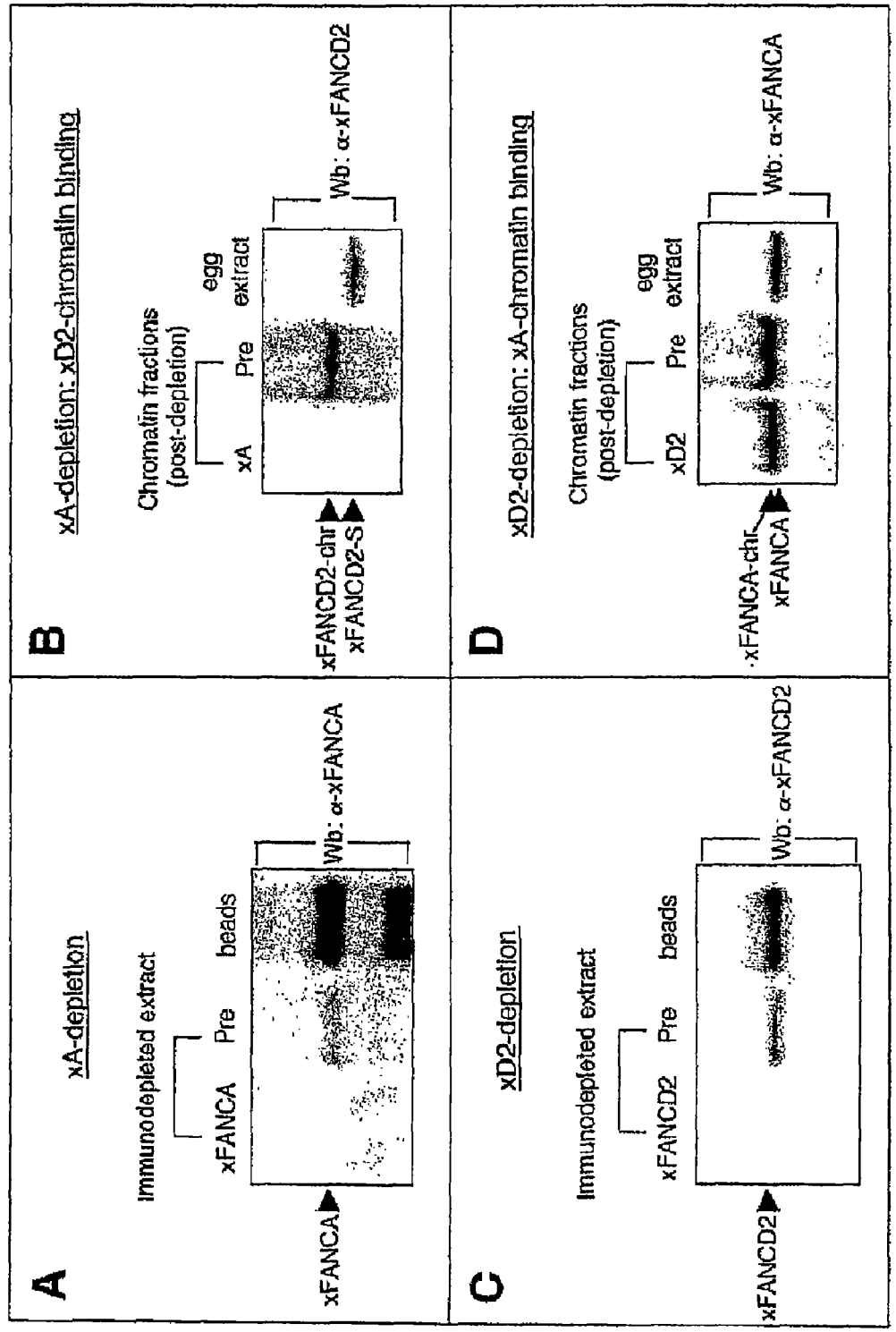
FIGS. 4A-4D are a set of digital images of immunoblots demonstrating replication-associated chromatin binding of xFANCD2 requires the presence of xFANCA.

A functional FA core complex is believed to act upstream of FANCD2 by mediating its monoubiquitination (Garcia-Higuera et al., *Mol. Cell.* 7:249-262, 2001; Taniguchi et al., *Blood* 100:2414-2420, 2002. The core complex protein xFANCA was quantitatively depleted from egg extracts to determine its influence on recruitment of xFANCD2 to chromatin (FIG. 3A). Sperm chromatin was added to the xFANCA-depleted extracts, followed by one round of replication and subsequent re-isolation of replicated chromatin after 90 minutes. As shown in FIG. 4B, replication-associated binding of xFANCD2 to chromatin is abrogated in the absence of xFANCA. In contrast, immunodepletion of xFANCD2 (FIG. 4C) from egg extracts did not affect chromatin binding of xFANCA (FIG. 4D). These results indicate that the xFANCA core complex was required for recruitment or stabilization of xFANCD2 at chromatin in response to DNA damage encountered during the replication process.

Example 7 xFANCA and xFANCD2 are Required to Prevent Accumulation of DNA DSBs During Replication Accumulating evidence points to a role for the FA pathway in the repair of DNA DSBs (Donahue and Campbell, *J. Biol. Chem.* 277:46243-46247, 2002; Donahue et al., *J. Biol. Chem.* 278:29487-29495, 2003; Nakanishi et al., *Proc. Natl.*

Acad. Sci. USA 102:1110-1115, 2005; Rothfuss and Grompe, Mol. Cell. Biol. 24:123-134, 2004; Yamamoto et al., Mol. Cell. Biol. 25:34-43, 2005; Yamamoto et al., Mol. Cell. Biol. 23:5421-5430, 2003). These results imply that xFA proteins are specifically recruited to chromatin during unperturbed replication and when exogenous DNA damage was encountered during replication. It was then determined whether the absence of xFANCA (as core complex member) or xFANCD2 (as downstream effector of the FA core complex) affect the overall kinetics, of DNA replication.

Figure 5:
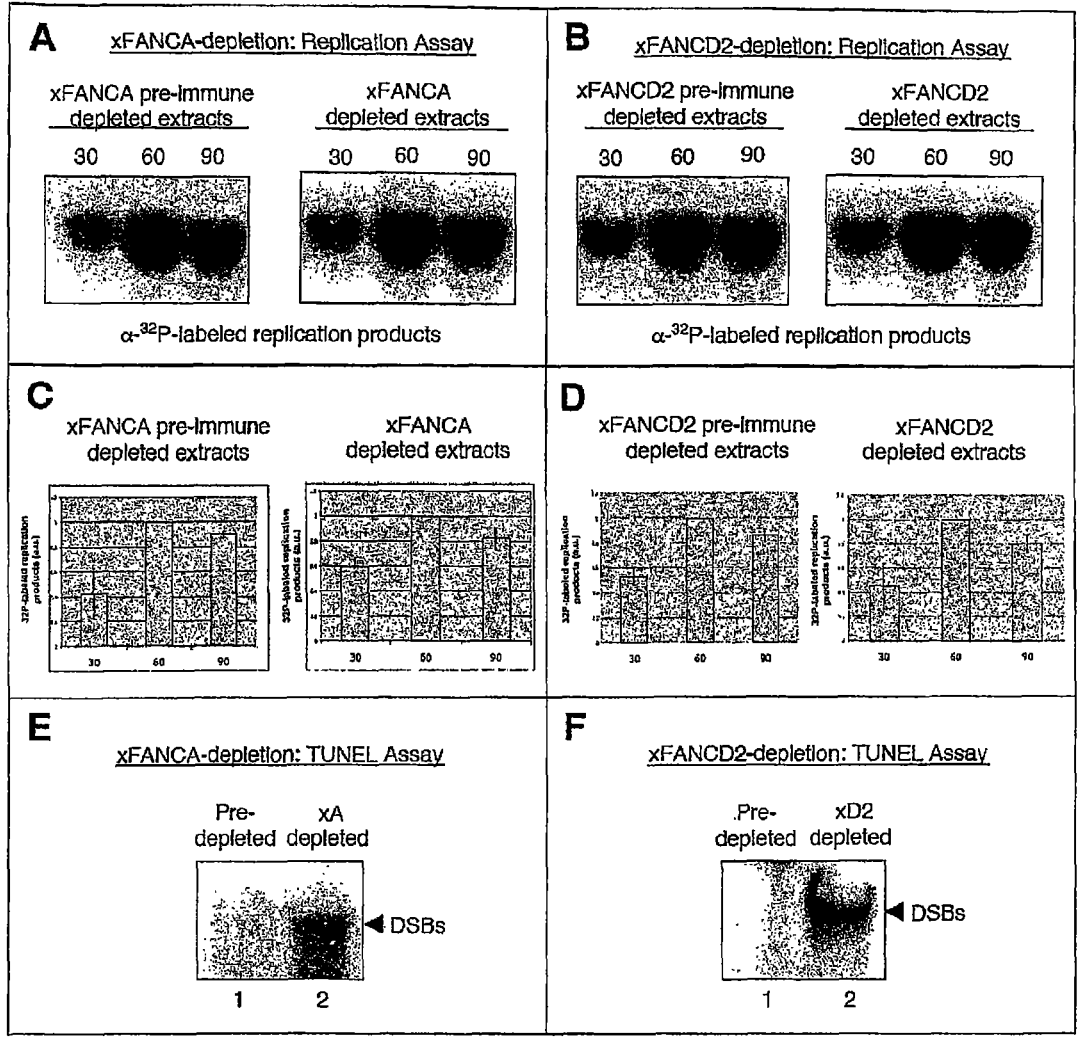
FIGS. 5A-5F are a set of digital images of autoradiographs and bar graphs demonstrating xFA proteins are required to prevent accumulation of DNA breaks during unperturbed replication.

Following immunodepletion of xFANCA or xFANCD2 from egg extracts, timing and levels of nucleotide incorporation was monitored during chromosomal replication. No gross difference in replication kinetics was observed between mock- and xFANCA-depleted extracts (FIGS. 5A and C), or between mock- and xFANCD2-depleted extracts (FIGS. 5B and D). Thus, neither xFANCA nor xFANCD2 are required for initiation or elongation in the replication process itself. A TUNEL assay was used to investigate whether the xFA proteins might be necessary to prevent the accumulation of DNA DSBs that are known to arise during the course of normal replication. Chromosomal DNA was added to pre-immune, xFANCA- or xFANCD2-depleted extracts, followed by one round of replication and subsequent re-isolation of replication products. Putative DNA DSBs in the postreplicative chromatin were labeled using terminal transferase and radioactive deoxynucleotides. Strong signals were detected for incorporation of $^{32}$P-dGTP in replication products from extracts depleted of either xFANCA or xFANCD2, compared to mock-depleted extracts. Thus, absence of xFANCA (FIG. 5E) or xFANCD2 (FIG. 5F) from egg extracts results in accumulation of DNA breaks during unperturbed DNA replication.

Example 8

DNA Substrate-Induced Monoubiquitination of xFANCD2

This example demonstrates that monoubiquitination of FANCD2 can be induced by in Xenopus egg extracts by DNA double strand breaks (DNA DSBs).

dsDNA fragments (two dsDNA ends per molecule) were generated by restriction digest of a double stranded plasmid DNA. After incubation of the dsDNA fragments with Xenopus egg cell free extracts, 1 ul of extract was analyzed by SDS-PAGE and western blot. As shown in FIG. 9A, the slower migrating form of xFANCD2 (xFANCD2-L) was detected in extracts containing dsDNA fragments but not in DNA-free extracts (FIG. 9A, panel 2). Similarly, the hyperphosphorylated-form of xMre11 (xMre11-PPP) was induced in the presence of dsDNA fragments (FIG. 9A, panel 1). xFANCA did not show a detectable size difference in the DNA fragment containing extract, indicating that the dsDNA fragments did not trigger xFANCA modification (FIG. 9A, panel 3).

Figure 9:
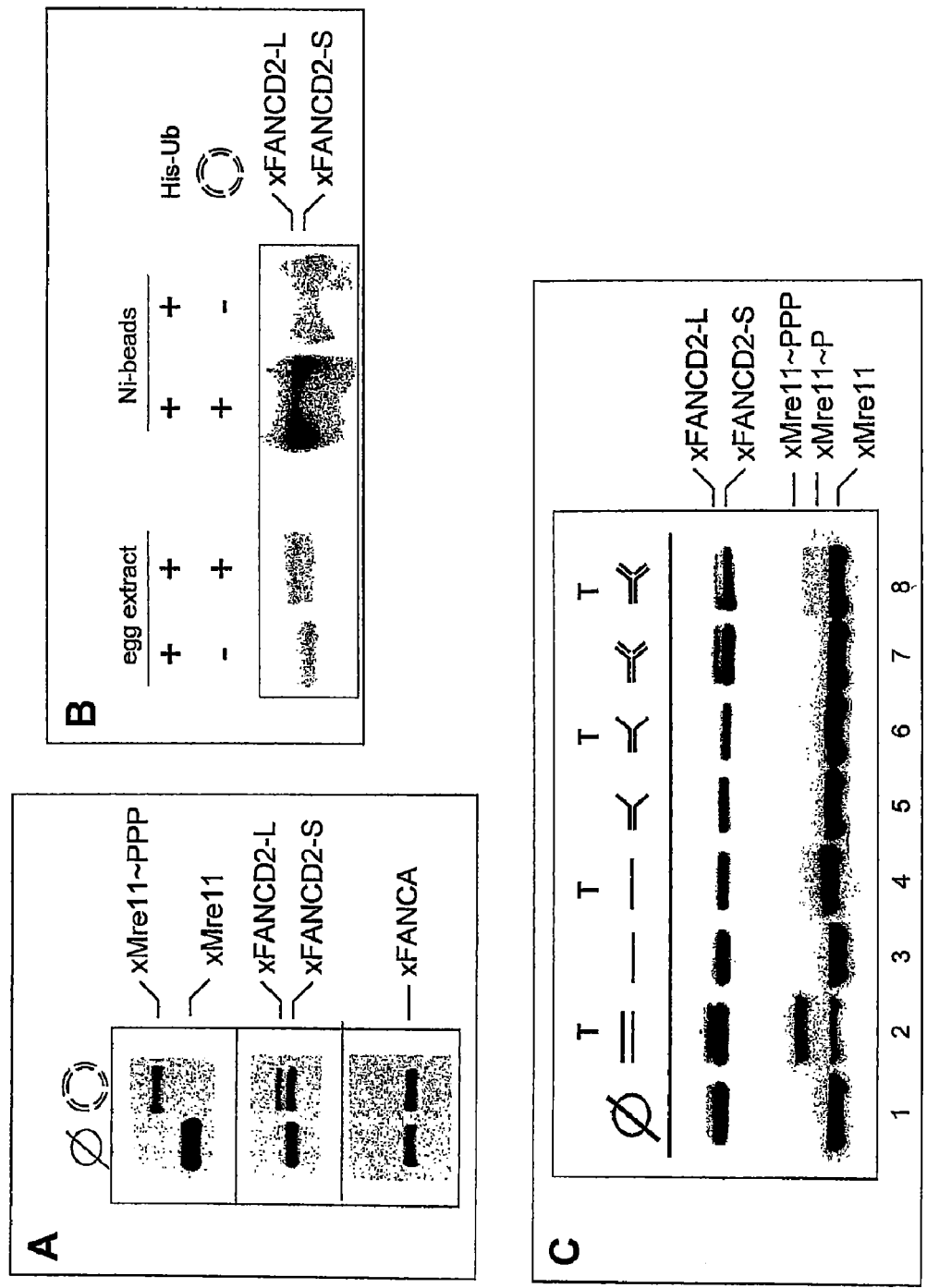
FIGS. 9A-9C are a set of digital images of immunoblots demonstrating the monoubiquitination of xFANCD2 in response to dsDNA.

To determine if the slower migrating form of xFANCD2 (xFANCD2-L) was monoubiquitinated in response the dsDNA His-tagged ubiquitin was added to DNA-free or dsDNA-fragment containing extracts. His-Ub-tagged proteins were re-isolated after 60 minutes. As shown in FIG. 9, His-Ub-xFANCD2 was isolated from extracts containing dsDNA fragments but not from DNA-free extracts, demonstrating that the dsDNA fragment-induced xFANCD2-L form represents monoubiquitinated xFANCD2.

Example 9

Linear and Branched dsDNA Substrates Trigger Activation of xFANCD2-L

This example demonstrates that both linear and branched DNA activates post translational modification of xFANCD2.

Figure 10:
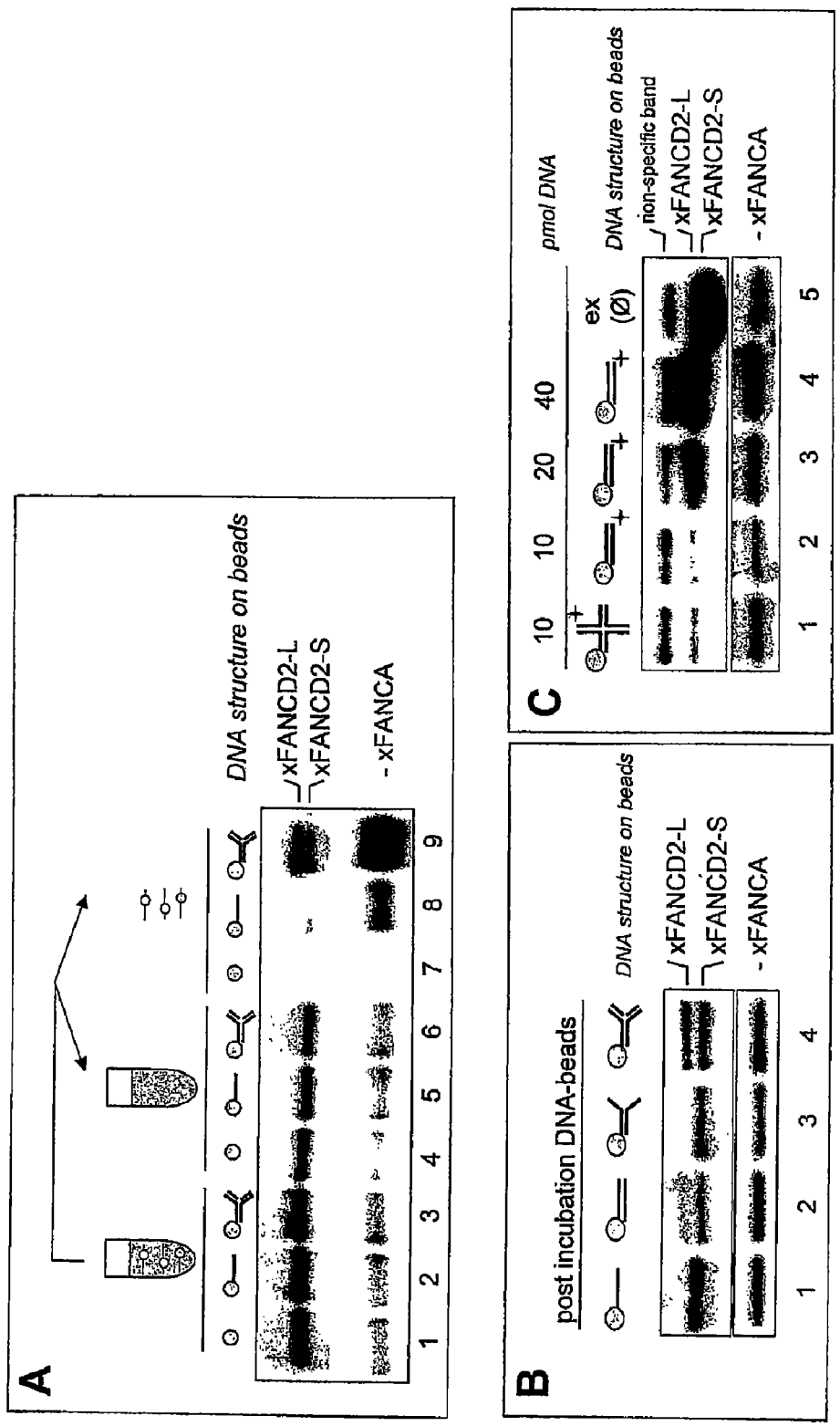
FIGS. 10A-10C are a set of digital images of immunoblots demonstrating that xFANCD2-L associates with linear and branched dsDNA structures.

To further investigate which DNA structures trigger translational modification xFANCD2 to form monoubiquitinated xFANCD2 (FANCD2-L), four DNA substrates that mimic DNA lesions known to arise during replication were compared: (S1) single stranded linear DNA (ssDNA$_{70}$; length: 70 nt), (S2) double stranded linear DNA (dsDNA$_{70}$; length: 70 bp), (S3) Y-shaped DNA (Y-DNA$_{70}$; length across: 70 bp) and (S4) forked dsDNA (fork-DNA$_{70}$; length across: 70 bp). Following incubation of Xenopus egg cell free extracts with the DNA structures S1-S4, the extracts were analysed for the presence of xFANCD2-L and xMre11-PPP as described above. As expected from its structural similarity with the dsDNA fragments described above, the dsDNA$_{70}$ substrate induced both xFANCD2-L and xMre11-PPP (FIG. 9C, lane 2). In addition, the DNA$_{70}$ fork (FIG. 9C, lanes 7+8), but not the ssDNA$_{70}$ (FIG. 9C, lanes 3+4) or the Y-shaped DNA$_{70}$ structures (FIG. 9C, lanes 5+6) triggered modification of xFANCD2 (FIG. 10). Of note, xFANCA did not show a detectable mobility shift in response to any of the 4 DNA structures. Interestingly, despite the presence of three dsDNA ends in the forkDNA$_{70}$ structure, this substrate did not induce xMre11-PPP (FIG. 9C, lanes 7+8).

Example 10 xFANCD2-L Associates with Branched and Linear dsDNA Substrates

This example demonstrates that monoubiquitinated xFANCD2 associates with the DNA structures that triggered its formation.

ssDNA$_{70}$ (non-activating DNA structure for xFANCD2) and the forkDNA$_{70}$ (activating DNA structure for xFANCD2) were coupled to magnetic beads prior to incubation in Xenopus egg extracts. After incubation for 30 minutes, the bead-DNA structures were separated from the extract and both fractions analyzed separately. As shown in FIG. 10A, xFANCD2-L was induced in the presence of bead-forkDNA$_{70}$ but not in the presence of bead-ssDNA$_{70}$ in the extract (compare FIG. 10A lanes 2 and 3). Importantly, separation of the bead-DNA structures from the extract after 30 minutes revealed that xFANCD2-L was associated with the bead-forkDNA$_{70}$ (FIG. 10A, lane 9), whereas no remaining xFANCD2-L was detected in the post-incubation extract (FIG. 10A, lane 6). Next, xFANCD2-L recruitment to bead-bound ssDNA$_{70}$, dsDNA$_{70}$, Y-DNA$_{70}$, and fork-DNA$_{70}$ was directly compared. As shown in FIG. 10B, the monoubiquitinated xFANCD2-L form associated with dsDNA$_{70}$ (FIG. 10B, lane 2) and fork-DNA$_{70}$ FIG. 10B (FIG. 10B, lane 4), but not with ssDNA70 (FIG. 10B, lane 1) or Y-DNA70 (FIG. 10B, lane 3), consistent with the results described in example 8 above. Interestingly, a portion of the non-ubiquitinated form of xFANCD2, xFANCD2-S, was associated with all four bead-DNA substrates (see FIG. 10A, lanes 8 and 9; FIG. 2B, lanes 1-4). xFANCA associated with all 4 DNA structures and did not exhibit any size differences when associated with the respective bead-DNA structure (FIG. 10B, lanes 1-4). Thus, xFANCD2-L associates tightly with the forkDNA$_{70}$ structure and can be isolated from egg extracts in its monoubiquitinated, DNA-bound form.

In summary, these results show that non-modified xFANCD2 associated with the DNA substrates irrespective of their structure, whereas the monoubiquitinated L-form selectively associated only with linear dsDNA (dsDNA$_{70}$) and forked dsDNA (forkDNA$_{70}$).

Example 11 xFANCD2-L Associates with Holliday Junctions

This example demonstrates localization of monoubiquitinated FANCD2 to holliday junction (HJ).

Simulated holliday junction (HJ) were constructed as described. xFANCD2-L recruitment using different molar ratios was compared between the two structures: dsDNA$_{68}$: HJ-DNA$_{68}$ at 1:1 (equal number of DNA molecules/ul extract), at 2:1 (equal number of total DNA base pairs/ul extract) and at 3:1 (=equal number of free dsDNA ends/ul extract). Bead-DNA structures were incubated in *Xenopus* egg extracts, re-isolated, and analyzed as described above. As shown in FIG. 10C, similar amounts of xFANCD2-L were associated with the HJ structure compared to the linear DNA substrate at a molar ratio of 1:1 between the two structures (compare FIG. 10C lanes 1 and 2). In addition, xFANCD2-L recruitment to the HJ-DNA68 did not occur proportionally to its number of DNA ends (compare FIG. 10C lanes 1 and 4) or in proportion to the total number of DNA base pairs present in the HJ structure (compare FIG. 10C lanes 1 and 3). Interestingly, while the increase in dsDNA$_{68}$ molecules incubated per extract volume was linear (1:2:3 in FIG. 10C lanes 2, 3, 4, respectively), the increase of dsDNA$_{68}$-bound xFANCD2-L was not (compare FIG. 10C lanes 2, 3, and 4), hinting that with increasing DNA concentration, the number of bound xFANCD2-L proteins per single DNA molecule increased.

Taken together, xFANCD2-L was triggered by—and recruited to—cruciform holliday junction DNA but did not show a significant preference towards this structure compared to a linear dsDNA fragment.

Example 12

DNA-Bound xFANCD2-L is Controlled by the FA Core Complex

This example demonstrates that monoubiquitination of FANCD2 in response to DNA damage depends on the fully assembled FA core complex.

Figure 11:
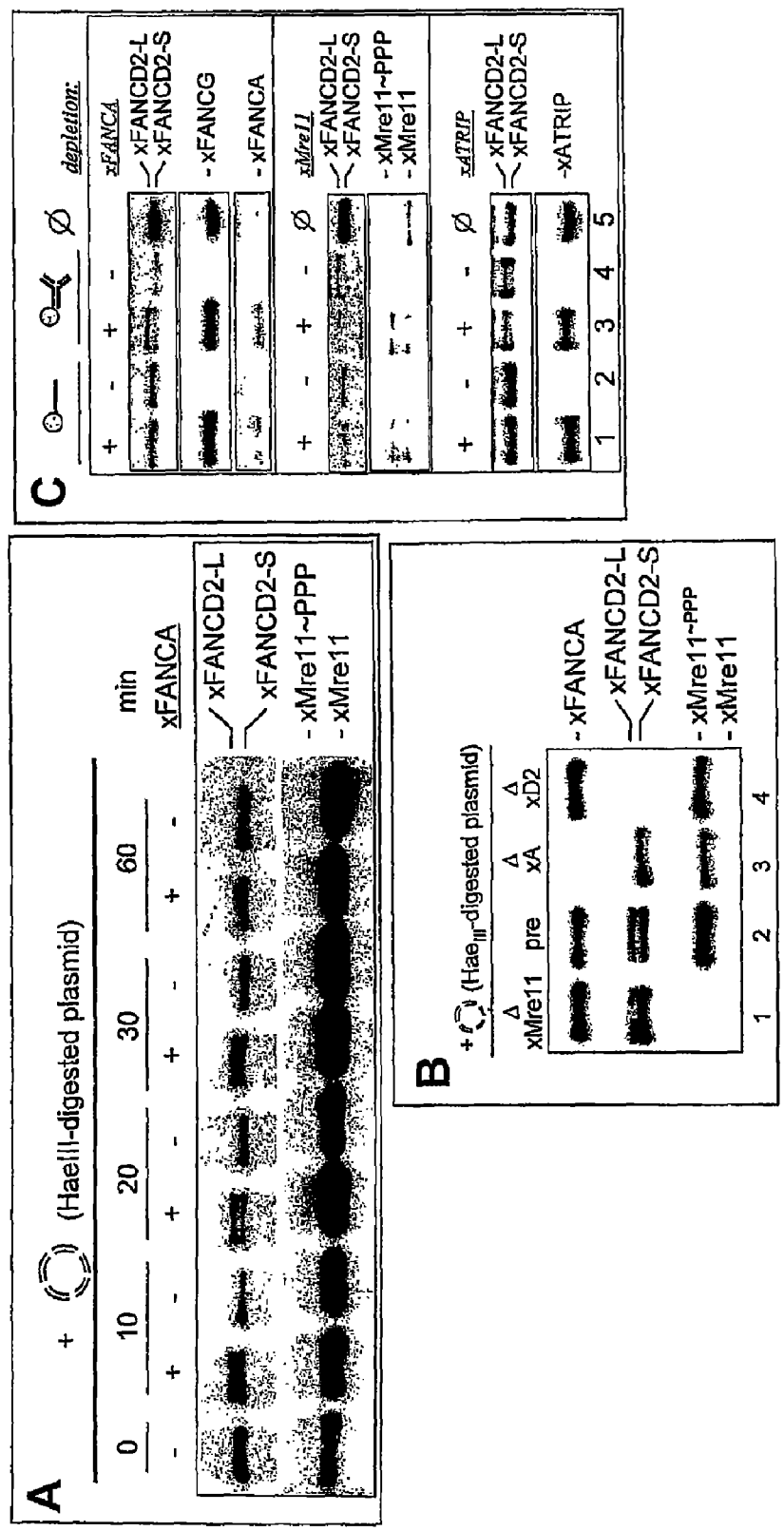
FIGS. 11A-11C are a set of digital images of immunoblots demonstrating that DNA-induced formation and recruitment of xFANCD2-L is dependent on FANCA, but not on xMre11 or the ATR/ATRIP complex.

To determine if monoubiquitination of xFANCD2 in extracts containing dsDNA fragments is dependent on the FA core complex, the core complex protein xFANCA was depleted from extracts followed by incubation with plasmid-derived dsDNA fragments (see also FIG. 9 A) was depleted. As shown in FIG. 11A and FIG. 11B, xFANCD2-L was completely absent in dsDNA fragment-containing extracts depleted of xFANCA compared to mock-depleted extracts. Interestingly, the dsDNA fragment-induced activation of xMre11-PPP was also inhibited in xFANCA-depleted extracts compared to the control extracts (FIG. 1A and FIG. 1B). In contrast, depletion of xFANCD2 did not inhibit activation of xMre11-PPP (FIG. 11B) or vice versa. Thus, formation of xFANCD2-L and xMre11-PPP in response to dsDNA fragments is regulated by the FA core complex, but occurs independently of each other.

Next it was determined whether association of xFANCD2-S or xFANCD2-L with DNA substrates is FA core complex-dependent. Bead-coupled ssDNA$_{70}$ and forkDNA$_{70}$ were incubated in xFANCA-depleted or mock-depleted *Xenopus* egg extracts. Interestingly, binding of xFANCD2-S to ssDNA$_{70}$ or forkDNA$_{70}$ was not affected in the absence of xFANCA (lanes 2+4). In contrast, association of xFANCD2-L with the forkDNA$_{70}$ substrate was absent in xFANCA-depleted extracts compared to mock-depleted extracts (compare lanes 3+4). Thus, xFANCD2-S can associate with DNA independently of the FA core complex whereas DNA binding of xFANCD2-L is strictly core complex-dependent. It was also tested whether absence of xMre11 might affect xFANCD2 binding to the ssDNA$_{70}$ or forkDNA$_{70}$ substrates. As expected from the results shown in FIG. 11B (panel 2), depletion of xMre11 did not affect binding of xFANCD2-S or -L to the respective DNA substrate.

It was tested whether association of xFANCD2 with ssDNA$_{70}$ or forkDNA$_{70}$ requires the presence of xATRIP. Surprisingly, neither binding of xFANCD2-S to ssDNA$_{70}$, nor association of FANCD2-L with the forkDNA$_{70}$ was affected in ATRIP-depleted extracts compared to control extracts. Thus, whereas the xATR/xATRIP complex is required to target xFANCD2-L to replicating chromatin, it appears dispensable for the association of xFANCD2 with the short single- and double-stranded DNA structures used in this in vitro assay.

Example 13

Activation of the FA Pathway does not Require the Presence of dsDNA Ends

This example demonstrates that monoubiquitination of does not require dsDNA ends.

Figure 12:
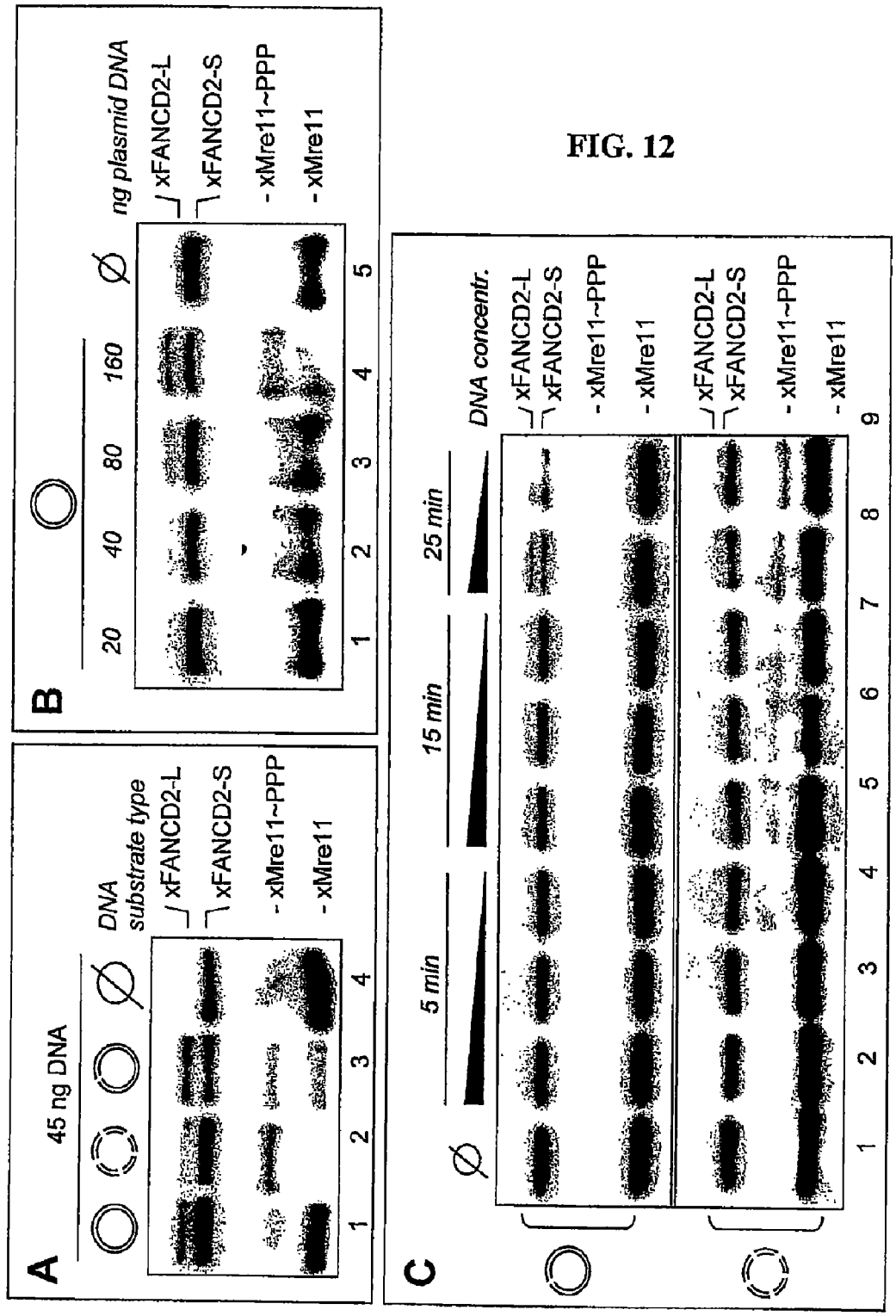
FIGS. 12A-12C are a set of digital images of immunoblots demonstrating that double stranded DNA ends are not a major trigger for xFANC2-L formation.

The induction of xFANCD2-L in extracts containing equal amounts of (I) circular, supercoiled pBluescript plasmid (no DNA ends), (II) linearized pBluescript plasmid (two DNA ends per plasmid molecule), and (III) HaeIII-digested pBluescript plasmid (22 DNA ends [11 DNA fragments] per plasmid molecule) was compared. Strikingly, xFANCD2-L was induced in response to all three DNA substrates (FIG. 12 A). In each case, induction of xFANCD2-L was abrogated when xFANCA was depleted from the extract, showing that these responses are part of the FA pathway. On the other hand, xMre11-PPP was induced only in the presence of DNA ends (HaeIII-cut plasmid>>linearized plasmid; FIG. 12C, compare lanes 2 and 3) but not in response to the circular plasmid (FIG. 12C, lane 4). It is important to note that at higher concentrations of the circular plasmid, activation of xMre11-PPP was observed (FIG. 12B), possibly due to the presence of a small number of dsDNA breaks in circular plasmid DNA preparations.

To further analyze the response of xFANCD2 and Mre11 to the linear dsDNA fragments, timing and DNA dose-dependency of xFANCD2-L and xMre11-PPP formation in response to linearized and HaeIII-cut plasmid was compared. As shown in FIG. 12C, xFANCD2-L was detected as early as 15 minutes following addition of the linearized plasmid DNA (at 20 and 10 ng/ul), whereas xMre11-PPP was not detectable even at a later time point (25 minutes). In contrast, in the presence of HaeIII-generated DNA fragments, xMre11-PPP was detectable at 15 minutes at all three DNA concentrations (20, 10, and 5 ng/ul, lanes 5-7), whereas xFANCD2-L was detected later and only at the highest DNA concentration (25 minutes, 20 ng/ul, lane 8). In summary, in contrast to xMre11, activation of xFANCD2 occurs in response to the presence of linear dsDNA but not dsDNA ends in egg extracts.

Example 14

Figure 13:
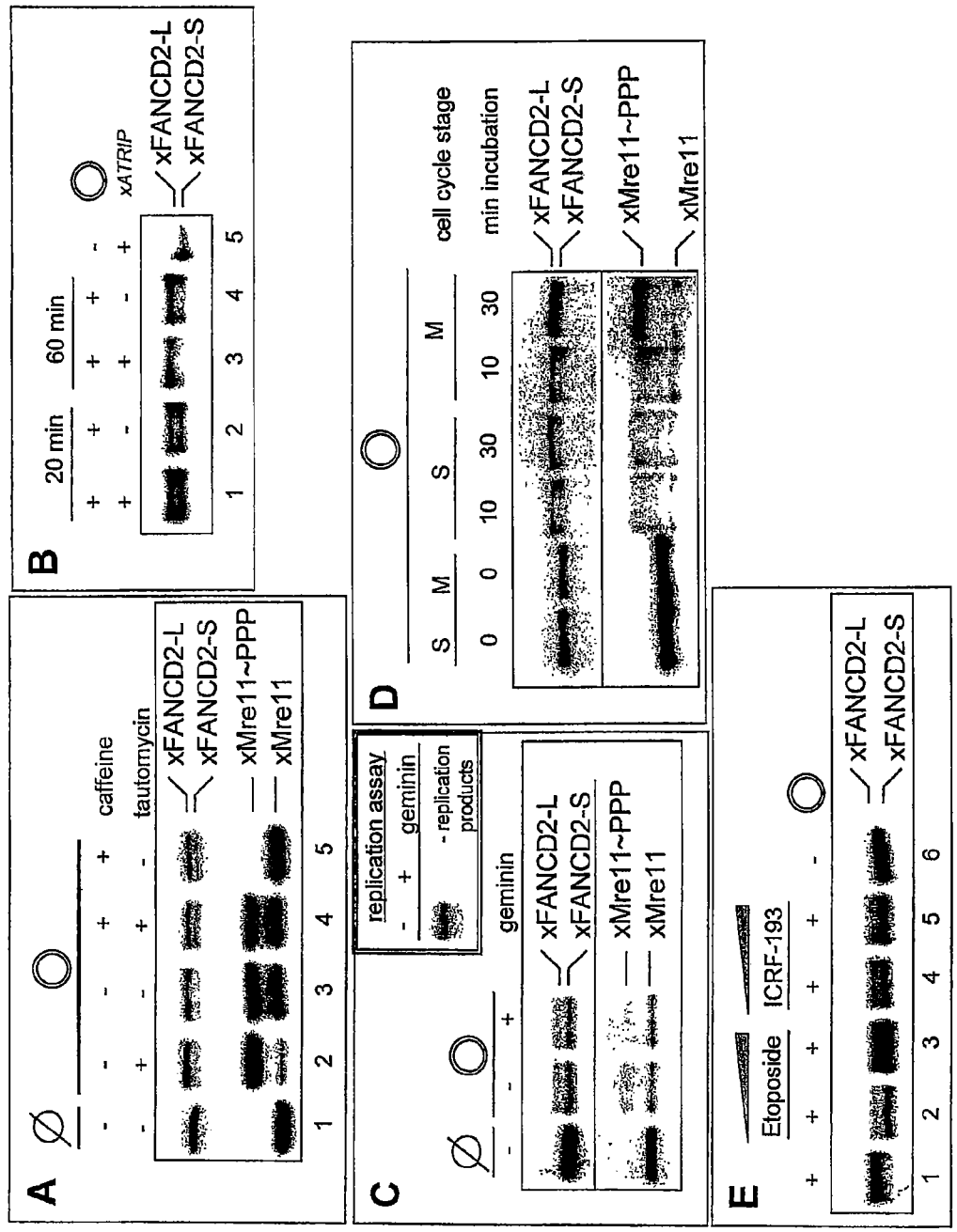
FIGS. 13A-13E are a set of digital images of immunoblots demonstrating that the formation of xFANCD2-L in response to circular dsDNA is replication- and checkpoint-independent, but requires topoisomerase II α.

Circular Plasmid-Induced Activation of the FA Pathway is Checkpoint- and Replication Independent As described above, egg extracts containing circular plasmid DNA induce activation of xFANCD2-L, and at high plasmid concentrations, xMre11-PPP. One possibility is that the presence of plasmid DNA activates a checkpoint in the egg extract, which in turn might activate cFANCD2-L. To test this possibility caffeine, an inhibitor of ATM, ATR and the Chk family of protein kinases, was added to egg extracts containing high concentrations of circular plasmid DNA (100 ng/ul). As shown in FIG. 13A, activation of xFANCD2-L was not significantly affected in the presence of caffeine, whereas induction of xMre11-PPP was inhibited (compare FIG. 13A lanes 2 and 4; 3 and 5). In agreements with this, induction of Mre11-PPP in response to dsDNA fragments (generated by HaeIII-digest) is inhibited in the presence of caffeine. Depletion of xATRIP, which functionally resembles absence of the checkpoint mediator, from egg extracts had no effect on the plasmid-induced xFANCD2-L induction (FIG. 13B). Taken together, activation of xFANCD2-L in the presence of circular plasmid DNA is not part of a checkpoint response.

Next it was determined if replicative DNA synthesis on the circular plasmid template was responsible for activating xFANCD2-L. Plasmid DNA that is directly added to an S-phase egg can be remodeled into a functional nucleus and replicated, although replication efficiency is very low under these conditions (approx 6%). A replication initiation inhibitor, geminin, was added to egg extracts containing circular plasmid DNA (100 ng/ul). As shown in FIG. 13C, addition of geminin did not affect formation of xMre11-PPP or xFANCD2-L in response to the plasmid DNA. Comparison was also made to plasmid-induced formation of xFANCD2-L and xMre11-PPP between a replication-competent S-phase extract and a replication-incompetent M-phase egg extracts. Induction of xFANCD2-L or xMre11-PPP was identical between plasmid-containing S-phase and M-phase extracts (FIG. 13D), indicating that formation of xFANCD2-L and xMre11-PPP was not due to replication of the plasmid DNA.

Example 15

Inhibitors of Topopisomerase IIα Block xFANCD2-L in Response to Circular Plasmid DNA Plasmid DNA is remodeled into functional chromatin upon its addition to egg extracts in a step that requires DNA topoisomerase IIα. To test whether structural remodeling of the plasmid DNA is triggering the FA pathway, two topoisomerase IIα inhibitors, etoposide and ICRF-193, was added to plasmid-containing egg extracts. As shown in FIG. 13E, induction of xFANCD2-L in the presence of circular plasmid DNA was significantly blocked in the presence of etoposide or ICRF-193. Thus, topoisomerase IIα-mediated plasmid remodeling in egg extracts is a strong trigger for the FA pathway.

Example 16 xFANCM Exhibits a DNA-Stimulated Mobility Shift in Xenopus Egg Cell Free Egg Extracts This example demonstrates the stimulation of xFANCM post-translational modification in response to double-stranded DNA.

dsDNA fragments (two dsDNA ends per molecule) were generated by digesting circular pBluescript plasmid (pB-SKS+, 2961 bp) with the restriction endonuclease HaeIII to generate a total of 15 blunt-ended dsDNA fragments of various sizes (between 11 and 458 bp in length). After incubation of the dsDNA fragments with Xenopus egg cell free extracts, 1 ul of extract was analyzed by SDS-PAGE and western blot. As shown in FIG. 1, the slower migrating form of xFANCM (xFANCM-L) was detected in extracts containing dsDNA fragments but not in DNA-free extracts. The slower migrating form of xFANCD2 (xFANCD2-L) was also detected in extracts containing dsDNA fragments but not in DNA-free extracts. Similarly, the hyperphosphorylated form of xMre11 (xMre11-PPP) was induced in the presence of dsDNA fragments.

Example 17

Identification of Agents that Affect the Fanconi Anemia Pathway

This example demonstrates the methods used to identify compounds that act as modulators of the Fanconi anemia.

Fifty four compounds obtained from the Developmental Therapeutics Program NCI/NIH were screened for their effect on the Xenopus Fanconi anemia pathway using the Xenopus egg cell free extracts described herein. This challenge set consisted of 54 compounds of novel structural types plated at 10 mM in 20 uL. The 54 compounds have been previously evaluated in the DTP human tumor cell line assay (Monks et al., *J. Natl. Cancer Inst.* 83:757-766 1991) and display unusual patterns of cell line sensitivity and resistance. COMPARE™ analysis against the National Cancer Institute (NCI) standard agent database indicated no previously known mechanism of action for these compounds.

10 ul Xenopus egg extracts was combined with 0.5 ul compound (10 mM) or curcumin (control, 23 uM) then 0.5 ul plasmid DNA (pBluescript, 3.4 ug/ul) was added. The sample was incubated for 45 minutes at room temperature. 60 ul of 1×SDS loading buffer was added and the samples were incubated at 95° C. for 10 minutes to quench the reaction. Individual samples were loaded onto were resolved onto a NUPAGE™ 3-8% tris-acetate gradient gel (Invitrogen), resolved, and transferred onto a PVDF membrane (Immobilon P, Millipore). Blots were probed successively with primary rabbit polyclonal antibodies specific to Xenopus FANCD2 and Mre11. Blots were washed and probed with secondary HRP-coupled secondary anti-rabbit antibody, and visualized using the ECL PLUS® kit (Amersham).

Figure 6:
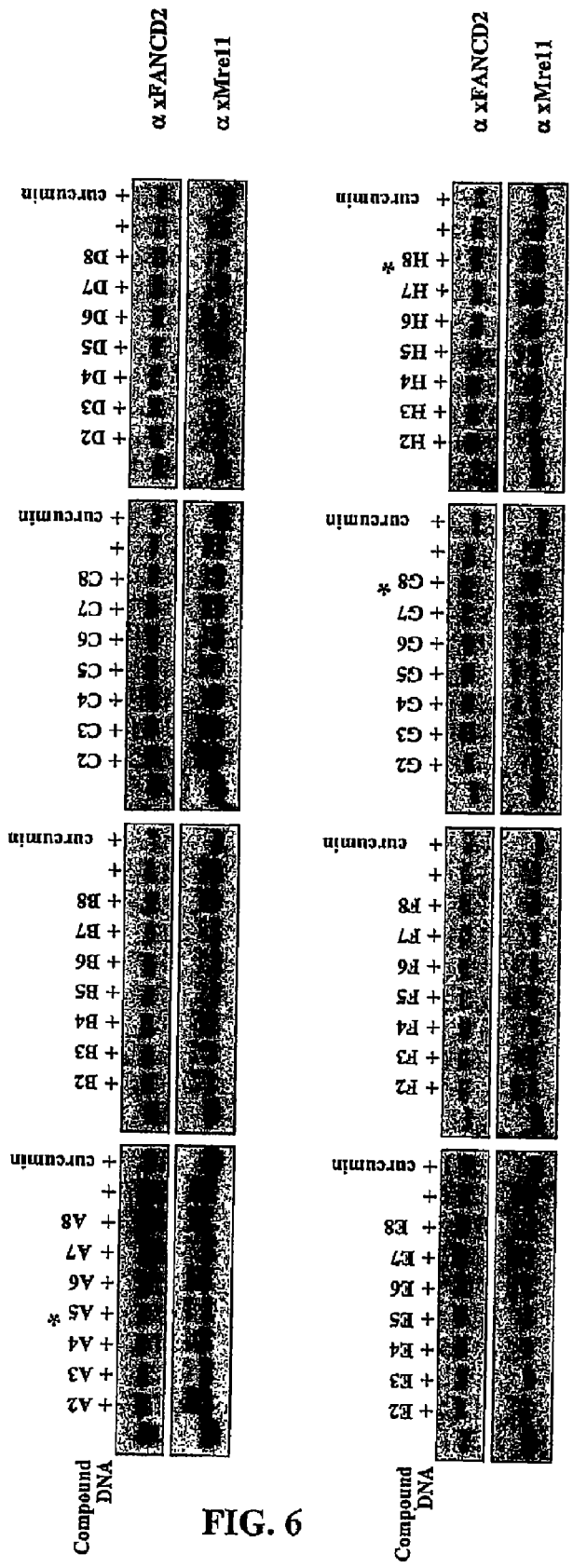
FIG. 6 is a set of digital images of immunoblots demonstrating the affect of 54 compounds obtained from the Developmental Therapeutics Program NCI/NIH. Six of the compounds tested (CS-A3, CS-A7, CS-C4, CS-E3, CS-F2, CS-F5) exhibited modulation of xFANCD2 activation. Three of the compounds (CS-A3, CS-A7, CS-E3) were potential inhibitors of xFANCD2 activation (ubiquitination). Three of the compounds (CS-F2, CS-C4, CS-F5) were found to be potential activators of xFANCD2 activation (ubiquitination).

Of the 54 compounds tested 6 (CS-A3, CS-A7, CS-C4, CS-E3, CS-F2, CS-F5) were positive for modulation of xFANCD2 activation (see FIG. 6). Four of the compounds (CS-A3, CS-A7, CS-E3) were potential inhibitors of xFANCD2 activation (ubiquitination). Two of the compounds (CS-C4, CS-F2, CS-F5) were found to be potential activators of xFANCD2 activation (ubiquitination). Two of the compounds that scored positive in the initial screen (CS-A3 and CS-E3) were tested for dose dependent response (FIG. 7A). Xenopus egg cell free extracts were incubated with the indicated concentration of test compound and analyzed as described in the preceding paragraph. Compound CS-A3 displayed a moderate inhibitory effect on aFANCD2 activation (ubiquitination). In contrast, compound CS-E3 appears to be a potent inhibitor of FANCD2 activation (ubiquitination). In the DTP human tumor cell line assay compound CS-A3 had an average $GI_{50}$ of 15.4 uM (50% growth inhibition), an average $TGI_{50}$ of 38.4 uM (100% growth inhibition), and an average LC50 of >72 uM (50% death). In the DTP human tumor cell line assay compound CS-E3 had an average $GI_{50}$ of 0.835 uM (50% growth inhibition), an average $TGI_{50}$ of 5.8 uM (100% growth inhibition), and an average $LC_{50}$ of 17 uM (50% death).

Potential therapeutic agents identified with these or other approaches (such as compounds CS-A3, CS-A7, CS-C4, CS-E3, CS-F2, CS-F5), including the specific assays and screening systems described herein, are used as lead compounds to identify other agents having even greater modulatory effects on the FA pathway. For example, chemical analogs of identified chemical entities, or variant, fragments of fusions of peptide agents, are tested for their activity in the assays described herein. Candidate agents also can be tested in cell lines and animal models of cancer and/or Fanconi anemia to determine their therapeutic value. The agents also can be tested for safety in animals, and then used for clinical trials in animals or humans.

Example 18

Identification of Agents that Affect the Fanconi Anemia Pathway

This example demonstrates the methods used to identify compounds that act as modulators of the Fanconi anemia.

Two hundred and thirty five natural products were obtained from the Developmental Therapeutics Program NCI/NIH and screened for their effect on the *Xenopus* Fanconi anemia pathway using the *Xenopus* egg cell free extracts described herein. The s 235 natural products were selected for structural diversity and availability of compound. This set was to study a variety of scaffold structures having multiple functional groups.

10 ul *Xenopus* egg extracts was combined with 0.5 ul compound (10 mM) or curcumin (control, 23 uM) then 0.5 ul plasmid DNA (pBluescript, 3.4 ug/ul) was added. The sample was incubated for 45 min at room temperature, then 60 ul of 1×SDS loading buffer. After incubation at 95° C. for 10 min, samples were resolved onto a NUPAGE™ 3-8% tris-acetate gradient gel (Invitrogen) and transferred onto a PVDF membrane (Immobilon P, Millipore). Blots were probed successively with primary rabbit polyclonal antibodies specific to *Xenopus* FANCD2 and Mre11 and secondary HP-coupled secondary anti-rabbit antibody, and revealed using the ECL PLUS™ kit (Amersham).

Figure 14:
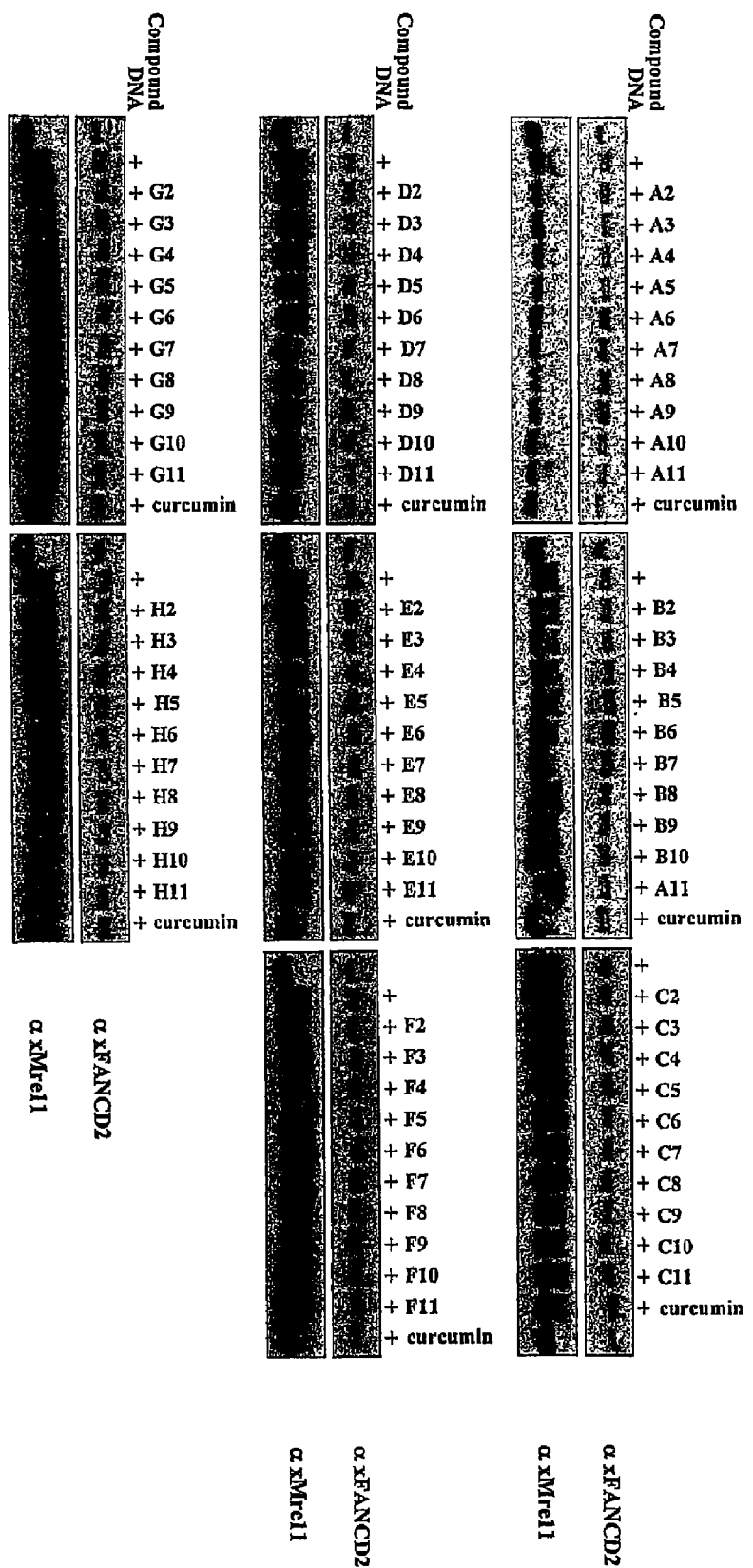
FIG. 14 is a set of digital images of immunoblots demonstrating the affect of 235 Natural product compounds obtained from the Developmental Therapeutics Program NCI/NIH. Seven of the compound tested (NP-A3, NP-A7, NP-D8, NP-E3, NP-F2, NP-F8, and NP-118) exhibited an effect on of xFANCD2 post-translational modification.

Of the 235 compounds tested 7 (NP-A3, NP-A7, NP-D8, NP-E3, NP-F2, NP-F8, NP-H8) were positive for modulation of xFANCD2 activation (see FIG. 14). Membranes initially probed with xFANCD2 antibody were reprobed with xFANCM antibody. The shift corresponding to xFANCM phosphorylation upon addition of DNA (FIG. 7B, lane 2) is strongly stimulated by compound NP-B11 (i.e. cantharidin), a protein phosphatase inhibitor. Thus xFANCM can be used as an indicator of Fanconi anemia pathway activation.

Potential therapeutic agents identified with these or other approaches (such as compounds NP-A3, NP-A7, NP-D8, NP-E3, NP-F2, NP-F8, NP-H8), including the specific assays and screening systems described herein, are used as lead compounds to identify other agents having even greater modulatory effects on the FA pathway. For example, chemical analogs of identified chemical entities, or variant, fragments of fusions of peptide agents, are tested for their activity in the assays described herein. Candidate agents also can be tested in cell lines and animal models of cancer and/or Fanconi anemia to determine their therapeutic value. The agents also can be tested for safety in animals, and then used for clinical trials in animals or humans.

Example 19

Exemplary High Throughput Screening Assay for Effectors of Fanconi Anemia Pathway Activation This example demonstrates the cell free system for use in methods of identifying modulators of xFANCD2 activation.

*Xenopus* egg cell free extracts as described above are provided in a suitable format for rapid screening of potential modulators of xFANCD2 activation. For example, the cell free extract can be provided in a multiwell format, such as a 96 well plate or a 384 well plate. Test agents are added to the plate either at a single concentration or at graded concentrations. The amount of post-translationally modified xFANCD2 is determined in each well and the compared to a control in which no agent has been added. Agents that cause a measurable effect on the activation of xFANCD2 are identified as FA pathway modulators and selected for further tests as potential therapeutic agents.

In one example a *Xenopus* egg cell free extracts are provide in a multiwell format, such as a 96 or 384 well plate. Cell extracts are incubated in the presence of an agent. The contents of the well are transferred to a second plate (for example an enzyme-linked immunosorbent assay (ELISA) plate) pre-coated containing an xFANCD2 specific binding agent, an ubiquitin specific binding agent, or a phosphoserine specific binding agent. The sample is left in contact with the plate under conditions sufficient to allow the binding of the target to the pre-coated plate. The plate is washed and incubated with a second antibody that binds to the target captured by the antibody coated on the plate. The plate is washed again- and visualized for example by labeling the second antibody, for example with a fluorescent tag or horseradish peroxidase (HRP). If HPR is used, tetra-methylbenzidine (TMB) substrate is added and the HRP degrades $H_2O_2$ and oxidizes TMB to form a blue product. The reaction is stopped with an acid, which converts the product from a blue to a yellow color that can be quantified at 450 nm. The optical density (OD) at 450 nm is directly proportional to the amount of bound target.

An agent that is determined to modulate the activation of xFANCD2 is identified having the potential to be useful in the treatment of Fanconi anemia and/or cancer. Agents so identified can be subjected to further testing and characterization.

Example 20

Exemplary High Throughput Radio Nucleotide Based Screening Assay for Modulators of Fanconi Anemia Pathway Activation Rapid screening-assays can be used to screen a large number of agents to determine if they modulate *Xenopus* Fanconi anemia pathway activation (prescreening agents). In one example a *Xenopus* egg cell free extracts are provide in a multiwell format, such as a 96 or 384 well plate. Such plates are readily adapted to robotic manipulation. Cell extracts are incubated in the presence of an agent in the presence of [$\gamma$-$^{32}$P]ATP. The incorporation of $^{32}$P into xFANCD2 is then determined, where in a difference in the incorporation of $^{32}$P relative to a control, for example a known value or a well containing a *Xenopus* egg cell extract that was not contacted with an agent, indicates that the agent is a modulator of the Fanconi anemia pathway. The incorporation of $^{32}$P into xFANCD2 can be determined for example by transferring the extracts to a plate in which an xFANCD2 specific binding agent has been attached. The xFANCD2 in the extract is allowed sufficient time to bind to the xFANCD2 specific binding agent and the remaining extract is washed away. The amount of bound $^{32}$P xFANCD2 can be determined by scintillation or autoradiography. The effect of the agent is then determined in percentages by the formula:

(quantity of $^{32}$P in the absence of the drug)−(quantity of the $^{32}$P in the presence of the drug)/quantity of the label in the absence of the drug)×100

An agent that is determined to modulate the activation of xFANCD2 is identified having the potential to be useful in the treatment of Fanconi anemia and/or cancer. Agents so identified can be subjected to further testing and characterization.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

---

We claim:

1. A method for identifying an agent for the treatment of cancer or Fanconi anemia comprising:
   contacting a *Xenopus* egg cell free extract depleted of endogenous DNA with an agent of interest;
   detecting a post-translationally modified *Xenopus* Fanconi anemia polypeptide in the *Xenopus* egg cell free extract; and
   comparing the amount of the post-translationally modified *Xenopus* Fanconi anemia polypeptide to a control, wherein a difference in the amount of the post-translationally modified *Xenopus* Fanconi anemia polypeptide in the cell extract contacted with the agent, as compared to the control, indicates the agent is of use for treating cancer, Fanconi anemia, or a combination thereof.

2. The method of claim 1, wherein an agent that decreases the amount of the post-translationally modified *Xenopus* Fanconi anemia polypeptide as compared to the control indicates the agent is of use for treating cancer.

3. The method of claim 1, wherein an agent that increases the amount of the post-translationally modified *Xenopus* Fanconi anemia polypeptide as compared to the control indicates the agent is of use for treating Fanconi anemia.

4. The method of claim 1, wherein the *Xenopus* Fanconi anemia polypeptide comprises xFANCD2 or a functional fragment thereof, or xFANCM or a functional fragment thereof.

5. The method of claim 1, wherein the post-translational modification comprises one or more of ubiquitination or phosphorylation.

6. The method of claim 1, further comprising the addition of isolated exogenous double stranded DNA comprising at least one double strand break, wherein the exogenous double stranded DNA is between 10 and 500 nucleotides in length.

7. The method of claim 6, wherein the exogenous double stranded DNA comprises one or more of fragmented plasmid DNA, synthetically produced DNA, or human DNA.

8. The method of claim 6, wherein the exogenous double stranded DNA comprises 5'-(dG)$_{4o}$-(dA)$_{3o}$-3' (SEQ ID NO:3) annealed to 5'-(dT)$_{3o}$-(dC)$_{4o}$-3' (SEQ ID NO:4) or a branched DNA structure comprising 5'-(dG)$_{4o}$-(dA)$_{3o}$-3' (SEQ ID NO:3), 5'-(dA)$_{30}$-(dC)$_{4o}$-3' (SEQ ID NO:5), and (dT)$_{30}$ (SEQ ID NO:6).

9. The method of claim 6, wherein the exogenous double stranded DNA is labeled.

10. The method of claim 6, further comprising isolating the exogenous DNA from the *Xenopus* eggs cell free extracts and evaluating the amount of post-translationally modified *Xenopus* Fanconi anemia polypeptide bound to the exogenous DNA.

11. The method of claim 10, wherein evaluating the amount of the post-translationally modified *Xenopus* Fanconi anemia polypeptide comprises separating the post-translationally modified *Xenopus* Fanconi anemia polypeptide from the non-post-translationally modified *Xenopus* Fanconi anemia polypeptide by apparent molecular weight.

12. The method of claim 10, wherein evaluating the amount of the post-translational modified *Xenopus* Fanconi anemia polypeptide comprises using an antibody that specifically binds the post-translationally modified *Xenopus* Fanconi anemia polypeptide.

13. The method of claim 12, wherein the post-translationally modified *Xenopus* Fanconi anemia polypeptide comprises xFANCD2 and the antibody specifically binds xFANCD2.

14. The method of claim 13, wherein the post-translationally modified *Xenopus* Fanconi anemia polypeptide comprises ubiquitinated xFANCD2 and the antibody specifically binds ubiquitinated xFANCD2.

15. The method of claim 12, wherein the post-translationally modified *Xenopus* Fanconi anemia polypeptide comprises xFANCM and the antibody specifically binds xFANCM.

16. The method of claim 15, wherein the post-translationally modified *Xenopus* Fanconi anemia polypeptide comprises phosphorylated xFANCM and the antibody specifically binds phosphorylated xFANCM.

17. The method of claim 1, wherein the agent is a chemical compound, a small molecule, an antibody, or an antisense nucleic acid.

18. The method of claim 1, wherein the method comprises a high throughput technique.

19. The method of claim 1, wherein DNA can be replicated in the *Xenopus* egg cell free extract.

20. The method of claim 1, wherein the *Xenopus* egg cell free extract is produced from *Xenopus* eggs synchronized in M-phase.

21. The method of claim 1, wherein the control is a standard value.

22. The method of claim 1, wherein the control is the amount of post-translationally modified *Xenopus* Fanconi anemia polypeptide in a *Xenopus* egg cell free extract depleted of endogenous DNA not treated with the agent.

23. The method of claim 1, wherein *Xenopus* egg cell free extracts depleted of endogenous DNA are produced by the method comprising:
   removing jelly in cysteine;
   removing cellular debris and chromatin by centrifugation; and
   adding media comprising creatine phosphate, adenosine triphosphate, MgC12, cytochalasin B, and 4-(2-aminoethyl)benzenesulfonylfluoride.

24. The method of claim 1, wherein the *Xenopus* Fanconi anemia polypeptide comprises xFANCD2 or a functional fragment thereof, and wherein the post-translational modification is monoubiquination.

25. A method for identifying an agent for the treatment of cancer or Fanconi anemia comprising:

contacting a *Xenopus* egg cell free extract depleted of endogenous DNA with an agent of interest;

adding isolated exogenous double stranded DNA comprising at least one double strand break, wherein the exogenous double stranded DNA is between 10 and 500 nucleotides in length;

detecting a post-translationally modified *Xenopus* Fanconi anemia polypeptide in the *Xenopus* egg cell free extract, wherein the post-translational modification comprises ubiquitination or phosphorylation; and comparing the amount of the post-translationally modified *Xenopus* Fanconi anemia polypeptide to a control, wherein a difference in the amount of the post-translationally modified *Xenopus* Fanconi anemia polypeptide in the cell extract contacted with the agent, as compared to the control, indicates the agent is of use for treating cancer, Fanconi anemia, or a combination thereof.

26. The method of claim 25, wherein the *Xenopus* Fanconi anemia polypeptide comprises xFANCD2 or a functional fragment thereof, and wherein the post-translational modification is monoubiquination.

* * * * *

SEQUENCE LISTING

<160> NUMBER OF SEQ ID NOS: 13

<210> SEQ ID NO 1
<211> LENGTH: 1443
<212> TYPE: PRT
<213> ORGANISM: Xenopus laevis

<400> SEQUENCE: 1

```
Met Val Ala Lys Arg Lys Leu Ser Arg Ser Asp Asp Arg Glu Glu Ser
1               5                   10                  15

Phe Thr Ala Asp Thr Ser Lys Asn Lys Lys Cys Arg Thr Ser Ser Lys
            20                  25                  30

Lys Ser Lys Ala Leu Pro Gln Asp Gly Val Val Glu Asn Asp Ser Ile
        35                  40                  45

Phe Val Gln Leu Leu Lys Ser Ser Gly Met Thr Leu Lys Cys Gly Asp
    50                  55                  60

Arg Gln Asn Glu Ile Ala Val Asp Gln Ala Val Phe Gln Arg Lys Leu
65                  70                  75                  80

Gln Gln Ala Leu Arg Lys His Pro Arg His Pro Asn Val Ile Gln Glu
                85                  90                  95

Phe Ile Ser Gly Leu Glu Ser His Ile Glu Asp Arg Asp Ile Phe Arg
            100                 105                 110

Asn Cys Leu Leu Pro Cys Gly Asn Arg Gln Glu Thr Glu Ala Ser Thr
        115                 120                 125

Met Thr Gly Ser Phe His Asp Ser Leu Ile Lys Leu Leu Leu Gly Thr
    130                 135                 140

Asp Ile Leu Gln Glu Ser Val Ile Asn Thr Leu Phe Glu Lys Leu Pro
145                 150                 155                 160

Glu Phe Leu Tyr Asp Ser Val Gly Ser Asp Gly Ile Ser Ile Pro Arg
                165                 170                 175

Leu Ile Ile Asn Gln Phe Lys Trp Leu Asp Arg Ile Leu Asp Cys Lys
            180                 185                 190

Asp Leu Thr Leu Lys Ile Met Gln Leu Ile Ser Val Ala Pro Val Asp
        195                 200                 205

Ile Gln His Asp Ile Val Thr Ser Leu Pro Glu Ile Leu Glu Asp Ser
    210                 215                 220

Gln His Asn Asp Val Ala Arg Glu Leu Asn Ser Leu Leu Gln Gln Asn
225                 230                 235                 240

Thr Gln Leu Thr Val Pro Ile Leu Asp Ala Leu Ser Ser Leu Asn Ile
                245                 250                 255

Asn Ala Asp Leu Leu Ser Glu Val Arg Gln Ser Val Met Ser Thr Leu
            260                 265                 270

Ser Ala Val Glu Leu Glu Asp Leu Pro Val Ile Ile Lys Phe Ile Leu
```

```
                275                 280                 285
His Ala Val Thr Pro Ser Asp Ala Leu Glu Val Ile Ser Glu Leu Arg
        290                 295                 300
Lys Lys Leu Asp Leu Glu Ser Cys Ser Ser Leu Glu Gln Ile Tyr Ala
305                 310                 315                 320
Thr Gln Ser Lys Glu Arg Asn Lys Pro His Ala Gly Ser Ser Val Asn
                325                 330                 335
Lys Thr Lys Ser Ser Asp Cys Val Ser Leu Met Met Asp Val Ile Lys
            340                 345                 350
Ser Ser Val Arg Phe Gln Lys His Thr Ser Glu Ala Trp Met Lys Ala
        355                 360                 365
Ile Glu Asn Val Asp Thr Val Gly Asp His Lys Val Ser Asp Leu Ile
    370                 375                 380
Val Leu Leu Ile Leu Tyr Thr Thr Gln Thr Asn Ser Ser Lys Lys Gln
385                 390                 395                 400
Ala Glu Arg Val Leu Arg Asn Lys Ile Arg Ser Gly Phe Ile Leu Asp
                405                 410                 415
Gln Leu Leu Gln Asn Ala Phe Arg Asn His Ser Gln Val Leu Arg Asp
            420                 425                 430
Tyr Phe Pro Ser Ile Leu Ser Leu Ala Gln Ser Met Leu Arg Ser Ala
        435                 440                 445
Glu Gln Ser Val Val Ser Phe Gly Ser Leu Met Tyr Lys Ser Ala Phe
    450                 455                 460
Ser Ser Phe Asp Ser Tyr Cys Gln Gln Glu Val Val Gly Ala Leu Val
465                 470                 475                 480
Thr His Val Cys Ser Gly Tyr Ala Ala Glu Val Asp Val Ser Leu Asp
                485                 490                 495
Val Leu Thr Asp Leu Val Ser Ser His Ala Ala Val Ala Leu Tyr
            500                 505                 510
Ala Val Phe Val Lys Gly Ile Leu Asp Tyr Leu Asp Asn Leu Asn Ala
        515                 520                 525
Gln Gln Ile Arg Lys Leu Phe His Ile Leu Ser Val Leu Ala Phe Ser
    530                 535                 540
Arg Gly Gln Glu Gly Gly His Ile Gln Asp Asp Met Phe Ile Val Ile
545                 550                 555                 560
Arg Lys Gln Leu Ser Ser Thr Val Leu Lys Tyr Arg Ile Gly Ile
                565                 570                 575
Ile Gly Ala Val Gln Met Val Gly Ser Met Ala Met Asn Lys Lys His
            580                 585                 590
Gly Ser Lys His Pro Glu Asn Lys Pro Leu Ser Ala Glu Thr Phe Arg
        595                 600                 605
Gln Val Thr Ala Leu Leu Glu Leu Leu Gln Thr Cys Ser Glu Arg Val
    610                 615                 620
Ala Glu Ala Ser Ala Leu Tyr Tyr Asp Glu Leu Ser Ser Leu Val Gln
625                 630                 635                 640
Lys Arg Asn Leu Asp Pro Gln Val Met Ser Leu Val Gly Lys Thr Val
                645                 650                 655
Leu Thr Asp Phe Gln Asp Asp Phe Val Glu Asp Leu Thr Pro Thr Glu
            660                 665                 670
Glu Gly Asn Tyr Ile Phe Pro Leu Lys Ala Met Tyr Asn Leu Asp Glu
        675                 680                 685
Asp Asp Ser Gln Gly Gly Ile Ala Ile Asn Leu Leu Pro Leu Leu Ser
    690                 695                 700
```

-continued

```
Gln Asp Met Arg Asn Arg Gly Ala Glu Gln Val Ala Asn Lys Glu Gly
705                 710                 715                 720

Arg Val Val Ser Pro Ile Cys Leu Ser Pro Phe Phe Arg Leu Leu Arg
                725                 730                 735

Leu Cys Ile Glu Asp Gln His Glu Gly Asn Leu Glu Glu Ile Asp Ala
            740                 745                 750

Leu Leu Gly Cys Pro Leu Tyr Leu Thr Asp Leu Glu Ile Thr Glu Lys
            755                 760                 765

Met Glu Ser Leu Ser Lys Gln Glu Arg Glu Phe Leu Cys Ser Leu Leu
770                 775                 780

Phe Phe Ala Leu Asn Trp Phe Arg Glu Ile Val Asn Ala Phe Cys Lys
785                 790                 795                 800

Gln Gln Asp Pro Asp Met Lys Gly Lys Val Leu Thr Arg Leu Gln Asn
                805                 810                 815

Ile Thr Trp Leu Gln Ser Val Leu Glu Lys Cys Leu Ala Ala Ser Pro
            820                 825                 830

Gly Tyr Ile Pro Ser Ser Ala His Phe Asp Ser Glu Pro Gln Glu Val
            835                 840                 845

Leu Pro Ser Ala Ile Ala Pro Ala Pro Ala Lys Lys Ala Lys Lys Gly
850                 855                 860

Lys Thr Pro Lys Ser Ala Gly Ser Lys Asn Ala Ser Ala Asp Ser Ser
865                 870                 875                 880

Gln Leu Glu Glu His Met Asp Thr Glu Lys Ser Glu Leu Lys Thr
                885                 890                 895

Gln Pro Glu Lys Glu Lys Glu Ser Lys Pro Ser Ile Asn Leu Asn
                900                 905                 910

Asn Tyr Arg Ala Tyr Phe Arg Glu Leu Asp Leu Glu Val Phe Thr Val
            915                 920                 925

Leu Gln Cys Gly Leu Leu Thr Arg Ser Leu Leu Asp Ser Glu Met His
930                 935                 940

Thr Lys Ala Thr Glu Val Val Gln Leu Gly Pro Ala Glu Leu Val Phe
945                 950                 955                 960

Leu Leu Glu Asp Leu Phe Arg Lys Thr Glu Asn Ile Leu Thr Ser Ala
                965                 970                 975

Ala Lys Arg Val Thr Phe Leu Lys Val Lys Lys Gly Arg Asn Leu Gly
            980                 985                 990

Phe Ser Gln Leu Leu Gln Lys Thr Pro Gln Glu Val Ala Gln Ala Val
            995                 1000                1005

Ile His Leu Leu Asn Ser Leu Cys Asn His Ile Glu Asn Met His
    1010                1015                1020

Asn Tyr Phe Gln Thr Leu Met Leu Glu Asn His Gly Val Val Asp
    1025                1030                1035

Ala Pro Gly Val Asp Ile Lys Glu His Gln Tyr Met Ser Thr Cys
    1040                1045                1050

Tyr Gln Leu Leu Leu Gln Val Phe His Thr Leu Phe Cys Trp Asn
    1055                1060                1065

Gly Phe Ser Gln His Glu Asn Arg Lys Leu Leu Lys Ser Ala Leu
    1070                1075                1080

Ile Ala Leu Ala Gly Arg Leu Lys Glu Thr Glu Thr Glu Pro Ala
    1085                1090                1095

Leu Asp Asp Leu Val Arg Gln Ser Phe Asn Tyr Leu Lys Asn Leu
    1100                1105                1110

His Ser Ser Val Pro Thr Cys Ser Ser Ala Leu Cys Leu Thr Gln
    1115                1120                1125
```

```
Leu Leu Ile Val Ile Ala Glu Lys Thr Asn Val Leu Gln Tyr Arg
    1130            1135                1140

Glu Gln Ile Ala Ser Met Ala Lys Gln Phe Leu Cys Gln Ala Trp
    1145            1150                1155

Ile Gln Pro Ser Gly Glu Arg Glu Lys Gly Ile Arg Tyr His Glu
    1160            1165                1170

Asn Leu Gln Ser Leu Leu Cys Ile Tyr Leu Glu Asn Thr Asp Asp
    1175            1180                1185

Val Leu Lys Ala Val Glu Asp Ile Ala Gly Val Gly Val Pro Glu
    1190            1195                1200

Leu Val Asn Ala Ala Lys Asp Ala Ala Ser Ser Ser Tyr Pro Thr
    1205            1210                1215

Leu Thr Arg Gln Thr Phe Val Val Phe Arg Val Met Met Asp
    1220            1225                1230

Lys Leu Glu Lys Cys Val Lys Ser Ile Pro Asn Ser Lys Lys Ala
    1235            1240                1245

Glu Thr Leu Gln Glu Gln Thr Glu Gln Leu Leu Ser Trp Asn Leu
    1250            1255                1260

Ala Val Arg Asp Phe His Ile Leu Val Asn Leu Val Lys Val Phe
    1265            1270                1275

Asp Ser Arg Pro Val Leu Ser Ile Cys Leu Lys Tyr Gly Arg Leu
    1280            1285                1290

Phe Val Glu Thr Phe Leu Lys Leu Gly Met Pro Leu Leu Asp Cys
    1295            1300                1305

Cys Phe Lys Lys Gln Arg Glu Asp Val Gln Ser Leu Leu Lys Thr
    1310            1315                1320

Leu Gln Leu Ser Thr Arg Gln Leu His His Met Cys Gly His Ser
    1325            1330                1335

Lys Ile Asn Gln Asp Thr Ala Leu Thr Asn His Val Pro Leu Leu
    1340            1345                1350

Lys Lys Thr Leu Glu Leu Phe Val Tyr Arg Val Lys Ala Met Leu
    1355            1360                1365

Val Leu Asn Asn Cys Gln Glu Ala Phe Trp Leu Gly Asn Leu Lys
    1370            1375                1380

Asn Arg Asp Leu Gln Gly Glu Glu Ile Val Ser Gln Val Ser Gln
    1385            1390                1395

Glu Ser Glu Ala Glu Glu Glu Gln Glu Ser Gln Leu Pro Pro Glu
    1400            1405                1410

Glu Glu Glu Ala Glu Glu Glu Glu Asn Gly Ser Asp Lys
    1415            1420                1425

Glu Ile Glu Gly Gly Asp Glu Asp Asn Glu Asp Glu Asp Ser Asp
    1430            1435                1440

<210> SEQ ID NO 2
<211> LENGTH: 1471
<212> TYPE: PRT
<213> ORGANISM: Homo sapiens

<400> SEQUENCE: 2

Met Val Ser Lys Arg Arg Leu Ser Lys Ser Glu Asp Lys Glu Ser Leu
1               5                   10                  15

Thr Glu Asp Ala Ser Lys Thr Arg Lys Gln Pro Leu Ser Lys Lys Thr
                20                  25                  30

Lys Lys Ser His Ile Ala Asn Glu Val Glu Glu Asn Asp Ser Ile Phe
            35                  40                  45
```

```
Val Lys Leu Leu Lys Ile Ser Gly Ile Ile Leu Lys Thr Gly Glu Ser
    50                  55                  60

Gln Asn Gln Leu Ala Val Asp Gln Ile Ala Phe Gln Lys Lys Leu Phe
 65                  70                  75                  80

Gln Thr Leu Arg Arg His Pro Ser Tyr Pro Lys Ile Ile Glu Glu Phe
                85                  90                  95

Val Ser Gly Leu Glu Ser Tyr Ile Glu Asp Glu Asp Ser Phe Arg Asn
            100                 105                 110

Cys Leu Leu Ser Cys Glu Arg Leu Gln Asp Glu Glu Ala Ser Met Gly
            115                 120                 125

Ala Ser Tyr Ser Lys Ser Leu Ile Lys Leu Leu Gly Ile Asp Ile
        130                 135                 140

Leu Gln Pro Ala Ile Ile Lys Thr Leu Phe Glu Lys Leu Pro Glu Tyr
145                 150                 155                 160

Phe Phe Glu Asn Lys Asn Ser Asp Glu Ile Asn Ile Pro Arg Leu Ile
                165                 170                 175

Val Ser Gln Leu Lys Trp Leu Asp Arg Val Val Asp Gly Lys Asp Leu
            180                 185                 190

Thr Thr Lys Ile Met Gln Leu Ser Ile Ala Pro Glu Asn Leu Gln
        195                 200                 205

His Asp Ile Ile Thr Ser Leu Pro Glu Ile Leu Gly Asp Ser Gln His
        210                 215                 220

Ala Asp Val Gly Lys Glu Leu Ser Asp Leu Leu Ile Glu Asn Thr Ser
225                 230                 235                 240

Leu Thr Val Pro Ile Leu Asp Val Leu Ser Ser Leu Arg Leu Asp Pro
                245                 250                 255

Asn Phe Leu Leu Lys Val Arg Gln Leu Val Met Asp Lys Leu Ser Ser
            260                 265                 270

Ile Arg Leu Glu Asp Leu Pro Val Ile Ile Lys Phe Ile Leu His Ser
        275                 280                 285

Val Thr Ala Met Asp Thr Leu Glu Val Ile Ser Glu Leu Arg Glu Lys
290                 295                 300

Leu Asp Leu Gln His Cys Val Leu Pro Ser Arg Leu Gln Ala Ser Gln
305                 310                 315                 320

Val Lys Leu Lys Ser Lys Gly Arg Ala Ser Ser Ser Gly Asn Gln Glu
                325                 330                 335

Ser Ser Gly Gln Ser Cys Ile Ile Leu Leu Phe Asp Val Ile Lys Ser
            340                 345                 350

Ala Ile Arg Tyr Glu Lys Thr Ile Ser Glu Ala Trp Ile Lys Ala Ile
        355                 360                 365

Glu Asn Thr Ala Ser Val Ser Glu His Lys Val Phe Asp Leu Val Met
        370                 375                 380

Leu Phe Ile Ile Tyr Ser Thr Asn Thr Gln Thr Lys Lys Tyr Ile Asp
385                 390                 395                 400

Arg Val Leu Arg Asn Lys Ile Arg Ser Gly Cys Ile Gln Glu Gln Leu
                405                 410                 415

Leu Gln Ser Thr Phe Ser Val His Tyr Leu Val Leu Lys Asp Met Cys
            420                 425                 430

Ser Ser Ile Leu Ser Leu Ala Gln Ser Leu Leu His Ser Leu Asp Gln
        435                 440                 445

Ser Ile Ile Ser Phe Gly Ser Leu Leu Tyr Lys Tyr Ala Phe Lys Phe
        450                 455                 460

Phe Asp Thr Tyr Cys Gln Gln Glu Val Val Gly Ala Leu Val Thr His
```

```
            465                 470                 475                 480
Ile Cys Ser Gly Asn Glu Ala Glu Val Asp Thr Ala Leu Asp Val Leu
                    485                 490                 495

Leu Glu Leu Val Val Leu Asn Pro Ser Ala Met Met Met Asn Ala Val
            500                 505                 510

Phe Val Lys Gly Ile Leu Asp Tyr Leu Asp Asn Ile Ser Pro Gln Gln
            515                 520                 525

Ile Arg Lys Leu Phe Tyr Val Leu Ser Thr Leu Ala Phe Ser Lys Gln
            530                 535                 540

Asn Glu Ala Ser Ser His Ile Gln Asp Asp Met His Leu Val Ile Arg
545                 550                 555                 560

Lys Gln Leu Ser Ser Thr Val Phe Lys Tyr Lys Leu Ile Gly Ile Ile
                    565                 570                 575

Gly Ala Val Thr Met Ala Gly Ile Met Ala Ala Asp Arg Ser Glu Ser
                    580                 585                 590

Pro Ser Leu Thr Gln Glu Arg Ala Asn Leu Ser Asp Glu Gln Cys Thr
            595                 600                 605

Gln Val Thr Ser Leu Leu Gln Leu Val His Ser Cys Ser Glu Gln Ser
            610                 615                 620

Pro Gln Ala Ser Ala Leu Tyr Tyr Asp Glu Phe Ala Asn Leu Ile Gln
625                 630                 635                 640

His Glu Lys Leu Asp Pro Lys Ala Leu Glu Trp Val Gly His Thr Ile
                    645                 650                 655

Cys Asn Asp Phe Gln Asp Ala Phe Val Val Asp Ser Cys Val Val Pro
                    660                 665                 670

Glu Gly Asp Phe Pro Phe Pro Val Lys Ala Leu Tyr Gly Leu Glu Glu
            675                 680                 685

Tyr Asp Thr Gln Asp Gly Ile Ala Ile Asn Leu Leu Pro Leu Leu Phe
            690                 695                 700

Ser Gln Asp Phe Ala Lys Asp Gly Gly Pro Val Thr Ser Gln Glu Ser
705                 710                 715                 720

Gly Gln Lys Leu Val Ser Pro Leu Cys Leu Ala Pro Tyr Phe Arg Leu
                    725                 730                 735

Leu Arg Leu Cys Val Glu Arg Gln His Asn Gly Asn Leu Glu Glu Ile
                    740                 745                 750

Asp Gly Leu Leu Asp Cys Pro Ile Phe Leu Thr Asp Leu Glu Pro Gly
            755                 760                 765

Glu Lys Leu Glu Ser Met Ser Ala Lys Glu Arg Ser Phe Met Cys Ser
            770                 775                 780

Leu Ile Phe Leu Thr Leu Asn Trp Phe Arg Glu Ile Val Asn Ala Phe
785                 790                 795                 800

Cys Gln Glu Thr Ser Pro Glu Met Lys Gly Lys Val Leu Thr Arg Leu
                    805                 810                 815

Lys His Ile Val Glu Leu Gln Ile Ile Leu Glu Lys Tyr Leu Ala Val
                    820                 825                 830

Thr Pro Asp Tyr Val Pro Pro Leu Gly Asn Phe Asp Val Glu Thr Leu
            835                 840                 845

Asp Ile Thr Pro His Thr Val Thr Ala Ile Ser Ala Lys Ile Arg Lys
            850                 855                 860

Lys Gly Lys Ile Glu Arg Lys Gln Lys Thr Asp Gly Ser Lys Thr Ser
865                 870                 875                 880

Ser Ser Asp Thr Leu Ser Glu Glu Lys Asn Ser Glu Cys Asp Pro Thr
                    885                 890                 895
```

-continued

```
Pro Ser His Arg Gly Gln Leu Asn Lys Glu Phe Thr Gly Lys Glu
                900                 905                 910

Lys Thr Ser Leu Leu His Asn Ser His Ala Phe Phe Arg Glu Leu
            915                 920                 925

Asp Ile Glu Val Phe Ser Ile Leu His Cys Gly Leu Val Thr Lys Phe
930                 935                 940

Ile Leu Asp Thr Glu Met His Thr Glu Ala Thr Glu Val Val Gln Leu
945                 950                 955                 960

Gly Pro Pro Glu Leu Leu Phe Leu Leu Glu Asp Leu Ser Gln Lys Leu
                965                 970                 975

Glu Ser Met Leu Thr Pro Pro Ile Ala Arg Arg Val Pro Phe Leu Lys
            980                 985                 990

Asn Lys Gly Ser Arg Asn Ile Gly Phe Ser His Leu Gln Gln Arg Ser
                995                 1000                1005

Ala Gln Glu Ile Val His Cys Val Phe Gln Leu Leu Thr Pro Met
    1010                1015                1020

Cys Asn His Leu Glu Asn Ile His Asn Tyr Phe Gln Cys Leu Ala
    1025                1030                1035

Ala Glu Asn His Gly Val Val Asp Gly Pro Gly Val Lys Val Gln
    1040                1045                1050

Glu Tyr His Ile Met Ser Ser Cys Tyr Gln Arg Leu Leu Gln Ile
    1055                1060                1065

Phe His Gly Leu Phe Ala Trp Ser Gly Phe Ser Gln Pro Glu Asn
    1070                1075                1080

Gln Asn Leu Leu Tyr Ser Ala Leu His Val Leu Ser Ser Arg Leu
    1085                1090                1095

Lys Gln Gly Glu His Ser Gln Pro Leu Glu Glu Leu Leu Ser Gln
    1100                1105                1110

Ser Val His Tyr Leu Gln Asn Phe His Gln Ser Ile Pro Ser Phe
    1115                1120                1125

Gln Cys Ala Leu Tyr Leu Ile Arg Leu Leu Met Val Ile Leu Glu
    1130                1135                1140

Lys Ser Thr Ala Ser Ala Gln Asn Lys Glu Lys Ile Ala Ser Leu
    1145                1150                1155

Ala Arg Gln Phe Leu Cys Arg Val Trp Pro Ser Gly Asp Lys Glu
    1160                1165                1170

Lys Ser Asn Ile Ser Asn Asp Gln Leu His Ala Leu Leu Cys Ile
    1175                1180                1185

Tyr Leu Glu His Thr Glu Ser Ile Leu Lys Ala Ile Glu Glu Ile
    1190                1195                1200

Ala Gly Val Gly Val Pro Glu Leu Ile Asn Ser Pro Lys Asp Ala
    1205                1210                1215

Ser Ser Ser Thr Phe Pro Thr Leu Thr Arg His Thr Phe Val Val
    1220                1225                1230

Phe Phe Arg Val Met Met Ala Glu Leu Glu Lys Thr Val Lys Lys
    1235                1240                1245

Ile Glu Pro Gly Thr Ala Ala Asp Ser Gln Gln Ile His Glu Glu
    1250                1255                1260

Lys Leu Leu Tyr Trp Asn Met Ala Val Arg Asp Phe Ser Ile Leu
    1265                1270                1275

Ile Asn Leu Ile Lys Val Phe Asp Ser His Pro Val Leu His Val
    1280                1285                1290

Cys Leu Lys Tyr Gly Arg Leu Phe Val Glu Ala Phe Leu Lys Gln
    1295                1300                1305
```

```
Cys Met Pro Leu Leu Asp Phe Ser Phe Arg Lys His Arg Glu Asp
    1310            1315                1320

Val Leu Ser Leu Leu Glu Thr Phe Gln Leu Asp Thr Arg Leu Leu
    1325            1330                1335

His His Leu Cys Gly His Ser Lys Ile His Gln Asp Thr Arg Leu
    1340            1345                1350

Thr Gln His Val Pro Leu Leu Lys Lys Thr Leu Glu Leu Leu Val
    1355            1360                1365

Cys Arg Val Lys Ala Met Leu Thr Leu Asn Asn Cys Arg Glu Ala
    1370            1375                1380

Phe Trp Leu Gly Asn Leu Lys Asn Arg Asp Leu Gln Gly Glu Glu
    1385            1390                1395

Ile Lys Ser Gln Asn Ser Gln Glu Ser Thr Ala Asp Glu Ser Glu
    1400            1405                1410

Asp Asp Met Ser Ser Gln Ala Ser Lys Ser Lys Ala Thr Glu Val
    1415            1420                1425

Ser Leu Gln Asn Pro Pro Glu Ser Gly Thr Asp Gly Cys Ile Leu
    1430            1435                1440

Leu Ile Val Leu Ser Trp Trp Ser Arg Thr Leu Pro Thr Tyr Val
    1445            1450                1455

Tyr Cys Gln Met Leu Leu Cys Pro Phe Pro Phe Pro Pro
    1460            1465                1470
```

<210> SEQ ID NO 3
<211> LENGTH: 70
<212> TYPE: DNA
<213> ORGANISM: Artificial sequence
<220> FEATURE:
<223> OTHER INFORMATION: Synthetic nucleic acid

<400> SEQUENCE: 3
gggggggggg gggggggggg gggggggggg gggggggggg aaaaaaaaaa aaaaaaaaaa    60
aaaaaaaaaa                                                           70

<210> SEQ ID NO 4
<211> LENGTH: 70
<212> TYPE: DNA
<213> ORGANISM: Artificial sequence
<220> FEATURE:
<223> OTHER INFORMATION: Synthetic nucleic acid

<400> SEQUENCE: 4
tttttttttt tttttttttt tttttttttt cccccccccc cccccccccc cccccccccc    60
cccccccccc                                                           70

<210> SEQ ID NO 5
<211> LENGTH: 70
<212> TYPE: DNA
<213> ORGANISM: Artificial sequence
<220> FEATURE:
<223> OTHER INFORMATION: Synthetic nucleic acid

<400> SEQUENCE: 5
aaaaaaaaaa aaaaaaaaaa aaaaaaaaaa cccccccccc cccccccccc cccccccccc    60
cccccccccc                                                           70

<210> SEQ ID NO 6
<211> LENGTH: 30
<212> TYPE: DNA

<213> ORGANISM: Artificial sequence
<220> FEATURE:
<223> OTHER INFORMATION: Synthetic nucleic acid

<400> SEQUENCE: 6
tttttttttt tttttttttt tttttttttt                              30

<210> SEQ ID NO 7
<211> LENGTH: 59
<212> TYPE: DNA
<213> ORGANISM: Artificial sequence
<220> FEATURE:
<223> OTHER INFORMATION: Synthetic nucleic acid

<400> SEQUENCE: 7
ggttgacgtt ctagtgtgac cgcaatacgg ataagggctg agcacgccga cgaacatac    59

<210> SEQ ID NO 8
<211> LENGTH: 65
<212> TYPE: DNA
<213> ORGANISM: Artificial sequence
<220> FEATURE:
<223> OTHER INFORMATION: Synthetic nucleic acid

<400> SEQUENCE: 8
gtatgttcgt cggcgtgctc agcccttatc cagaatgca ccaacagttc ctcaagatag    60
agact                                                                65

<210> SEQ ID NO 9
<211> LENGTH: 75
<212> TYPE: DNA
<213> ORGANISM: Artificial sequence
<220> FEATURE:
<223> OTHER INFORMATION: Synthetic nucleic acid

<400> SEQUENCE: 9
gagtctctat cttgaggaac tgttggtgca ttctgggata agggcactat ggctccactg    60
atgtcgtaag catcc                                                     75

<210> SEQ ID NO 10
<211> LENGTH: 68
<212> TYPE: DNA
<213> ORGANISM: Artificial sequence
<220> FEATURE:
<223> OTHER INFORMATION: Synthetic nucleic acid

<400> SEQUENCE: 10
ggatgcttac gacatcagtg gagccatagt gcccttatcc gtattgcggt cacactagaa    60
cgtcaacc                                                             68

<210> SEQ ID NO 11
<211> LENGTH: 68
<212> TYPE: DNA
<213> ORGANISM: Artificial sequence
<220> FEATURE:
<223> OTHER INFORMATION: Synthetic nucleic acid

<400> SEQUENCE: 11
ggttgacgtt ctagtgtgac cgcaatacgg ataagggcac tatggctcca ctgatgtcgt    60
aagcatcc                                                             68

<210> SEQ ID NO 12
<211> LENGTH: 1998
<212> TYPE: PRT

<213> ORGANISM: Xenopus tropicalis
<220> FEATURE:
<221> NAME/KEY: misc_feature
<222> LOCATION: (457)..(467)
<223> OTHER INFORMATION: Xaa can be any naturally occurring amino acid

<400> SEQUENCE: 12

```
Met Ser Gly Lys Gln Lys Thr Leu Phe Gln Thr Trp Gly Asn Asn Gln
1               5                   10                  15

Pro Pro Glu Thr Arg Lys Ala Lys Glu Thr Lys Pro Arg Lys Ala Arg
            20                  25                  30

Gln Gln Pro Ser Thr Cys Gln Gln Val Glu Asp Asp Asp Asp
        35                  40                  45

Val Leu Leu Val Ala Val Tyr Glu Ala Glu Lys Thr Leu Asn Gln Ser
    50                  55                  60

Gly Ile Leu Asn Gly Glu Ala Gly Ser Val Trp Ile Tyr Pro Thr Asn
65                  70                  75                  80

Tyr Leu Ile Arg Asp Tyr Gln Phe Asn Ile Ser Tyr Thr Ala Leu Leu
                85                  90                  95

Gln Asn Thr Leu Val Cys Leu Pro Thr Gly Leu Gly Lys Thr Phe Ile
            100                 105                 110

Ala Ala Val Val Met Tyr Asn Phe Tyr Arg Trp Tyr Pro Ser Gly Lys
        115                 120                 125

Ile Val Phe Met Ala Pro Thr Lys Pro Leu Val Ala Gln Gln Ile Glu
    130                 135                 140

Ala Cys Phe Arg Val Met Gly Ile Pro Gln Asp His Met Ala Glu Met
145                 150                 155                 160

Thr Gly Ser Thr Gln Ala Gln Asn Arg Lys Asp Met Trp Glu Lys His
                165                 170                 175

Arg Val Phe Phe Leu Thr Pro Gln Val Met Val Asn Asp Leu Thr Arg
            180                 185                 190

Gly Ala Cys Pro Ala Ser Glu Ile Lys Cys Leu Val Ile Asp Glu Ala
        195                 200                 205

His Lys Ala Leu Gly Asn His Ala Tyr Cys Gln Val Val Arg Glu Leu
    210                 215                 220

Thr Asn Tyr Thr Asn Gln Phe Arg Ile Leu Ala Leu Ser Ala Thr Pro
225                 230                 235                 240

Gly Gly Asp Thr Lys Ser Val Gln Gln Val Val Ser Asn Leu Leu Ile
                245                 250                 255

Ser Gln Ile Glu Leu Arg Ser Glu Asp Ser Pro Asp Ile Gln Pro Tyr
            260                 265                 270

Ser His Glu Arg Gln Leu Glu Lys Phe Val Val Pro Leu Gly Glu Glu
        275                 280                 285

Leu Glu Ser Val Gln Lys Thr Tyr Leu Gln Val Leu Glu Thr Phe Ala
    290                 295                 300

Gly Arg Leu Leu Lys Asn Asn Val Leu Ser Arg Arg Asp Ile Pro Asn
305                 310                 315                 320

Leu Thr Lys Tyr Gln Ile Ile Leu Ser Arg Asp Gln Phe Arg Lys Asn
                325                 330                 335

Pro Pro Ala Asn Ile Ile Val Ala Gln Gln Gly Val Ile Glu Gly Asp
            340                 345                 350

Phe Ala Leu Cys Ile Ser Leu Tyr His Gly Tyr Glu Leu Leu Leu Gln
        355                 360                 365

Met Gly Thr Arg Ser Leu Tyr Ser Tyr Leu His Gly Ile Met Asp Gly
    370                 375                 380
```

```
Ser Lys Gly Met Thr Arg Ala Arg Asn Glu Leu Ser Arg Asn Gly Asp
385                 390                 395                 400

Phe Met Glu Leu Tyr Gln Gln Leu Glu Asn Met Phe Ser Asp Leu Asn
            405                 410                 415

Val Thr Glu Gly Asn Gly Ser Leu Leu Phe Asn Thr Asn Ala Lys Lys
        420                 425                 430

Pro Phe Val Tyr Ser His Pro Lys Leu Ile Lys Leu Glu Asp Val Val
            435                 440                 445

Ile Gln His Phe Lys Ser Trp Asn Xaa Xaa Xaa Xaa Xaa Xaa Xaa
    450                 455                 460

Xaa Xaa Xaa Thr Arg Ile Met Ile Phe Ser Ser Phe Arg Asp Ser Val
465                 470                 475                 480

Gln Glu Ile Ala Glu Met Leu Asn Gln His His Pro Thr Val Arg Val
            485                 490                 495

Met Thr Phe Val Gly His Ser Ser Ala Gly Lys Gly Val Lys Gly Phe
        500                 505                 510

Thr Gln Lys Glu Gln Leu Glu Val Val Lys Arg Phe Arg Glu Gly Gly
        515                 520                 525

Phe Asn Thr Leu Val Ser Thr Cys Val Gly Glu Glu Gly Leu Asp Ile
530                 535                 540

Gly Glu Val Asp Leu Ile Ile Cys Phe Asp Ala Gln Lys Ser Pro Ile
545                 550                 555                 560

Arg Leu Val Gln Arg Met Gly Arg Thr Gly Arg Lys Arg Gln Gly Arg
            565                 570                 575

Ile Val Val Ile Leu Cys Gln Gly Arg Glu Glu Arg Thr Tyr Asn Gln
        580                 585                 590

Ser Gln Ser Asn Lys Arg Ser Ile Phe Lys Ala Ile Leu Gly Asn Asn
        595                 600                 605

Lys Met Leu His Leu Asn Pro Gln Ser Pro Arg Met Val Pro Glu Gly
            610                 615                 620

Leu Asn Pro Lys Val His Lys Met Phe Ile Thr Gln Gly Asn Tyr Glu
625                 630                 635                 640

Ala Lys Glu Ser Ile Arg Pro Lys His Lys Asp Arg Arg Ser Ser Thr
            645                 650                 655

Lys His Cys Asn Ser Ser Leu Phe Leu Asn Ala Ser Asp Thr Leu Lys
        660                 665                 670

Glu Glu Trp Asp Leu Thr His Ala Glu Phe Glu Thr Trp Asn Arg Leu
        675                 680                 685

Tyr Arg Leu Gln Glu Ser Asp Gly Ile Met Asp Val Arg Leu Pro Lys
            690                 695                 700

Ser Gln Phe Glu Tyr Phe Arg Asp Ala Glu Pro Asn Lys Glu Arg Pro
705                 710                 715                 720

Ser Gly Asn Ile His Lys Leu Ser Leu Thr Glu Trp Arg Val Trp Gln
            725                 730                 735

Asn Arg Pro Phe Pro Thr Asp Ser Val Asp His Ser Asp Arg Cys Lys
        740                 745                 750

Asn Phe Ile His Val Met Glu Met Ile Glu Leu Met Arg Leu Glu Glu
        755                 760                 765

Gly Asp Cys Asn Tyr Asp Leu Glu Met Met Ser Tyr Leu Asn Lys Glu
770                 775                 780

Asp Val Asp Pro Thr Ala Thr Asn Thr Arg Ala Ile Asn Val Leu Asp
785                 790                 795                 800

Asn Asn Ser Lys Val Ala Glu Lys Ser Thr His Pro Lys Lys Gly Lys
            805                 810                 815
```

-continued

Thr Tyr Lys Asn Thr Pro Leu Ser Leu Val Leu Glu Pro Asp Glu Asp
            820                 825                 830

Phe Met Ser Ser Cys Lys Lys Ile Thr Lys Ser His Ser Thr Asp Phe
            835                 840                 845

Val Ala Val Asp Ser Lys Val His Ala Gln Gly Thr Glu Glu Gly Gly
    850                 855                 860

Ser Thr Glu Leu Glu Arg Val Val Gly Leu Asn Glu Asp Asp His Gly
865                 870                 875                 880

Lys Glu Ser Val Phe Ser Ala Asn Val Thr Lys Tyr Lys Asp Ser Arg
                885                 890                 895

Ser Asn Ala Val Thr Ser Asn Gln Ser Asp Ser Asp His Met Leu Leu
                900                 905                 910

Ser Asp Thr Glu Asp Ala Val Ala Lys Ser Gln Ser Asn Val Asp Ala
            915                 920                 925

Lys Ala Asp Ser Gly Tyr His Ser Phe Asn Glu Asp Pro Ser Ser Asn
    930                 935                 940

Leu Ser Asn Leu Phe Tyr Thr Pro Gln Ser Phe Ile Asn His Gly Val
945                 950                 955                 960

Phe Thr Glu Phe Val Asp Asn Lys Ile Cys Glu Leu Lys Lys Met Leu
                965                 970                 975

Leu His Ile Lys Arg Phe Leu Ser His Ser Pro Pro Ile Asn Glu
            980                 985                 990

Leu Asp Cys Leu Asp Asp Phe Gln Lys Tyr Glu Asn Phe Ser His His
            995                1000                1005

Ser Cys Leu Ser Asp Pro Val Lys Asp Lys Thr Gln Glu Asp Leu
    1010                1015                1020

Leu Leu Gln Pro Leu Thr Gln Pro Leu Thr Pro Val Pro Val
    1025                1030                1035

Thr Ile Asn Ser Lys Glu Met Gln Ala Glu Leu Asn His Lys Lys
    1040                1045                1050

Gln Thr Asp Ser Val Ala Gly Thr Leu Leu Pro Ala Thr Glu Val
    1055                1060                1065

Lys Lys Asp Asp Val Leu Phe Gly Glu Asp Arg Leu Lys Pro Arg
    1070                1075                1080

Asp Val Ile Gln Thr Val Gly Gly Lys Ala Ala Cys Ser Glu Lys
    1085                1090                1095

Asn Val Gly Phe Tyr Ser Glu Asp Ser Ser Lys Pro Ser Ser Ser
    1100                1105                1110

Lys Asp Leu His Asp Val Arg Thr Glu Asn Asp Asp His Trp Asp
    1115                1120                1125

Glu Leu Phe Asp Tyr Glu Ser Gln Asp Lys Glu Asn Glu Asn Phe
    1130                1135                1140

Thr Phe Gln Val Asn Met Pro Val Leu Glu Gly Gly Asp Thr Glu
    1145                1150                1155

Gly Ser Ser Ala Glu Asn Glu Asn His Asn Ile Asp Ser Val Pro
    1160                1165                1170

Thr Phe Leu Glu Asp Ser Phe Asp Leu Phe Glu Glu Asp Gly Phe
    1175                1180                1185

Ser Asp Asn Ala Asn Tyr Gly Gln Leu His Ser Lys His Glu Ser
    1190                1195                1200

Thr Asp Lys Pro His Glu Asn Ala Lys Thr Thr Val Thr Phe Asn
    1205                1210                1215

Met Phe Asp Pro Ser Ser Leu Leu Gln Glu Gln Val Gln Thr Glu

```
                    1220                1225                1230
Asp Glu Pro Glu Thr Lys Asp Asp Ile Trp Ser Gln Glu Asn Leu
            1235                1240                1245
Glu Glu Leu Asp Cys Ser Glu Glu Leu Tyr Ser Val Asn Phe Asp
            1250                1255                1260
Leu Gly Phe Ser Ile Glu Asp Glu Leu Ser Glu Ser Asp Gly
            1265                1270                1275
Lys Asn Glu Thr Pro Ser Lys Asp Ser Lys Asp Glu Leu Ser
            1280                1285                1290
Glu Ile Asp Ser Lys Asn Glu Thr Pro Ser Lys Asp Ser Lys Asp
            1295                1300                1305
Asp Asn Leu Ser Asp Ser Lys Asn Val Thr Pro Ser Lys Asp Phe
            1310                1315                1320
Lys Val Pro Asn Pro Leu Lys Arg Asn Asp Met Asn Ala Ile Gly
            1325                1330                1335
Gly Asn Ala Val Ser Thr Pro Val Val Ser Ser Asn Ile Cys Ser
            1340                1345                1350
Thr Phe Ser Glu Val Ala Glu Lys Gln Ile His Leu Phe Ser Pro
            1355                1360                1365
Leu Glu Pro Val Arg Gly Lys Ile Ser Leu Thr Pro Glu Lys Ser
            1370                1375                1380
Leu Cys Ser Ser Ser Phe Phe Thr Pro Ile Gly Glu Lys Phe Arg
            1385                1390                1395
Ser Pro Gln Thr Pro Leu Gly Asn Leu Cys Asp Ser Glu Ala Gly
            1400                1405                1410
Glu Leu Gln Ser Pro Lys Ala Gly Glu Lys Ser Ile His Ser Thr
            1415                1420                1425
Thr Asn Phe Ser Val His Asp Gly Arg Val Val Gln Ala Glu Arg
            1430                1435                1440
Arg Gln Thr Asn Ser Cys Ser Glu His Ser Leu Ile Glu Ser Ser
            1445                1450                1455
Pro Glu Ser Glu Asp Asp Val Val Ile Cys Arg Lys Arg Lys Leu
            1460                1465                1470
Thr Lys Ala Asn Val Leu Met Ser Pro Gln Thr Ala Ser Ser Asp
            1475                1480                1485
Cys Asp Phe Asp Ser Pro Ile Pro Thr Ala Lys Lys Arg Arg His
            1490                1495                1500
Val Leu Lys Thr Pro Asp Ser Asp Glu Glu Glu Glu Asp Asp
            1505                1510                1515
Phe Lys Ser Thr His Ser Thr Ala Arg Asp Lys Ser Ala Gly His
            1520                1525                1530
Ser Arg Lys Ser Tyr Gln His Arg Ala Ile Ala Val Ser Lys Lys
            1535                1540                1545
Arg Lys Arg Cys Lys Gln Arg Ala Arg Gln Phe Leu Asp Glu Glu
            1550                1555                1560
Ala Glu Leu Ser Ser Glu Gly Ala Glu Phe Val Ser Ser Asp Glu
            1565                1570                1575
Asp Met Asn Ser Asp Asn Glu Gln Asp Thr Ser Leu Val Glu Phe
            1580                1585                1590
Leu Asn Asp Asp Pro Gln Leu Ser Gln Ala Leu Asn Asp Ser Glu
            1595                1600                1605
Met His Gly Val Tyr Leu Lys Ser Val Arg Ser Pro Ala Phe Gly
            1610                1615                1620
```

```
Gly Arg Phe Lys Met Ala Pro Gln Arg Arg His Asn Met Ser
1625                1630                1635

Val Phe Ser Gln Ile Pro Glu Gln Asp Glu Ser Tyr Met Glu Asp
    1640                1645                1650

Ser Phe Cys Val Gln Glu Glu Asp Asp Glu Glu Glu Ala Asp Asn
    1655                1660                1665

Leu Gly Ser Ser Glu Glu Glu Val Glu Ile Asn Phe Asp Leu Leu
    1670                1675                1680

Lys Asp Val Ser Ile Val Gly Gly Lys Lys Gln Tyr Cys Thr Arg
    1685                1690                1695

Arg Arg Leu Lys Leu Lys Glu Ala Gln Ser Arg Gln Leu Phe Leu
    1700                1705                1710

Ser Ser Gly Gln Leu Pro Asp Leu Leu Leu Ile Ser Tyr Leu
    1715                1720                1725

Pro Glu Glu Val Ser Ile Gly Arg Val Asn Phe Asp Leu Thr Met
    1730                1735                1740

Asp Ser Ser Ala Val Ala Asn Leu Ser Phe Pro Gly Thr Val Gly
    1745                1750                1755

Val Ser Ala Leu Ala Gly Ile Arg Thr Leu Cys Ile Leu Ala Asp
    1760                1765                1770

Ser Arg Glu Ile Ser Ser Gly Pro Glu Val Ile Ser Tyr Leu Lys
    1775                1780                1785

Met Ser Leu Gly Val Lys Val Glu Val Cys Ser Leu Gly Gly Cys
    1790                1795                1800

Asp Tyr Ile Val Ser Ser Arg Leu Ala Val Glu Arg Lys Ser Gln
    1805                1810                1815

Ser Glu Phe Ala Asn Ser Ala Asn Arg Ser Lys Leu Val Asp Arg
    1820                1825                1830

Ile Gln His Leu Gln His Leu Phe Asp Arg Val Cys Leu Ile Ile
    1835                1840                1845

Glu Lys Asp Arg Ile Lys Gln Gly Glu Thr Ser Arg Thr Phe Gln
    1850                1855                1860

Arg Thr Arg Tyr Tyr Asp Ser Thr Leu Ser Ala Leu Ile Ser Ala
    1865                1870                1875

Gly Val Gln Val Leu Phe Ser Ser Ser Gln Glu Glu Thr Ala Gly
    1880                1885                1890

Leu Leu Lys Glu Leu Gly Leu Leu Glu Gln Arg Lys Asn Thr Gly
    1895                1900                1905

Ile Asp Val Pro Thr Glu Val Lys Gly His Lys Gln Glu Val Met
    1910                1915                1920

Gln Phe Tyr Leu Ser Ile Pro Asn Ile Ser Tyr Ile Thr Ala Leu
    1925                1930                1935

Asn Leu Cys Gln Arg Phe Asp Ser Ile Arg Gln Met Ala Asn Ser
    1940                1945                1950

Ser Val Gln Val Ile Ser Ala Arg Ala His Val Ser Ala Gln Lys
    1955                1960                1965

Ala Glu Glu Leu Tyr Arg Tyr Val His Tyr Met Phe Glu Ala Glu
    1970                1975                1980

Met Val Ala Ser Glu Asn Pro Ala Lys Arg Ser Arg Val Ser Glx
    1985                1990                1995

<210> SEQ ID NO 13
<211> LENGTH: 2048
<212> TYPE: PRT
<213> ORGANISM: Homo sapiens
```

<400> SEQUENCE: 13

```
Met Ser Gly Arg Gln Arg Thr Leu Phe Gln Thr Trp Gly Ser Ser Ile
1               5                   10                  15

Ser Arg Ser Ser Gly Thr Pro Gly Cys Ser Ser Gly Thr Glu Arg Pro
            20                  25                  30

Gln Ser Pro Gly Ser Ser Lys Ala Pro Leu Pro Ala Ala Ala Glu Ala
        35                  40                  45

Gln Leu Glu Ser Asp Asp Val Leu Leu Val Ala Ala Tyr Glu Ala
50                  55                  60

Glu Arg Gln Leu Cys Leu Glu Asn Gly Gly Phe Cys Thr Ser Ala Gly
65                  70                  75                  80

Ala Leu Trp Ile Tyr Pro Thr Asn Cys Pro Val Arg Asp Tyr Gln Leu
                85                  90                  95

His Ile Ser Arg Ala Ala Leu Phe Cys Asn Thr Leu Val Cys Leu Pro
            100                 105                 110

Thr Gly Leu Gly Lys Thr Phe Ile Ala Ala Val Val Met Tyr Asn Phe
        115                 120                 125

Tyr Arg Trp Phe Pro Ser Gly Lys Val Val Phe Met Ala Pro Thr Lys
130                 135                 140

Pro Leu Val Thr Gln Gln Ile Glu Ala Cys Tyr Gln Val Met Gly Ile
145                 150                 155                 160

Pro Gln Ser His Met Ala Glu Met Thr Gly Ser Thr Gln Ala Ser Thr
                165                 170                 175

Arg Lys Glu Ile Trp Cys Ser Lys Arg Val Leu Phe Leu Thr Pro Gln
            180                 185                 190

Val Met Val Asn Asp Leu Ser Arg Gly Ala Cys Pro Ala Ala Glu Ile
        195                 200                 205

Lys Cys Leu Val Ile Asp Glu Ala His Lys Ala Leu Gly Asn Tyr Ala
210                 215                 220

Tyr Cys Gln Val Val Arg Glu Leu Val Lys Tyr Thr Asn His Phe Arg
225                 230                 235                 240

Ile Leu Ala Leu Ser Ala Thr Pro Gly Ser Asp Ile Lys Ala Val Gln
                245                 250                 255

Gln Val Ile Thr Asn Leu Leu Ile Gly Gln Ile Glu Leu Arg Ser Glu
            260                 265                 270

Asp Ser Pro Asp Ile Leu Thr Tyr Ser His Glu Arg Lys Val Glu Lys
        275                 280                 285

Leu Ile Val Pro Leu Gly Glu Glu Leu Ala Ala Ile Gln Lys Thr Tyr
290                 295                 300

Ile Gln Ile Leu Glu Ser Phe Ala Arg Ser Leu Ile Gln Arg Asn Val
305                 310                 315                 320

Leu Met Arg Arg Asp Ile Pro Asn Leu Thr Lys Tyr Gln Ile Ile Leu
                325                 330                 335

Ala Arg Asp Gln Phe Arg Lys Asn Pro Ser Pro Asn Ile Val Gly Ile
            340                 345                 350

Gln Gln Gly Ile Ile Glu Gly Glu Phe Ala Ile Cys Ile Ser Leu Tyr
        355                 360                 365

His Gly Tyr Glu Leu Leu Gln Gln Met Gly Met Arg Ser Leu Tyr Phe
370                 375                 380

Phe Leu Cys Gly Ile Met Asp Gly Thr Lys Gly Met Thr Arg Ser Lys
385                 390                 395                 400

Asn Glu Leu Gly Arg Asn Glu Asp Phe Met Lys Leu Tyr Asn His Leu
                405                 410                 415
```

```
Glu Cys Met Phe Ala Arg Thr Arg Ser Thr Ser Ala Asn Gly Ile Ser
                420                 425                 430

Ala Ile Gln Gln Gly Asp Lys Asn Lys Lys Phe Val Tyr Ser His Pro
            435                 440                 445

Lys Leu Lys Lys Leu Glu Glu Val Val Ile Glu His Phe Lys Ser Trp
450                 455                 460

Asn Ala Glu Asn Thr Thr Glu Lys Lys Arg Asp Glu Thr Arg Val Met
465                 470                 475                 480

Ile Phe Ser Ser Phe Arg Asp Ser Val Gln Glu Ile Ala Glu Met Leu
                485                 490                 495

Ser Gln His Gln Pro Ile Ile Arg Val Met Thr Phe Val Gly His Ala
            500                 505                 510

Ser Gly Lys Ser Thr Lys Gly Phe Thr Gln Lys Glu Gln Leu Glu Val
            515                 520                 525

Val Lys Gln Phe Arg Asp Gly Tyr Asn Thr Leu Val Ser Thr Cys
530                 535                 540

Val Gly Glu Glu Gly Leu Asp Ile Gly Glu Val Asp Leu Ile Ile Cys
545                 550                 555                 560

Phe Asp Ser Gln Lys Ser Pro Ile Arg Leu Val Gln Arg Met Gly Arg
                565                 570                 575

Thr Gly Arg Lys Arg Gln Gly Arg Ile Val Ile Leu Ser Glu Gly
            580                 585                 590

Arg Glu Glu Arg Ile Tyr Asn Gln Ser Gln Ser Asn Lys Arg Ser Ile
            595                 600                 605

Tyr Lys Ala Ile Ser Ser Asn Arg Gln Val Leu His Phe Tyr Gln Arg
610                 615                 620

Ser Pro Arg Met Val Pro Asp Gly Ile Asn Pro Lys Leu His Lys Met
625                 630                 635                 640

Phe Ile Thr His Gly Val Tyr Glu Pro Glu Lys Pro Ser Arg Asn Leu
                645                 650                 655

Gln Arg Lys Ser Ser Ile Phe Ser Tyr Arg Asp Gly Met Arg Gln Ser
            660                 665                 670

Ser Leu Lys Lys Asp Trp Phe Leu Ser Glu Glu Phe Lys Leu Trp
            675                 680                 685

Asn Arg Leu Tyr Arg Leu Arg Asp Ser Asp Glu Ile Lys Glu Ile Thr
690                 695                 700

Leu Pro Gln Val Gln Phe Ser Ser Leu Gln Asn Glu Glu Asn Lys Pro
705                 710                 715                 720

Ala Gln Glu Ser Thr Thr Gly Ile His Gln Leu Ser Leu Ser Glu Trp
                725                 730                 735

Arg Leu Trp Gln Asp His Pro Leu Pro Thr His Gln Val Asp His Ser
            740                 745                 750

Asp Arg Cys Arg His Phe Ile Gly Leu Met Gln Met Ile Glu Gly Met
            755                 760                 765

Arg His Glu Glu Gly Glu Cys Ser Tyr Glu Leu Glu Val Glu Ser Tyr
            770                 775                 780

Leu Gln Met Glu Asp Val Thr Ser Thr Phe Ile Ala Pro Arg Asn Glu
785                 790                 795                 800

Ser Asn Asn Leu Ala Ser Asp Thr Phe Ile Thr His Lys Lys Ser Ser
                805                 810                 815

Phe Ile Lys Asn Ile Asn Gln Gly Ser Ser Ser Val Ile Glu Ser
            820                 825                 830

Asp Glu Glu Cys Ala Glu Ile Val Lys Gln Thr His Ile Lys Pro Thr
```

-continued

```
            835                 840                 845
Lys Ile Val Ser Leu Lys Lys Val Ser Lys Glu Ile Lys Lys Asp
        850                 855                 860
Gln Leu Lys Lys Glu Asn Asn His Gly Ile Ile Asp Ser Val Asp Asn
865                 870                 875                 880
Asp Arg Asn Ser Thr Val Glu Asn Ile Phe Gln Glu Asp Leu Pro Asn
                    885                 890                 895
Asp Lys Arg Thr Ser Asp Thr Asp Glu Ile Ala Ala Thr Cys Thr Ile
            900                 905                 910
Asn Glu Asn Val Ile Lys Glu Pro Cys Val Leu Leu Thr Glu Cys Gln
            915                 920                 925
Phe Thr Asn Lys Ser Thr Ser Ser Leu Ala Gly Asn Val Leu Asp Ser
    930                 935                 940
Gly Tyr Asn Ser Phe Asn Asp Glu Lys Ser Val Ser Ser Asn Leu Phe
945                 950                 955                 960
Leu Pro Phe Glu Glu Leu Tyr Ile Val Arg Thr Asp Asp Gln Phe
        965                 970                 975
Tyr Asn Cys His Ser Leu Thr Lys Glu Val Leu Ala Asn Val Glu Arg
                980                 985                 990
Phe Leu Ser Tyr Ser Pro Pro Pro Leu Ser Gly Leu Ser Asp Leu Glu
            995                 1000                1005
Tyr Glu Ile Ala Lys Gly Thr Ala Leu Glu Asn Leu Leu Phe Leu
    1010                1015                1020
Pro Cys Ala Glu His Leu Arg Ser Asp Lys Cys Thr Cys Leu Leu
    1025                1030                1035
Ser His Ser Ala Val Asn Ser Gln Gln Asn Leu Glu Leu Asn Ser
    1040                1045                1050
Leu Lys Cys Ile Asn Tyr Pro Ser Glu Lys Ser Cys Leu Tyr Asp
    1055                1060                1065
Ile Pro Asn Asp Asn Ile Ser Asp Glu Pro Ser Leu Cys Asp Cys
    1070                1075                1080
Asp Val His Lys His Asn Gln Asn Glu Asn Leu Val Pro Asn Asn
    1085                1090                1095
Arg Val Gln Ile His Arg Ser Pro Ala Gln Asn Leu Val Gly Glu
    1100                1105                1110
Asn Asn His Asp Val Asp Asn Ser Asp Leu Pro Val Leu Ser Thr
    1115                1120                1125
Asp Gln Asp Glu Ser Leu Leu Leu Phe Glu Asp Val Asn Thr Glu
    1130                1135                1140
Phe Asp Asp Val Ser Leu Ser Pro Leu Asn Ser Lys Ser Glu Ser
    1145                1150                1155
Leu Pro Val Ser Asp Lys Thr Ala Ile Ser Glu Thr Pro Leu Val
    1160                1165                1170
Ser Gln Phe Leu Ile Ser Asp Glu Leu Leu Leu Asp Asn Asn Ser
    1175                1180                1185
Glu Leu Gln Asp Gln Ile Thr Arg Asp Ala Asn Ser Phe Lys Ser
    1190                1195                1200
Arg Asp Gln Arg Gly Val Gln Glu Glu Lys Val Lys Asn His Glu
    1205                1210                1215
Asp Ile Phe Asp Cys Ser Arg Asp Leu Phe Ser Val Thr Phe Asp
    1220                1225                1230
Leu Gly Phe Cys Ser Pro Asp Ser Asp Asp Glu Ile Leu Glu His
    1235                1240                1245
```

-continued

```
Thr Ser Asp Ser Asn Arg Pro Leu Asp Asp Leu Tyr Gly Arg Tyr
1250                1255                1260

Leu Glu Ile Lys Glu Ile Ser Asp Ala Asn Tyr Val Ser Asn Gln
1265                1270                1275

Ala Leu Ile Pro Arg Asp His Ser Lys Asn Phe Thr Ser Gly Thr
1280                1285                1290

Val Ile Ile Pro Ser Asn Glu Asp Met Gln Asn Pro Asn Tyr Val
1295                1300                1305

His Leu Pro Leu Ser Ala Ala Lys Asn Glu Glu Leu Leu Ser Pro
1310                1315                1320

Gly Tyr Ser Gln Phe Ser Leu Pro Val Gln Lys Lys Val Met Ser
1325                1330                1335

Thr Pro Leu Ser Lys Ser Asn Thr Leu Asn Ser Phe Ser Lys Ile
1340                1345                1350

Arg Lys Glu Ile Leu Lys Thr Pro Asp Ser Ser Lys Glu Lys Val
1355                1360                1365

Asn Leu Gln Arg Phe Lys Glu Ala Leu Asn Ser Thr Phe Asp Tyr
1370                1375                1380

Ser Glu Phe Ser Leu Glu Lys Ser Lys Ser Ser Gly Pro Met Tyr
1385                1390                1395

Leu His Lys Ser Cys His Ser Val Glu Asp Gly Gln Leu Leu Thr
1400                1405                1410

Ser Asn Glu Ser Glu Asp Asp Glu Ile Phe Arg Arg Lys Val Lys
1415                1420                1425

Arg Ala Lys Gly Asn Val Leu Asn Ser Pro Glu Asp Gln Lys Asn
1430                1435                1440

Ser Glu Val Asp Ser Pro Leu His Ala Val Lys Lys Arg Arg Phe
1445                1450                1455

Pro Ile Asn Arg Ser Glu Leu Ser Ser Ser Asp Glu Ser Glu Asn
1460                1465                1470

Phe Pro Lys Pro Cys Ser Gln Leu Glu Asp Phe Lys Val Cys Asn
1475                1480                1485

Gly Asn Ala Arg Arg Gly Ile Lys Val Pro Lys Arg Gln Ser His
1490                1495                1500

Leu Lys His Val Ala Arg Lys Phe Leu Asp Asp Glu Ala Glu Leu
1505                1510                1515

Ser Glu Glu Asp Ala Glu Tyr Val Ser Ser Asp Glu Asn Asp Glu
1520                1525                1530

Ser Glu Asn Glu Gln Asp Ser Ser Leu Leu Asp Phe Leu Asn Asp
1535                1540                1545

Glu Thr Gln Leu Ser Gln Ala Ile Asn Asp Ser Glu Met Arg Ala
1550                1555                1560

Ile Tyr Met Lys Ser Leu Arg Ser Pro Met Met Asn Asn Lys Tyr
1565                1570                1575

Lys Met Ile His Lys Thr His Lys Asn Ile Asn Ile Phe Ser Gln
1580                1585                1590

Ile Pro Glu Gln Asp Glu Thr Tyr Leu Glu Asp Ser Phe Cys Val
1595                1600                1605

Asp Glu Glu Glu Ser Cys Lys Gly Gln Ser Ser Glu Glu Glu Val
1610                1615                1620

Cys Val Asp Phe Asn Leu Ile Thr Asp Asp Cys Phe Ala Asn Ser
1625                1630                1635

Lys Lys Tyr Lys Thr Arg Arg Ala Val Met Leu Lys Glu Met Met
1640                1645                1650
```

```
Glu Gln Asn Cys Ala His Ser Lys Lys Lys Leu Ser Arg Ile Ile
    1655            1660                1665

Leu Pro Asp Asp Ser Ser Glu Glu Asn Asn Val Asn Asp Lys
    1670            1675                1680

Arg Glu Ser Asn Ile Ala Val Asn Pro Ser Thr Val Lys Lys Asn
    1685            1690                1695

Lys Gln Gln Asp His Cys Leu Asn Ser Val Pro Ser Gly Ser Ser
    1700            1705                1710

Ala Gln Ser Lys Val Arg Ser Thr Pro Arg Val Asn Pro Leu Ala
    1715            1720                1725

Lys Gln Ser Lys Gln Thr Ser Leu Asn Leu Lys Asp Thr Ile Ser
    1730            1735                1740

Glu Val Ser Asp Phe Lys Pro Gln Asn His Asn Glu Val Gln Ser
    1745            1750                1755

Thr Thr Pro Pro Phe Thr Thr Val Asp Ser Gln Lys Asp Cys Arg
    1760            1765                1770

Lys Phe Pro Val Pro Gln Lys Asp Gly Ser Ala Leu Glu Asp Ser
    1775            1780                1785

Ser Thr Ser Gly Ala Ser Cys Ser Lys Ser Arg Pro His Leu Ala
    1790            1795                1800

Gly Thr His Thr Ser Leu Arg Leu Pro Gln Glu Gly Lys Gly Thr
    1805            1810                1815

Cys Ile Leu Val Gly Gly His Glu Ile Thr Ser Gly Leu Glu Val
    1820            1825                1830

Ile Ser Ser Leu Arg Ala Ile His Gly Leu Gln Val Glu Val Cys
    1835            1840                1845

Pro Leu Asn Gly Cys Asp Tyr Ile Val Ser Asn Arg Met Val Val
    1850            1855                1860

Glu Arg Arg Ser Gln Ser Glu Met Leu Asn Ser Val Asn Lys Asn
    1865            1870                1875

Lys Phe Ile Glu Gln Ile Gln His Leu Gln Ser Met Phe Glu Arg
    1880            1885                1890

Ile Cys Val Ile Val Glu Lys Asp Arg Glu Lys Thr Gly Asp Thr
    1895            1900                1905

Ser Arg Met Phe Arg Arg Thr Lys Ser Tyr Asp Ser Leu Leu Thr
    1910            1915                1920

Thr Leu Ile Gly Ala Gly Ile Arg Ile Leu Phe Ser Ser Cys Gln
    1925            1930                1935

Glu Glu Thr Ala Asp Leu Leu Lys Glu Leu Ser Leu Val Glu Gln
    1940            1945                1950

Arg Lys Asn Val Gly Ile His Val Pro Thr Val Val Asn Ser Asn
    1955            1960                1965

Lys Ser Glu Ala Leu Gln Phe Tyr Leu Ser Ile Pro Asn Ile Ser
    1970            1975                1980

Tyr Ile Thr Ala Leu Asn Met Cys His Gln Phe Ser Ser Val Lys
    1985            1990                1995

Arg Met Ala Asn Ser Ser Leu Gln Glu Ile Ser Met Tyr Ala Gln
    2000            2005                2010
```

```
Val Thr  His Gln Lys Ala Glu  Glu Ile Tyr Arg Tyr  Ile His Tyr
    2015             2020                 2025

Val Phe  Asp Ile Gln Met Leu  Pro Asn Asp Leu Asn  Gln Asp Arg
    2030             2035                 2040

Leu Lys  Ser Asp Ile
    2045
```